United States Patent
Wei et al.

(10) Patent No.: US 12,351,587 B2
(45) Date of Patent: Jul. 8, 2025

(54) BICYCLIC COMPOUND AS RIP-1 KINASE INHIBITOR AND APPLICATION THEREOF

(71) Applicant: MEDSHINE DISCOVERY INC., Jiangsu (CN)

(72) Inventors: Wei Wei, Shanghai (CN); Peng Li, Shanghai (CN); Haiying He, Shanghai (CN); Shuhui Chen, Shanghai (CN)

(73) Assignee: Medshine Discovery Inc., Nanjing (CN)

( * ) Notice: Subject to any disclaimer, the term of this patent is extended or adjusted under 35 U.S.C. 154(b) by 766 days.

(21) Appl. No.: 17/614,939

(22) PCT Filed: May 29, 2020

(86) PCT No.: PCT/CN2020/093280
§ 371 (c)(1),
(2) Date: Nov. 29, 2021

(87) PCT Pub. No.: WO2020/239074
PCT Pub. Date: Dec. 3, 2020

(65) Prior Publication Data
US 2022/0242877 A1     Aug. 4, 2022

(30) Foreign Application Priority Data

May 31, 2019   (CN) .......................... 201910471672.3
Nov. 8, 2019    (CN) .......................... 201911089490.6
May 20, 2020   (CN) .......................... 202010432710.7

(51) Int. Cl.
C07D 498/04   (2006.01)
C07D 403/12   (2006.01)
C07D 413/12   (2006.01)
C07D 519/00   (2006.01)

(52) U.S. Cl.
CPC .......... *C07D 498/04* (2013.01); *C07D 403/12* (2013.01); *C07D 413/12* (2013.01); *C07D 519/00* (2013.01)

(58) Field of Classification Search
CPC .. C07D 498/04; C07D 413/02; C07D 413/00; C07D 403/00; C07D 403/02; C07D 519/00
See application file for complete search history.

(56) References Cited

FOREIGN PATENT DOCUMENTS

CN        109071504 A       12/2018
EA          028991 B1        1/2018
WO    WO-2017136727 A2 *    8/2017    ............. A61K 31/55

OTHER PUBLICATIONS

Wegner, K. W.; et al. "Complex Pathologic Roles of RIPK1 and RIPK3: Moving Beyond Necroptosis" 2017, Trends in Pharmacological Sciences, vol. 38, pp. 202-225. (Year: 2017).*

Xia, C.; et al. "Structure-based bioisosterism design of thiobenzoxazepinones as novel necroptosis inhibitors" 2021, European Journal of Medicinal Chemistry, vol. 220, article No. 113484. (Year: 2021).*

Harris, P. A.; et al. "Discovery of a First-in-Class Receptor Interacting Protein 1 (RIP1) Kinase Specific Clinical Candidate (GSK2982772) for the Treatment of Inflammatory Diseases" 2017, Journal of Medicinal Chemistry, vol. 60, pp. 1247-1261. (Year: 2017).*

Berger et al., Life after death: RIP1 and RIP3 move beyond necroptosis. Cell Death Discov. Jul. 18, 2016;2:16056(1-2).

Lukens et al., RIP1-driven autoinflammation targets IL-1α independently of inflammasomes and RIP3. Nature. Jun. 13, 2013;498(7453):224-7. Epub May 26, 2013.

* cited by examiner

*Primary Examiner* — Eric Olson
*Assistant Examiner* — Benjamin M Brandsen
(74) *Attorney, Agent, or Firm* — Mintz Levin Cohn Ferris Glovsky and Popeo, P.C.

(57) ABSTRACT

A compound represented by formula (I), isomers or pharmaceutically acceptable salts thereof, and application thereof in the preparation of drugs for treating diseases related to RIP-1 (receptor interacting protein) kinase.

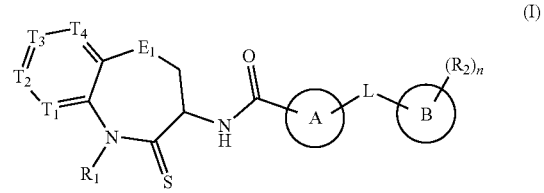

(I)

19 Claims, No Drawings

BICYCLIC COMPOUND AS RIP-1 KINASE INHIBITOR AND APPLICATION THEREOF

The present application is a United States National Phase under 35 U.S.C. § 371 of International Application No. PCT/CN2020/093280, filed May 29, 2020, which claims the priority of: CN201910471672.3, filed on May 31, 2019; CN201911089490.6, filed on Nov. 8, 2019; and CN202010432710.7, filed on May 20, 2020.

FIELD OF THE INVENTION

The present disclosure relates to a compound represented by formula (I), or an isomer or pharmaceutically acceptable salt thereof, and use thereof in the manufacture of a medicament for treating diseases related to RIP-1 (receptor-interacting protein) kinase.

BACKGROUND OF THE INVENTION

RIP1 is a critical upstream kinase that regulates cell necrosis and apoptosis. RIP1 is also involved in a variety of inflammatory signaling pathways, and can be stimulated by TNF and TLR family ligands to trigger an inflammatory response (Weinlich, R. Nat. Rev. Mol. Cell. Biol, 2017, 18, 127; Pasparakis M. et al. Nature 2015, 517, 311; Berger, S. B. Cell Death Discovery, 2016, 2, e16056). RIP1 drives a variety of inflammatory signaling pathways [Fas ligand, TNF-related apoptosis inducing ligand (TRAIL), TLR3 and TLR4] through TNF receptor 1 (Lukens J. R., et al. Nature, 2013, 498, 224). Inhibiting the activity of RIP1 can be used as a treatment for many inflammatory diseases.

SUMMARY OF THE INVENTION

The present disclosure provides a compound of formula (I), or an isomer or pharmaceutically acceptable salt thereof,

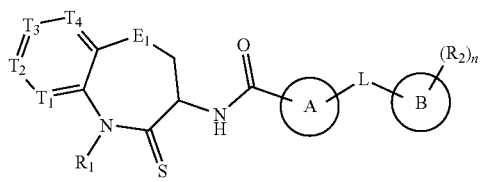

wherein:
$T_1$ is selected from N and $CR_{1f}$;
$T_2$ is selected from N and $CR_{2f}$;
$T_3$ is selected from N and $CR_{3f}$;
$T_4$ is selected from N and $CR_{4f}$;
$E_1$ is selected from $C(R_{1e})_2$, O, C(=O), S, and $NR_{2e}$;
Ring A is selected from 1,2,4-triazolyl, 1,2,3-triazolyl, imidazolyl, isoxazolyl, 1,3,4-oxadiazolyl,

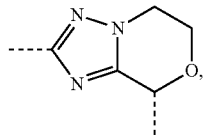

tetrazolyl, pyridyl, and

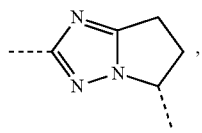

wherein the 1,2,4-triazolyl, 1,2,3-triazolyl, imidazolyl, isoxazolyl, 1,3,4-oxadiazolyl,

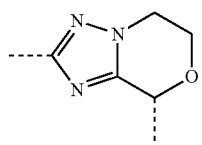

tetrazolyl, pyridyl, and

are optionally substituted with 1, 2 or 3 halogen or $C_{1-3}$ alkyl;
Ring B is selected from phenyl

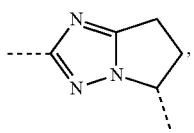

L is selected from single bond, O, C(=O), S, NH, and $C_{1-3}$ alkyl, wherein the $C_{1-3}$ alkyl is optionally substituted with 1, 2 or 3 $R_a$;
$R_1$ is selected from H and $C_{1-3}$ alkyl, wherein the $C_{1-3}$ alkyl is optionally substituted with 1, 2 or 3 $R_b$;
$R_{1f}$, $R_{2f}$, $R_{3f}$, and $R_{4f}$ are each independently selected from H, F, Cl, Br, I, OH, CN, $NH_2$, $C_{1-3}$ alkyl, COOH, and —C(=O)$NH_2$, wherein the $C_{1-3}$ alkyl is optionally substituted with 1, 2 or 3 $R_c$;
$R_{1e}$ is each independently selected from H, F, Cl, Br, I, OH, CN, $NH_2$, and $C_{1-3}$ alkyl, wherein the $C_{1-3}$ alkyl is optionally substituted with 1, 2 or 3 $R_d$;
$R_{2e}$ is selected from H and $C_{1-3}$ alkyl, wherein the $C_{1-3}$ alkyl is optionally substituted with 1, 2 or 3 $R_e$;
$R_2$ is each independently selected from H, F, Cl, Br, I, OH, $NH_2$, CN, $C_{1-3}$ alkyl, and $C_{1-3}$ alkoxy, wherein the $C_{1-3}$ alkyl and $C_{1-3}$ alkoxy are optionally substituted with 1, 2 or 3 $R_f$;
n is 1, 2, 3, 4, or 5;
$R_a$, $R_b$, $R_c$, $R_d$, $R_e$, and $R_f$ are each independently selected from F, Cl, Br, I, OH, CN, $NH_2$, and D.

The present disclosure provides a compound of formula (I), or an isomer or pharmaceutically acceptable salt thereof,

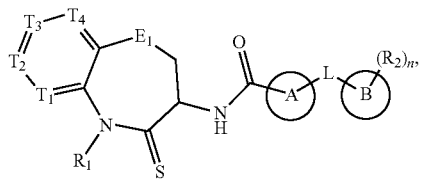
(I)

wherein $T_1$ is selected from N and $CR_{1t}$;

$T_2$ is selected from N and $CR_{2t}$;

$T_3$ is selected from N and $CR_{3t}$;

$T_4$ is selected from N and $C_{4t}$;

$E_1$ is selected from $C(R_{1e})_2$, O, C(=O), S, and $NR_{2e}$;

Ring A is selected from 1,2,4-triazolyl, 1,2,3-triazolyl, imidazolyl, isoxazolyl, 1,3,4-oxadiazolyl, and

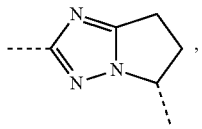

wherein the 1,2,4-triazolyl, 1,2,3-triazolyl, imidazolyl, isoxazolyl, 1,3,4-oxadiazolyl, and

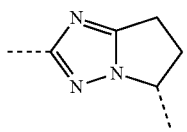

are optionally substituted with 1, 2 or 3 halogen or $C_{1-3}$ alkyl;

Ring B is phenyl;

L is selected from single bond, O, C(=O), S, NH, and $C_{1-3}$ alkyl, wherein the $C_{1-3}$ alkyl is optionally substituted with 1, 2 or 3 $R_a$;

$R_1$ is selected from H and $C_{1-3}$ alkyl, wherein the $C_{1-3}$ alkyl is optionally substituted with 1, 2 or 3 $R_b$;

$R_{1t}$, $R_{2t}$, $R_{3t}$, and $R_{4t}$ are each independently selected from H, F, Cl, Br, I, OH, CN, $NH_2$, and $C_{1-3}$ alkyl, wherein the $C_{1-3}$ alkyl is optionally substituted with 1, 2 or 3 $R_c$;

$R_{1e}$ is each independently selected from H, F, Cl, Br, I, OH, CN, $NH_2$, and $C_{1-3}$ alkyl, wherein the $C_{1-3}$ alkyl is optionally substituted with 1, 2 or 3 $R_d$;

$R_{2e}$ is selected from H and $C_{1-3}$ alkyl, wherein the $C_{1-3}$ alkyl is optionally substituted with 1, 2 or 3 $R_e$;

$R_2$ is each independently selected from H, F, Cl, Br, I, OH, $NH_2$, CN, and $C_{1-3}$ alkyl, wherein the $C_{1-3}$ alkyl is optionally substituted with 1, 2 or 3 $R_f$;

n is 1, 2, 3, 4, or 5;

$R_a$, $R_b$, $R_c$, $R_d$, $R_e$, and $R_f$ are each independently selected from F, Cl, Br, I, OH, CN, $NH_2$, and D.

The present disclosure provides a compound of formula (I), or an isomer or pharmaceutically acceptable salt thereof,

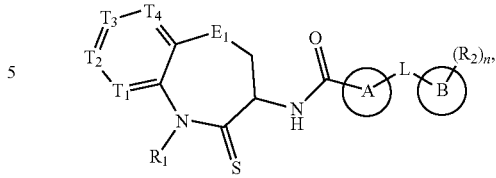
(I)

wherein $T_1$ is N or $CR_{1t}$;

$T_2$ is N or $CR_{2t}$;

$T_1$ is N or $CR_{3t}$;

$T_4$ is N or $CR_{4t}$;

$E_1$ is $C(R_{1e})_2$, O, C(=O), S, or $NR_{2e}$;

Ring A is 5-membered heteroaryl optionally substituted with $C_{1-3}$ alkyl:

Ring B is phenyl or 6-membered heteroaryl;

L is O, C(=O), S, NH, or $C_{1-3}$ alkyl, wherein the $C_{1-3}$ alkyl is optionally substituted with 1, 2 or 3 $R_a$;

$R_1$ is selected from H and $C_{1-3}$ alkyl, wherein the $C_{1-3}$ alkyl is optionally substituted with 1, 2 or 3 $R_b$;

$R_{1t}$, $R_{2t}$, $R_{3t}$, and $R_{4t}$ are each independently selected from H, F, Cl, Br, I, OH, CN, $NH_2$, and $C_{1-3}$ alkyl, wherein the $C_{1-3}$ alkyl is optionally substituted with 1, 2 or 3 $R_c$;

$R_{1e}$ is each independently selected from H, F, Cl, Br, I, OH, CN, $NH_2$, and $C_{1-3}$ alkyl, wherein the $C_{1-3}$ alkyl is optionally substituted with 1, 2 or 3 $R_d$;

$R_{2e}$ is selected from H and $C_{1-3}$ alkyl, wherein the $C_{1-3}$ alkyl is optionally substituted with 1, 2 or 3 $R_e$:

$R_2$ is each independently selected from H, F, Cl, Br, I, OH, $NH_2$, CN, and $C_{1-3}$ alkyl, wherein the $C_{1-3}$ alkyl is optionally substituted with 1, 2 or 3 $R_f$;

n is 1, 2, 3, 4, or 5;

$R_a$, $R_b$, $R_c$, $R_d$, $R_e$, and $R_f$ are each independently selected from F, Cl, Br, I, OH, CN, and $NH_2$.

In some embodiments disclosed herein, the above-mentioned $R_1$ is selected from H and $CH_3$, wherein the $CH_3$ is optionally substituted with 1, 2 or 3 $R_b$, and other variables are as defined herein.

In some embodiments disclosed herein, the above-mentioned $R_1$ is selected from H, $CH_3$, and $CD_3$, and other variables are as defined herein.

In some embodiments disclosed herein, the above-mentioned $R_1$ is selected from H and $CH_3$, and other variables are as defined herein.

In some embodiments disclosed herein, the above-mentioned $R_{1t}$, $R_{2t}$, $R_{3t}$, and $R_{4t}$ are each independently selected from H, F, Cl, Br, I, OH, CN, $NH_2$, $CH_3$, COOH, and —C(=O)$NH_2$, wherein the $CH_3$ is optionally substituted with 1, 2 or 3 $R_c$, and other variables are as defined herein.

In some embodiments disclosed herein, the above-mentioned $R_{1t}$, $R_{2t}$, $R_{3t}$, and $R_{4t}$ are each independently selected from H, F, Cl, Br, I, OH, CN, $NH_2$, and $CH_3$, wherein the $CH_3$ is optionally substituted with 1, 2 or 3 $R_c$, and other variables are as defined herein.

In some embodiments disclosed herein, the above-mentioned $R_{1t}$, $R_{2t}$, $R_{3t}$, and $R_{4t}$ are each independently selected from H, F, Cl, Br, I, OH, CN, $NH_2$, and $CH_3$, and other variables are as defined herein.

In some embodiments disclosed herein, the above-mentioned $R_{1e}$ is each independently selected from H, F, Cl, Br, I, OH, CN, $NH_2$, and $CH_3$, and other variables are as defined herein.

In some embodiments disclosed herein, the above-mentioned $R_{2e}$ is selected from H and $CH_3$, and other variables are as defined herein.

In some embodiments disclosed herein, the above-mentioned $E_1$ is $CH_2$, O, C(=O), S, or NH, and other variables are as defined herein.

In some embodiments disclosed herein, the above-mentioned $R_2$ is each independently selected from H, F, Cl, Br, I, OH, $NH_2$, CN, $CH_3$, and $OCH_3$, wherein the $CH_3$ and $OCH_3$ are optionally substituted with 1, 2 or 3 $R_f$, and other variables are as defined herein.

In some embodiments disclosed herein, the above-mentioned $R_2$ is each independently selected from H, F, Cl, Br, I, OH, $NH_2$, CN, $CH_3$, $OCH_3$, $CF_3$, and $OCF_3$, and other variables are as defined herein.

In some embodiments disclosed herein, the above-mentioned $R_2$ is each independently selected from H, F, Cl, Br, I, OH, $NH_2$, and CN, and other variables are as defined herein.

In some embodiments disclosed herein, the above-mentioned Ring A is selected from

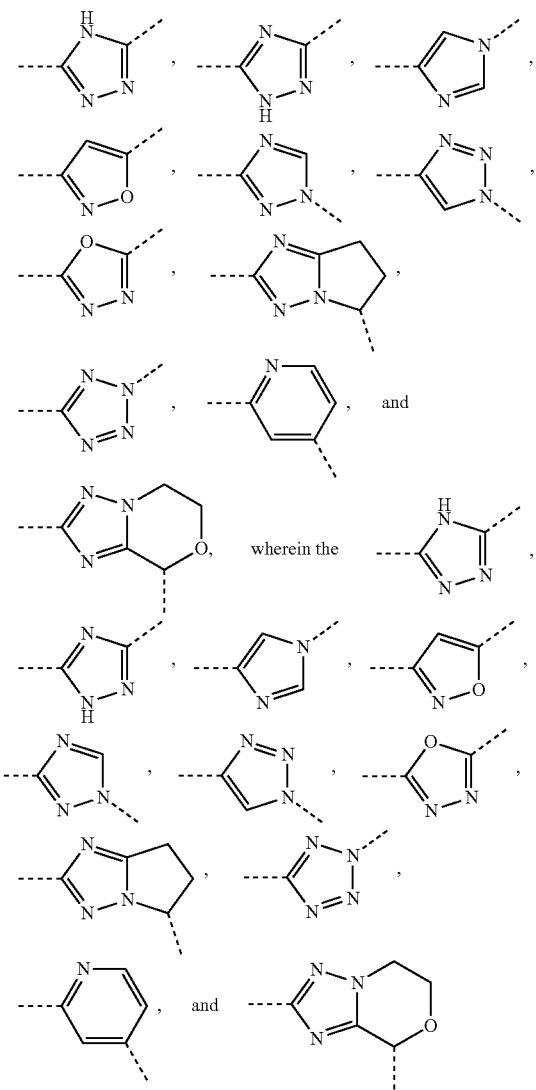

are optionally substituted with 1, 2 or 3 halogen or $C_{1-3}$ alkyl, and other variables are as defined herein.

In some embodiments disclosed herein, the above-mentioned Ring A is selected from

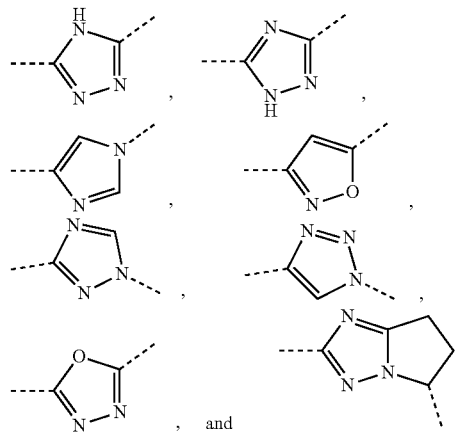

In some embodiments disclosed herein, the above-mentioned Ring A is pyrrolyl, imidazolyl, pyrazolyl, furyl, thienyl, oxazolyl, isoxazolyl, thiazolyl, 1,2,3-triazolyl, 1,2,4-triazolyl, or 1,3,4-thiadiazolyl, wherein the pyrrolyl, imidazolyl, pyrazolyl, furyl, thienyl, oxazolyl, isoxazolyl, thiazolyl, 1,2,3-triazolyl, 1,2,4-triazolyl, or 1,3,4-thiadiazolyl is optionally substituted with $C_{1-3}$ alkyl, and other variables are as defined herein.

In some embodiments disclosed herein, the above-mentioned L is selected from single bond, —$CH_2$—, and —O—, and other variables are as defined herein.

In some embodiments disclosed herein, the above-mentioned L is selected from single bond and —$CH_2$—, and other variables are as defined herein.

In some embodiments disclosed herein, the above-mentioned Ring A is

and other variables are as defined herein.

In some embodiments disclosed herein, the above-mentioned Ring B is phenyl or pyridyl, and other variables are as defined herein.

The present disclosure also includes some embodiments that are obtained by combining any of the above-mentioned variables.

In some embodiments disclosed herein, the above-mentioned compound is selected from

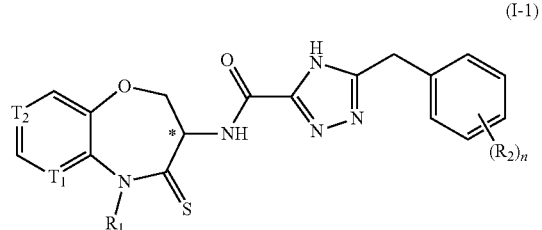

(I-1)

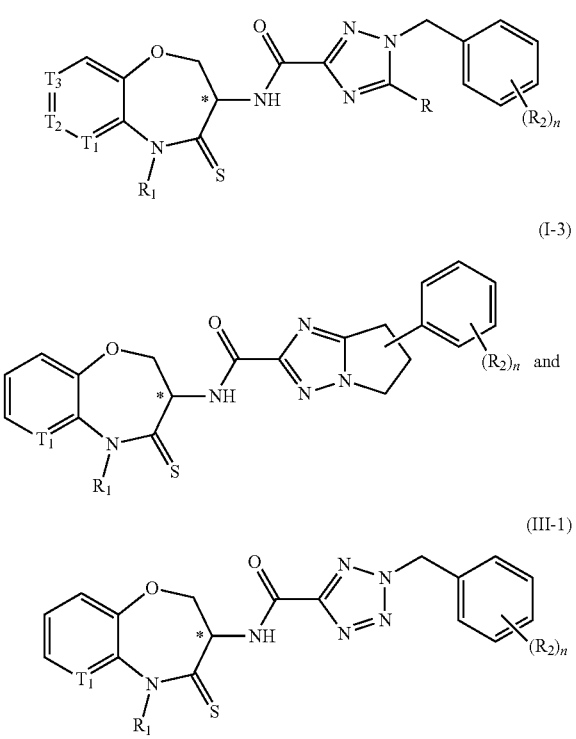

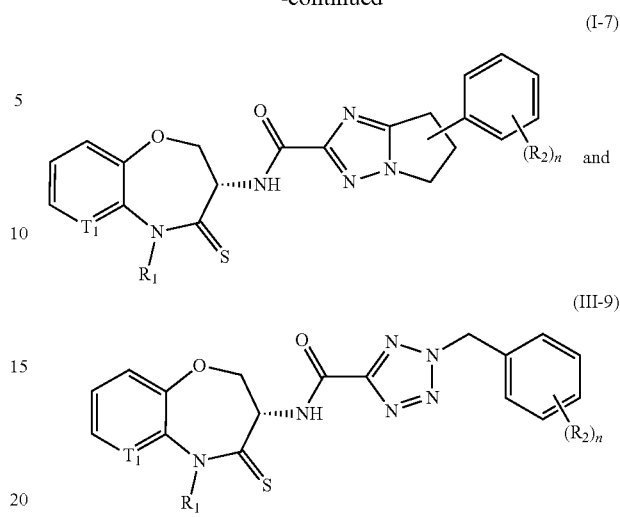

wherein n, $T_1$, $T_2$, $T_3$, $R_1$, $R_2$, and R are as defined herein;

or an isomer or pharmaceutically acceptable salt thereof.

The present disclosure also provides compounds of the formulae below, or isomers or pharmaceutically acceptable salts thereof:

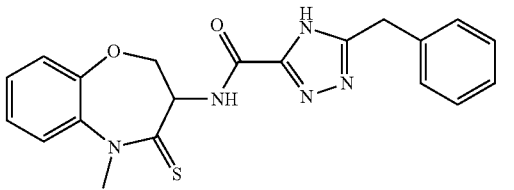

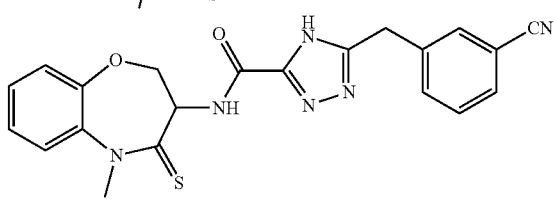

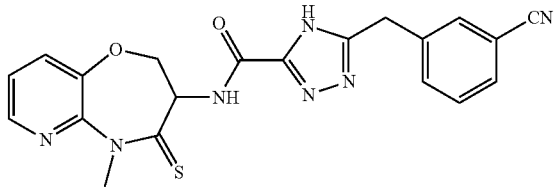

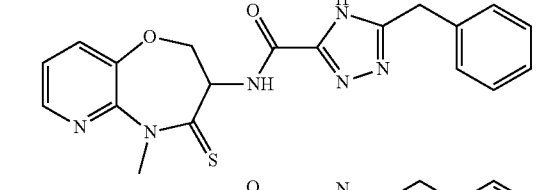

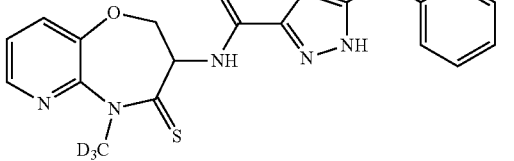

wherein n, $T_1$, $T_2$, $T_3$, $R_1$, $R_2$, and R are as defined herein;

the carbon atom with "*" is a chiral carbon atom, which exists in the form of a single (R) or (S) enantiomer or a mixture enriched in one enantiomer;

or an isomer or pharmaceutically acceptable salt thereof.

In some embodiments disclosed herein, the above-mentioned compound is selected from

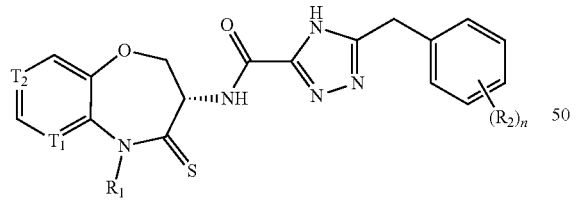

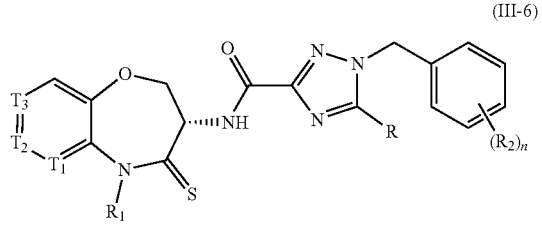

-continued

11
-continued
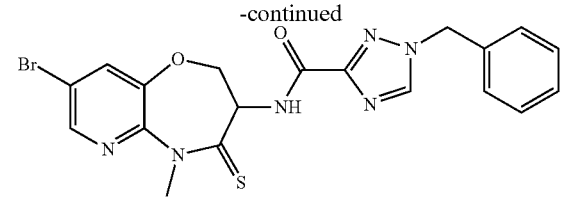
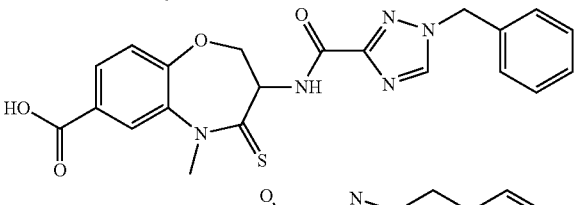
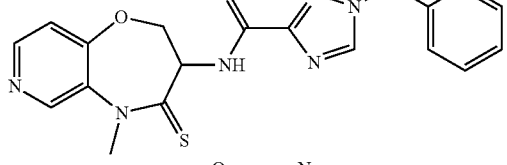
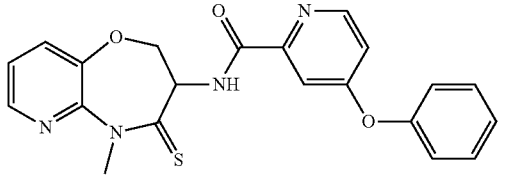
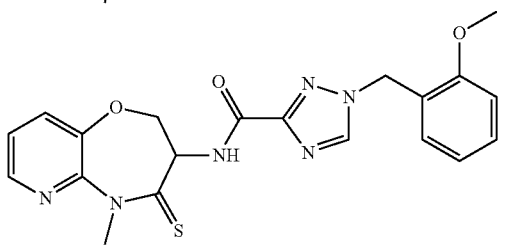
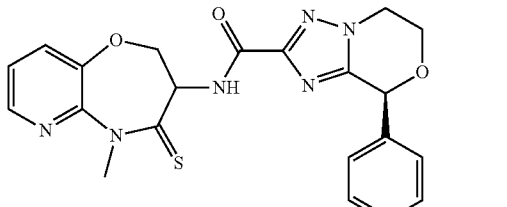
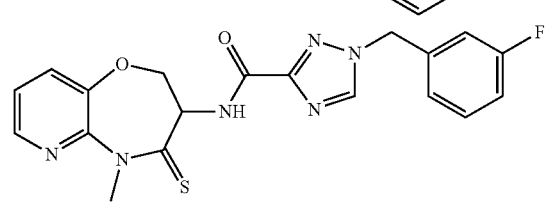
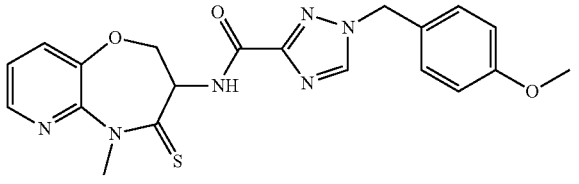
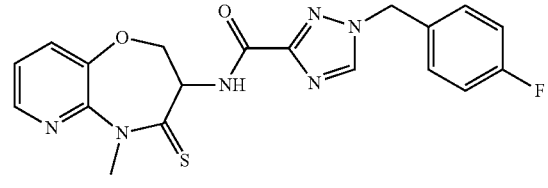
12
-continued
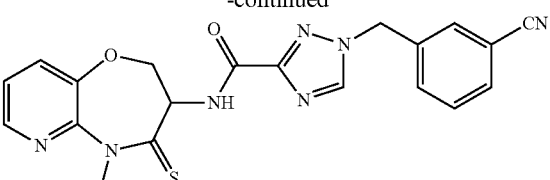
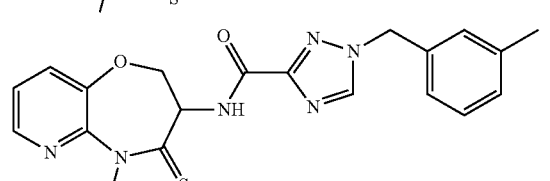
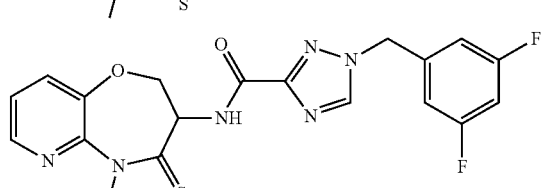
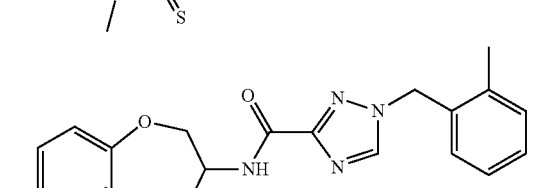
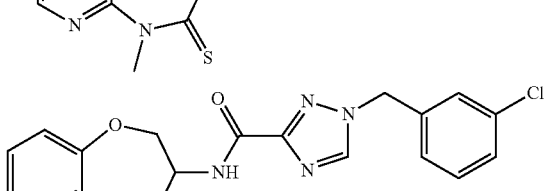
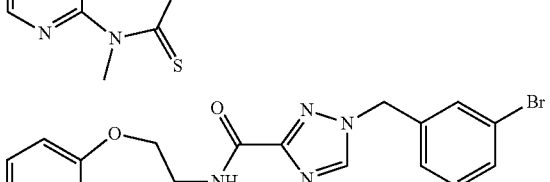
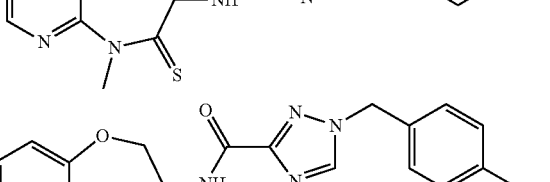
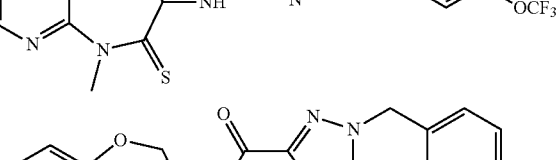
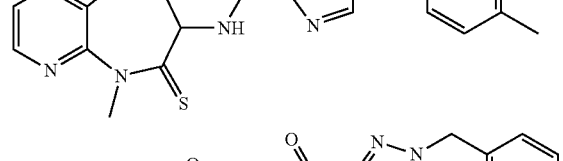
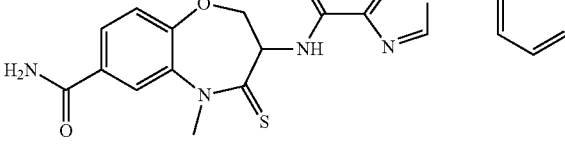

-continued
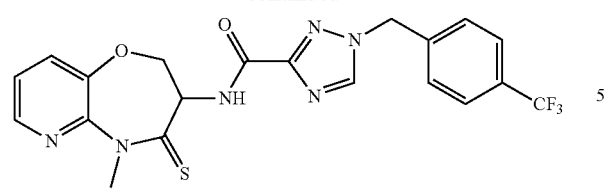
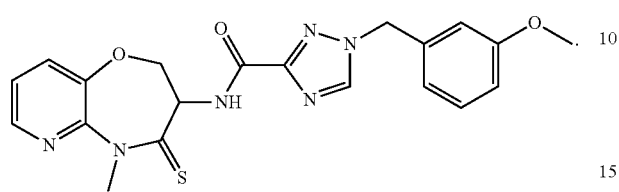
In some embodiments disclosed herein, the above-mentioned compound is selected from
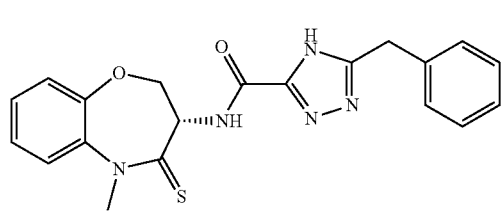
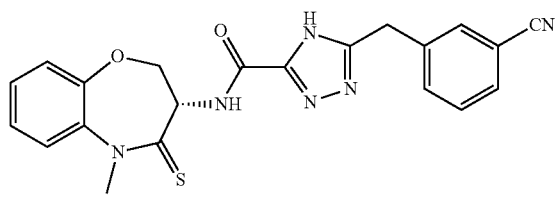
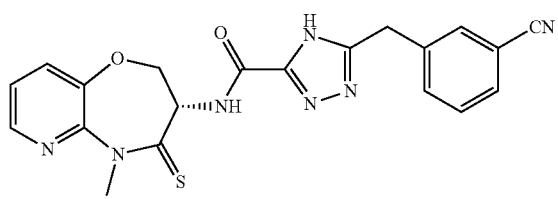
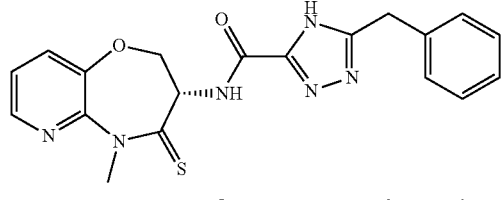
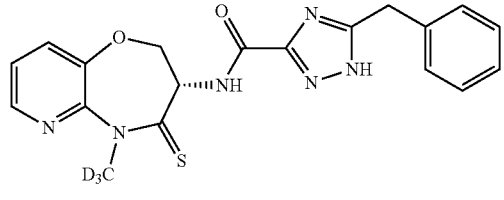
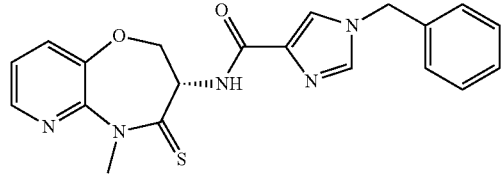
-continued
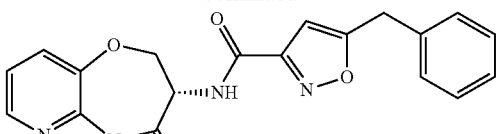
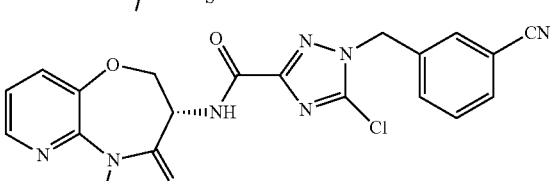

-continued
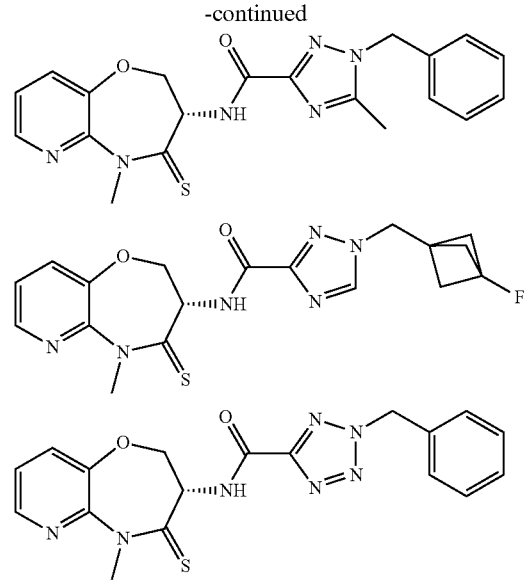
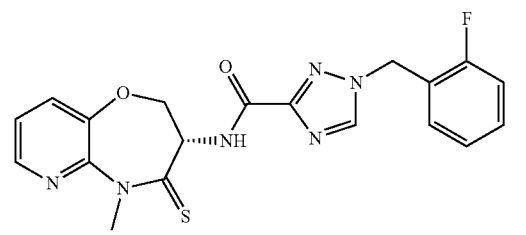
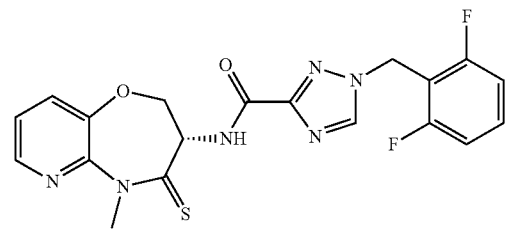
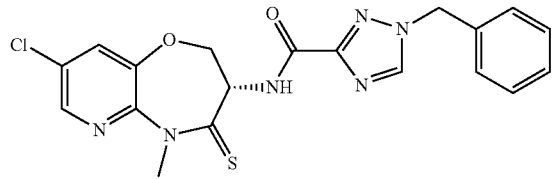
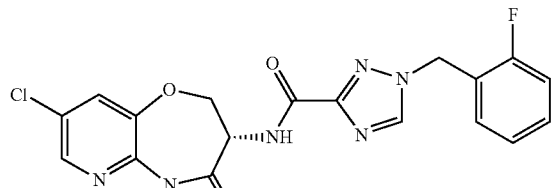
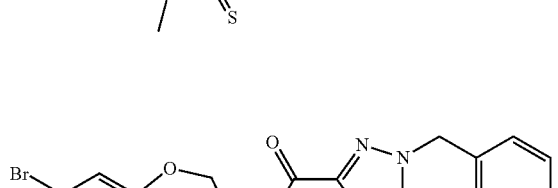
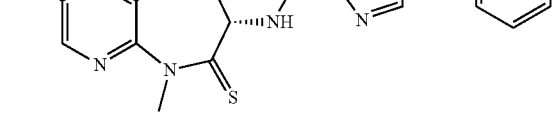
-continued
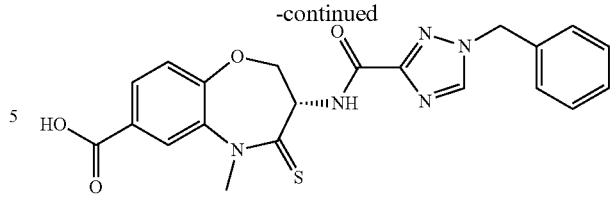
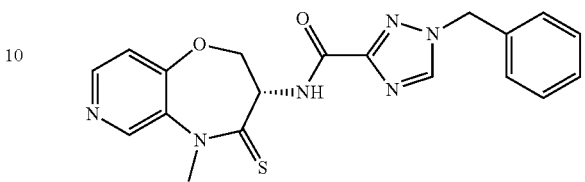
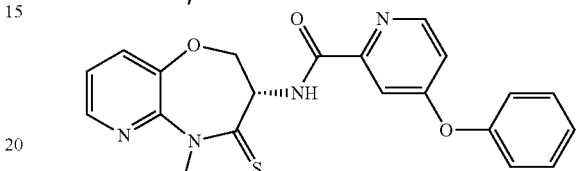
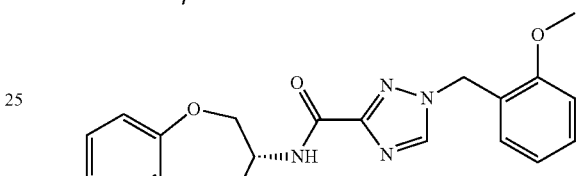
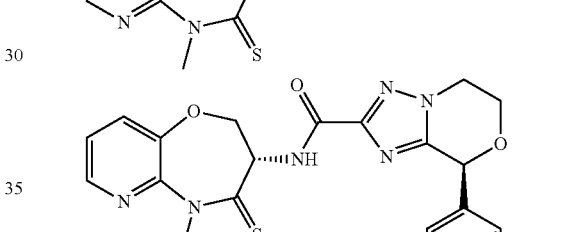
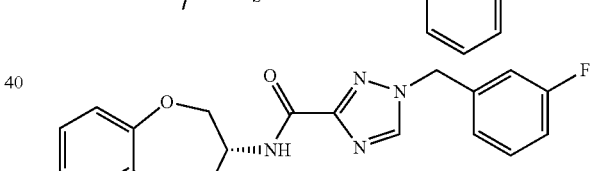
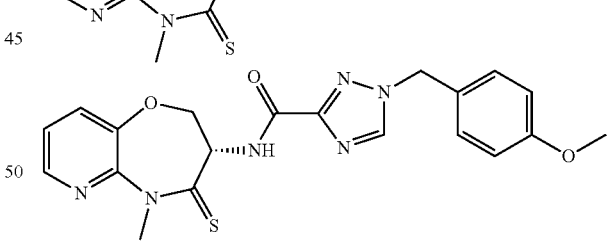
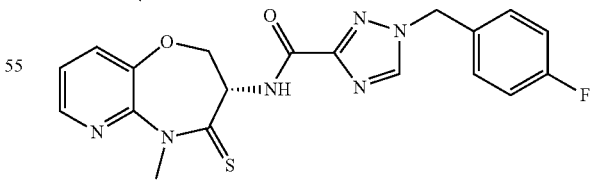
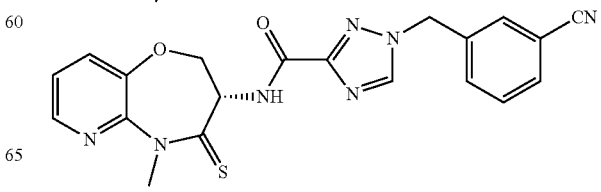

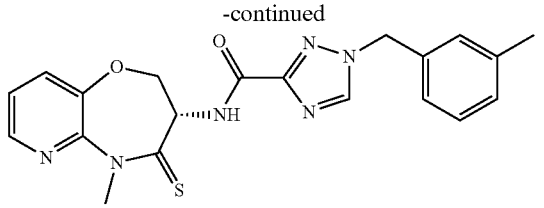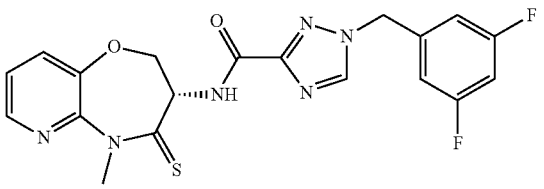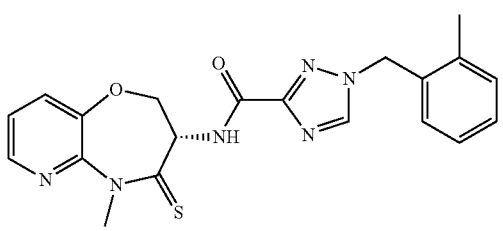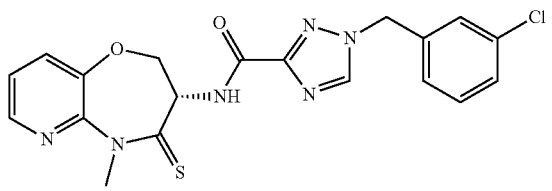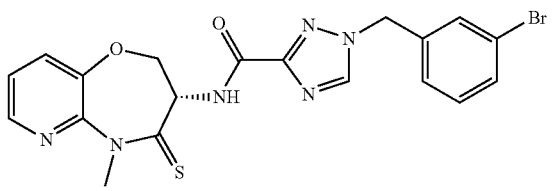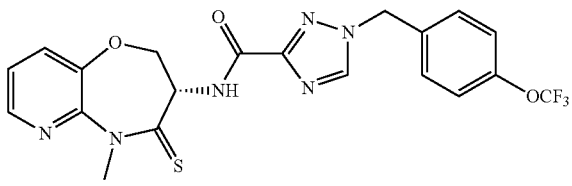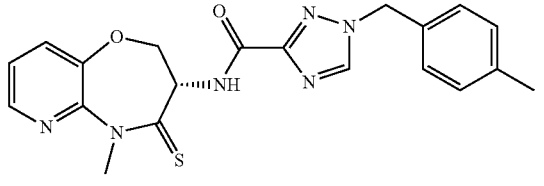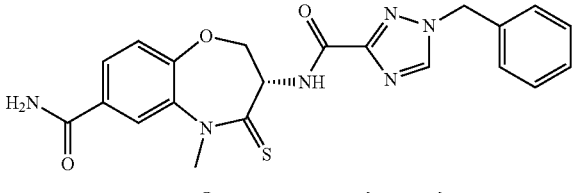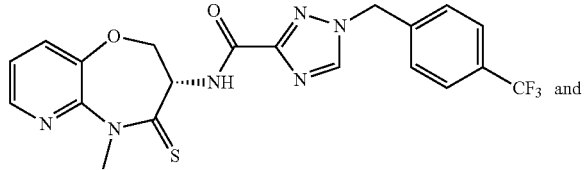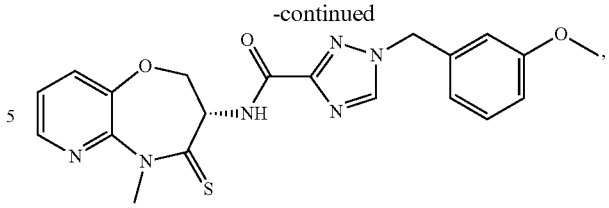

or an isomer or pharmaceutically acceptable salt thereof.

The present disclosure also provides the use of the above-mentioned compound, or the isomer or pharmaceutically acceptable salt thereof, in the manufacture of a medicament for treating diseases related to RIP-1 kinase.

Technical Effects

As a novel RIP-1 kinase inhibitor, the compound of the present disclosure has a good inhibitory effect on the programmed cell necrosis (Necroptosis) of U937 cells induced by TNFα/QVD-OPh, and has achieved a good effect of inhibiting the decrease of body temperature of mice in a model of TNF-driven systemic inflammatory response syndrome.

Definitions and Terms

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" means a salt of compounds disclosed herein that is prepared by reacting the compound having a specific substituent disclosed herein with a relatively non-toxic acid or base. When compounds disclosed herein contain a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When compounds disclosed herein contain a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

Unless otherwise specified, the term "isomer" is intended to include geometric isomers, cis- or trans-isomers, stereoisomers, enantiomers, optical isomers, diastereomers, and tautomers.

Compounds disclosed herein may be present in a specific geometric or stereoisomeric form. The present disclosure contemplates all such compounds, including cis and trans isomers. (−)- and (+)-enantiomers, (R)- and (S)-enantiomers, diastereoisomer, (D)-isomer, (L)-isomer, and a racemic mixture and other mixtures, for example, a mixture enriched in enantiomer or diastereoisomer, all of which are encompassed within the scope disclosed herein. The substituent such as alkyl may have an additional asymmetric carbon atom. All these isomers and mixtures thereof are encompassed within the scope disclosed herein.

Unless otherwise specified, the term "enantiomer" or "optical isomer" means stereoisomers that are in a mirrored relationship with each other.

Unless otherwise specified, the term "cis-trans isomer" or "geometric isomer" is produced by the inability of a double bond or a single bond between ring-forming carbon atoms to rotate freely.

Unless otherwise specified, the term "diastereomer" means a stereoisomer in which two or more chiral centers of are contained in a molecule and is in a non-mirrored relationship between molecules.

Unless otherwise specified, "(D)" or "(+)" means dextroisomer, "(L)" or "(−)" means levoisomer, and "(DL)" or "(±)" means racemate.

Unless otherwise specified, a wedged solid bond ( ) and a wedged dashed bond ( ) indicate the absolute configuration of a stereocenter; a straight solid bond ( ) and a straight dashed bond ( ) indicate the relative configuration of a stereocenter; a wavy line ( ) indicates a wedged solid bond ( ) or a wedged dashed bond ( ) or a wavy line ( ) indicates a straight solid bond ( ) and a straight dashed bond ( ).

Unless otherwise specified, when a double bond structure such as a carbon-carbon double bond, a carbon-nitrogen double bond, and a nitrogen-nitrogen double bond is present in a compound, and each atom on the double bond is attached to two different substituents (in the double bond containing a nitrogen atom, a pair of lone pair electrons on the nitrogen atom is considered as one of the substituents to which it is attached), the compound represents (Z) isomer, (E) isomer, or a mixture of two isomers of the compound, if the atoms on the double bond in the compound are attached to their substituents by a wavy line ( ). For example, the compound having following formula (A) means that the compound is present as a single isomer of formula (A-1) or formula (A-2) or as a mixture of two isomers of formula (A-1) and formula (A-2); and the compound having following formula (B) means that the compound is present as a single isomer of formula (B-1) or formula (B-2) or as a mixture of two isomers of formula (B-1) and formula (B-2). The compound having following formula (C) means that the compound is present as a single isomer of formula (C-1) or formula (C-2) or as a mixture of two isomers of formula (C-1) and formula (C-2).

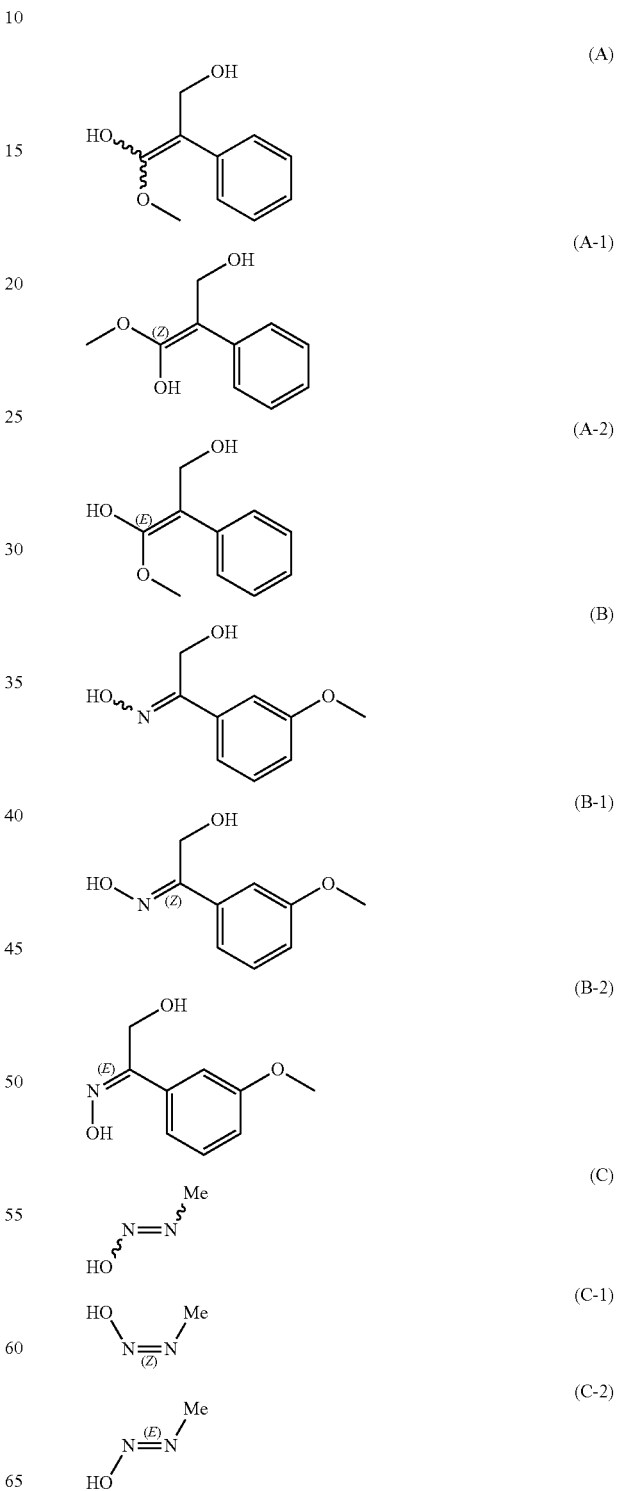

Compounds disclosed herein may be present in a particular form. Unless otherwise specified, the terms "tautomer" or "tautomeric form" means that different functional groups are in dynamic equilibrium at room temperature and can be rapidly converted into each other. If tautomers are possible (as in solution), a chemical equilibrium of tautomers can be achieved. For example, proton tautomers (also known as prototropic tautomers) include interconversions by proton transfer, such as keto-enol isomerization and imine-enamine isomerization. Valence tautomers include interconversions by recombination of some bonding electrons. A specific example of keto-enol tautomerization is interconversion between two tautomers pentane-2, 4-dione and 4-hydroxy-pent-3-en-2-one.

Unless otherwise specified, the term "enriched in one isomer", "isomer enriched". "enriched in one enantiomer" or "enantiomeric enriched" means that the content of one isomer or enantiomer is less than 100%, and the content of the isomer or enantiomer is 60% or more, or 70% or more, or 80% or more, or 90% or more, or 95% or more, or 96% or more, or 97% or more, 98% or more, 99% or more, 99.5% or more, 99.6% or more, 99.7% or more, 99.8% or more, or 99.9% or more.

Unless otherwise specified, the term "isomer excess" or "enantiomeric excess" means the difference between the relative percentages of two isomers or two enantiomers. For example, if one isomer or enantiomer is present in an amount of 90% and the other isomer or enantiomer is present in an amount of 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to afford the pure enantiomer. In addition, the enantiomer and the diastereoisomer are generally isolated through chromatography which uses a chiral stationary phase and optionally combines with a chemical derivative method (for example, carbamate generated from amine).

Compounds disclosed herein may contain an unnatural proportion of atomic isotopes at one or more of the atoms that make up the compounds. For example, a compound may be labeled with a radioisotope such as tritium ($^3$H), iodine-125 ($^{125}$I) or C-14 ($^{14}$C). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is oxo (i.e., =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0 to 2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A.

When an enumerated substituent does not indicate the atom through which the enumerated substituent is linked to the substituted group, such substituent can be bonded through any of its atoms. For example, a pyridyl group as a substituent may be linked to the substituted group through any one of carbon atoms on the pyridine ring.

When an enumerated linking group does not indicate its linking direction, its linking direction is arbitrary. For example, when the linking group L in

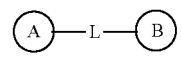

is -M-W—, the -M-W— can be linked to the ring A and the ring B in the same direction as the reading order from left to right to constitute

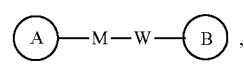, or can be linked to the ring A and the ring B in the reverse direction as the reading order from left to right to constitute

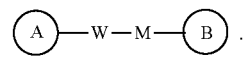.

A combination of the linking groups, substituents and/or variants thereof is allowed only when such combination can result in a stable compound.

Unless otherwise specified, the term "halo" or "halogen" by itself or as part of another substituent represents a fluorine, chlorine, bromine or iodine atom.

Unless otherwise specified, the term "$C_{1-3}$ alkoxy" refers to an alkyl group containing 1 to 3 carbon atoms and attached to the remainder of a molecule by an oxygen atom. The $C_{1-3}$ alkoxy group includes $C_{1-2}$, $C_{2-3}$, $C_3$, $C_2$ alkoxy groups, and the like. Examples of $C_{1-3}$ alkoxy groups include, but are not limited to, methoxy, ethoxy, propoxy (including n-propoxy and isopropoxy), and the like.

Unless otherwise specified, the term "$C_{1-3}$ alkyl" is used to indicate a linear or branched saturated hydrocarbon group consisting of 1 to 3 carbon atoms. The $C_{1-3}$ alkyl group includes $C_{1-2}$ and $C_{2-3}$ alkyl groups and the like. It may be monovalent (e.g., methyl), divalent (e.g., methylene) or multivalent (e.g., methenyl). Examples of $C_{1-3}$ alkyl groups include, but are not limited to, methyl (Me), ethyl (Et), propyl (including n-propyl and isopropyl), and the like.

Unless otherwise specified, the terms "5- to 6-membered heteroaromatic ring" and "5- to 6-membered heteroaryl" may be used interchangeably. The term "5- to 6-membered heteroaryl" means a monocyclic group having a conjugated pi electron system and consisting of 5 to 6 ring atoms, of which 1, 2, 3 or 4 ring atoms are heteroatoms independently selected from O, S and N, and the remainder atoms are carbon atoms, wherein the nitrogen atom is optionally quaternized and the nitrogen and sulfur heteroatoms are optionally oxidized (i.e., NO and $S(O)_p$, p is 1 or 2). The 5- to 6-membered heteroaryl group may be attached to the remainder of a molecule by a heteroatom or a carbon atom. The 5- to 6-membered heteroaryl group includes 5-membered and 6-membered heteroaryl groups. Examples of the 5- to 6-membered heteroaryl group include, but are not limited to, pyrrolyl (including N-pyrrolyl, 2-pyrrolyl, 3-pyrrolyl, and the like), pyrazolyl (including 2-pyrazolyl and 3-pyrazolyl, and the like), imidazolyl (including N-imidazolyl, 2-imidazolyl, 4-imidazolyl, and 5-imidazolyl, and the like), oxazolyl (including 2-oxazolyl, 4-oxazolyl, and 5-oxazolyl, and the like), triazolyl (1H-1,2,3-triazolyl, 2H-1,2,3-triazolyl, 1H-1,2,4-triazolyl and 4H-1,2,4-triazolyl, and the like), tetrazolyl, isoxazolyl (3-isoxazolyl, 4-isoxazolyl and 5-isoxazolyl, and the like), thiazolyl (including 2-thiazolyl, 4-thiazolyl and 5-thiazolyl, and the like), furyl (including 2-furyl and 3-furyl, and the like), thienyl (including 2-thienyl and 3-thienyl, and the like), pyridyl (including 2-pyridyl, 3-pyridyl and 4-pyridyl, and the like), pyrazinyl or pyrimidinyl (including 2-pyrimidinyl and 4-pyrimidinyl, and the like).

Unless otherwise specified, $C_{n-n+m}$ or $C_n$-$C_{n+m}$ includes any one of n to n+m carbons. For example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$. $C_{n-n+m}$ or $C_n$-$C_{n+m}$ also includes any range of n to n+m. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, and the like. Similarly, the n-membered to n+m-membered ring means that the number of atoms on the ring is n to n+m. For example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring. The n-membered to n+m-membered ring also means that the number of atoms on the ring includes any range from n to n+m. For example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1, 1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The structures of compounds disclosed herein can be confirmed by conventional methods well known to those skilled in the art. If the present disclosure relates to an absolute configuration of a compound, the absolute configuration can be confirmed by conventional techniques in the art, such as single crystal X-Ray diffraction (SXRD). In the single crystal X-Ray diffraction (SXRD), the diffraction intensity data of the cultivated single crystal is collected using a Bruker D8 venture diffractometer with a light source of CuKα radiation in a scanning mode of φ/ω scan; after collecting the relevant data, the crystal structure is further analyzed by the direct method (Shelxs97) to confirm the absolute configuration.

Compounds disclosed herein can be prepared by a variety of synthetic methods well known to those skilled in the art, including the following enumerated embodiment, the embodiment formed by the following enumerated embodiment in combination with other chemical synthesis methods, and equivalent replacement well known to those skilled in the art. Alternative embodiments include, but are not limited to the embodiment disclosed herein.

Solvents used in the present disclosure are commercially available.

The following abbreviations are used in the present disclosure: aq represents aqueous; $NaNO_2$ represents sodium nitrate; $H_2SO_4$ represents sulfuric acid; $CuCl_2$ represents copper chloride; $LiOH \cdot H_2O$ represents lithium hydroxide monohydrate; $NaBH_3CN$ represents sodium cyanoborohydride; HCl/EtOAc represents a solution of hydrochloric acid in ethyl acetate; HCl represents hydrochloric acid; $CO_2$ represents carbon dioxide; ACN represents acetonitrile; FA represents formic acid; $H_2O$ represents water; $NH_3H_2O$ represents ammonia; $Na_2SO_4$ represents sodium sulfate; $MgSO_4$ represents magnesium sulfate; NCS represents N-chlorosuccinimide; $NH_4HCO_3$ represents ammonium bicarbonate; Pd/C represents palladium on carbon; psi represents pressure unit; MeCN represents acetonitrile; $TsOH \cdot H_2O$ represents p-toluenesulfonic acid monohydrate; $Pd(dppf)Cl_2$ represents [1,1'-bis(diphenylphosphino)ferrocene]palladium dichloride; Neu represents neutral; HPLC represents high performance liquid chromatography; HATU represents O-(7-azabenzotriazol-1-yl)-N,N,N',N'-tetramethyluronium hexafluorophosphate; $K_2CO_3$ represents potassium carbonate; EDC represents N-(3-dimethylaminopropyl)-N'-ethylcarbodiimide hydrochloride; m-CPBA represents 3-chloroperoxybenzoic acid; eq represents equivalent or equivalence; $T_3P$ represents propylphosphonic anhydride; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butoxycarbonyl, which is an amino protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; $SOCl_2$ represents thionyl chloride; $CS_2$ represents carbon disulfide; TsOH represents p-toluenesulfonic acid; NFSI represents N-fluoro-N-(phenylsulfonyl)benzenesulfonamide; $n-Bu_4NF$ represents tetrabutylammonium fluoride; iPrOH represents 2-propanol; mp represents melting point; LDA represents lithium diisopropylamide; IPAm represents isopropylamine; DIPEA represents N,N-diisopropylethylamine; Xantphos represents 4,5-bis(diphenylphosphino)-9,9-dimethylxanthene; t-Bu Xphos represents 2-di-tert-butylphosphino-2',4',6'-triisopropylbiphenyl; DPPP represents 1,3-bis(diphenylphosphino)propane; $Et_3SiH$ represents triethylsilane; DMAP represents 4-dimethylaminopyridine; Py represents pyridine; DPBS represents Dulbecco's phosphate buffer; TNF-α represents tumor necrosis factor; $IC_{50}$ represents half maximal inhibitory concentration; mg represents milligrams, kg represents kilograms; and HEPES represents N-2-hydroxyethylpiperazine-N-2-ethane sulfonic acid buffer.

Compounds are named according to general naming principles in the art or by ChemDraw® software, and commercially available compounds are named with their vendor directory names.

DETAILED DESCRIPTION OF THE INVENTION

The present disclosure is described in detail below by means of examples. However, it is not intended that these examples have any disadvantageous limitations to the present disclosure. The present disclosure has been described in detail herein, and embodiments are also disclosed herein. It will be apparent to those skilled in the art that various changes and modifications may be made to the embodiments disclosed herein without departing from the spirit and scope disclosed herein.

Reference Example 1: Fragment BB-1

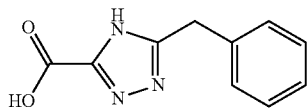 [SMILES: O=C(O)c1nnc(Cc2ccccc2)[nH]1]

Route for Synthesis

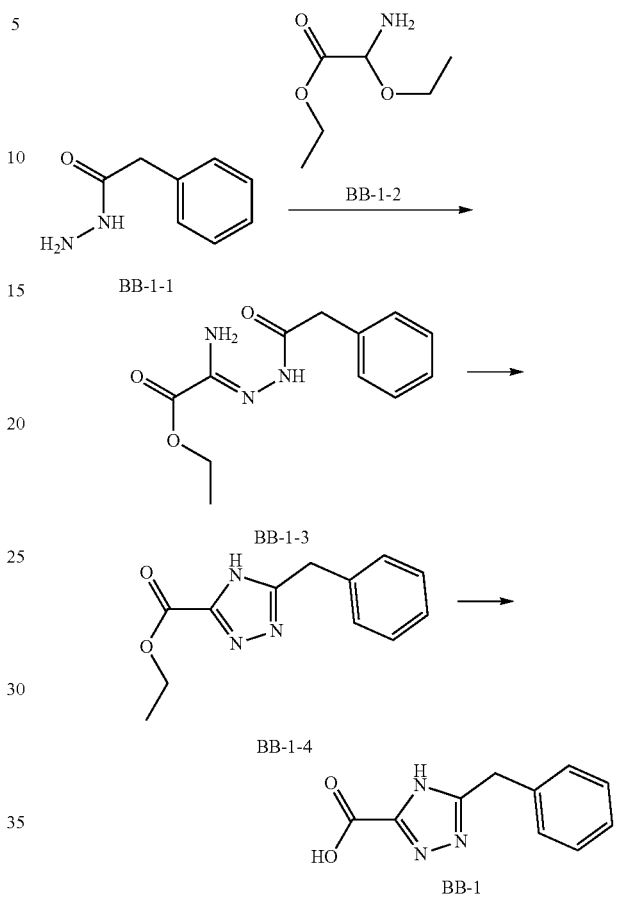

Step 1: Synthesis of Compound BB-1-3

To a pre-dried 100 mL flask were added BB-1-1 (2.60 g, 17.31 mmol, 1.00 eq) and solvent EtOH (11.25 mL) and isopropyl ether (37.50 mL). BB-1-2 (2.59 g, 17.83 mmol, 1.03 eq) was slowly added under stirring, and the reaction solution was stirred at 20° C. for 12 hours. The reaction solution was filtered, and the resulting filter cake was washed with isopropyl ether (30 mL*3) to give compound BB-1-3. $^1H$ NMR (400 MHz, DMSO-$d_6$) δ=9.95 (s, 1H), 9.90 (s, 1H), 7.39-7.08 (m, 6H), 4.21-4.19 (m, 2H), 3.82 (s, 2H), 1.27-1.23 (m, 3H); LCMS m/z=250.1 $[M+H]^+$.

Step 2: Synthesis of Compound BB-1-4

To a pre-dried 250 mL flask were added compound BB-1-3 (7.00 g, 28.08 mmol, 1.00 eq) and xylene (100.00 mL). A Dean-Stark trap was installed. The reaction system was reacted at 180° C. for 10 h, 100 mL of isopropyl ether was added to the reaction system and the mixture was stirred for 30 minutes in an ice-water bath. The reaction system was filtered, and the resulting filter cake was washed with 50 mL of n-hexane to give compound BB-1-4. $^1H$ NMR (400 MHz, DMSO-$d_6$) δ=14.44 (br s, 1H), 7.42-7.14 (m, 4H), 4.29 (q, J=6.5 Hz, 2H), 4.13 (br s, 2H), 1.28 (br t, J=7.0 Hz, 3H); LCMS m/z=232.2 $[M+H]^+$.

Step 3: Synthesis of Compound BB-1

To a thumb bottle were added compound BB-1-4 (4.10 g, 17.73 mmol, 1.00 eq), tetrahydrofuran (1.00 mL) and water (200.00 μL), and lithium hydroxide monohydrate (1.74 g, 41.49 mmol, 2.34 eq) was then added. The solution was stirred at 20° C. for 12 hours. The solvent was removed under reduced pressure, 25 mL of 1N aqueous hydrochloric acid solution was added dropwise with stirring until the pH of the system reached 2. Compound BB-1 was obtained after suction filtration. LCMS m/z=202.1 [M−H]⁻.

Reference Example 2: Fragment BB-2

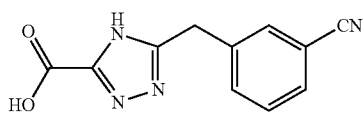 [SMILES: N#Cc1cccc(Cc2nnc(C(=O)O)[nH]2)c1]

Route for Synthesis

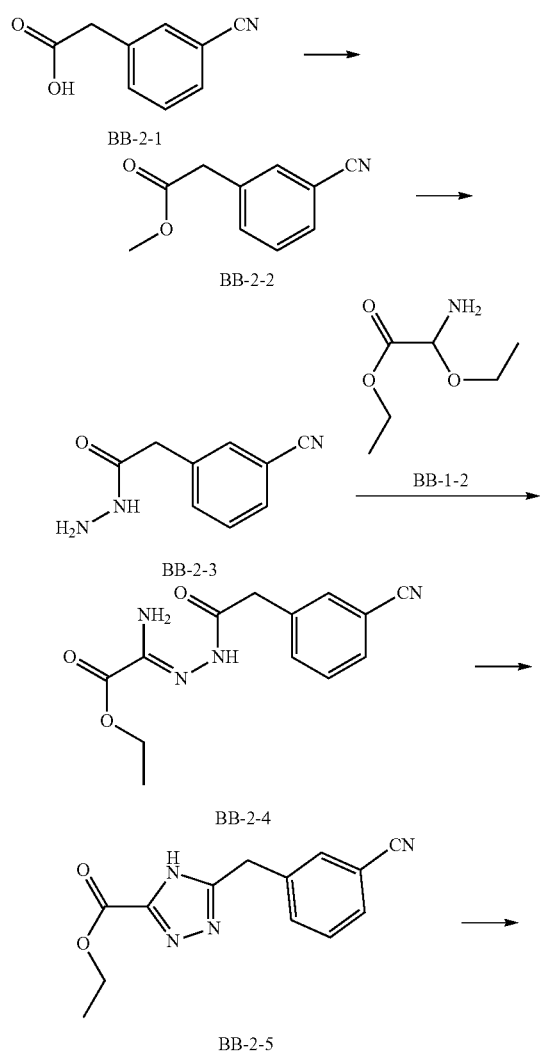

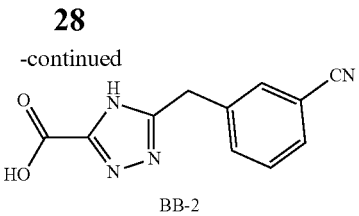

Step 1: Synthesis of Compound BB-2-2

To a solution of BB-2-1 (2.5 g, 15.51 mmol, 2.94 mL, 1 eq) in dichloromethane (40 mL) was added methanol (4.97 g, 155.13 mmol, 6.28 mL, 10 eq) at 23° C. TMSCHN$_2$ (2 M, 9.31 mL, 1.2 eq) was then added and the mixture was stirred for another 2 hours. The raw materials were completely consumed by TLC (petroleum ether:ethyl acetate=5:1) monitoring. 0.1 mL of glacial acetic acid was added to the reaction solution, and the reaction solution was concentrated under reduced pressure to give BB-2-2.

Step 2: Synthesis of Compound BB-2-3

To a solution of BB-2-2 (3 g, 17.12 mmol, 1 eq) in methanol (30 mL) was added hydrazine hydrate (3.21 g, 51.37 mmol, 3.12 mL, 80% purity, 3 eq), and the mixture was then stirred in an oil bath at 70° C. for 2 hours. By LCMS monitoring, the raw materials were completely consumed, and a target signal appeared. The reaction solution was concentrated under reduced pressure to remove the solvent, and 50 mL of ethyl acetate was added. The mixture was washed with 30 mL of saturated brine. The organic phase was dried over anhydrous sodium sulfate, and filtered, and the filtrate was concentrated under reduced pressure to give BB-2-3. $^1$H NMR (400 MHz, DMSO-d$_6$) δ=9.25 (br s, 1H), 7.66-7.74 (m, 2H), 7.45-7.65 (m, 2H), 4.24 (s, 2H), 3.43 (s, 2H); LCMS m/z=176.1 [M+H]⁺.

Step 3: Synthesis of Compound BB-2-4

To a pre-dried three-necked bottle were added BB-1-2 (2.07 g, 14.27 mmol, 1 eq), ethanol (10 mL), and isopropyl ether (20 mL), and BB-2-3 (2.5 g, 14.27 mmol, 1 eq) was then added. The mixture was reacted at 25° C. for 5 hours. By LCMS monitoring, the raw materials were completely consumed, and a target signal appeared. The reaction solution was filtered, and the filter cake was washed with 50 mL petroleum ether to give BB-2-4. LCMS m/z=275.2 [M+H]⁺.

Step 4: Synthesis of Compound BB-2-5

To a microwave tube were added BB-2-4 (0.5 g, 1.82 mmol, 1 eq), molecular sieves (4 Å, 0.05 g) and xylene (15 mL). The microwave tube was sealed and the reaction was stirred in a microwave reactor at 150° C. for 4 hours. A target signal appeared by LCMS monitoring, 30 mL of acetonitrile was added to the reaction solution, and the mixture was filtered. The filtrate was concentrated under reduced pressure to give BB-2-5. LCMS m/z=257.1 [M+H]⁺.

Step 5: Synthesis of Compound BB-2

To a solution of BB-2-5 (1 g, 3.90 mmol, 1 eq) in tetrahydrofuran (50 mL) was added a solution of lithium hydroxide monohydrate (654.96 mg, 15.61 mmol, 4 eq) in water (15 mL) at 21° C., and the mixture was then stirred for another 12 hours. By LCMS monitoring, the raw materials were completely consumed, and a target signal appeared, 15 mL of water was added to the reaction solution, and the mixture was extracted with ethyl acetate (30 mL). The resulting aqueous phase was adjusted to a pH of about 3 with 2N aqueous hydrochloric acid solution, and lyophilized to give BB-2. LCMS m/z=227.0 [M−H]⁻.

Reference Example 3: Fragment BB-3

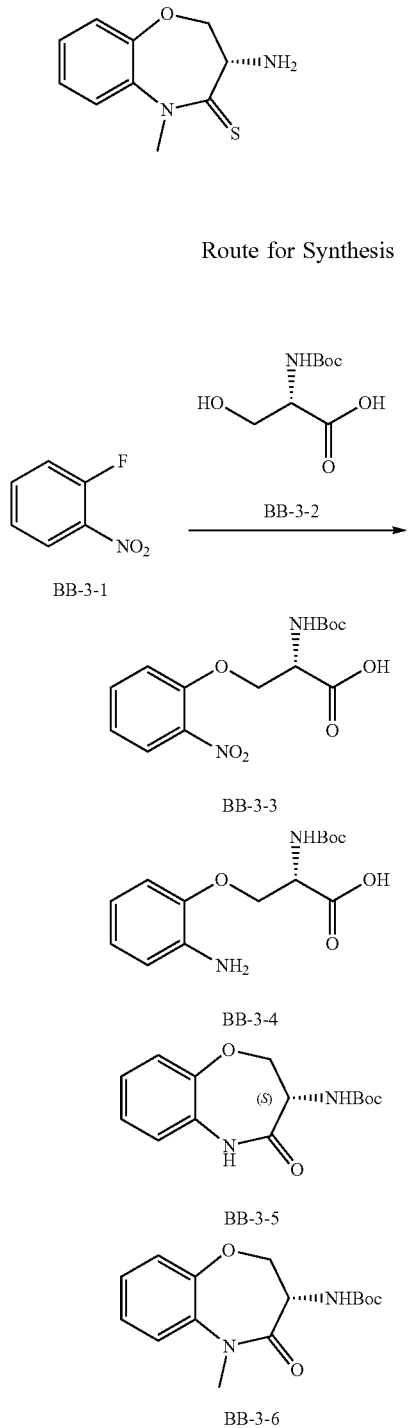

Route for Synthesis

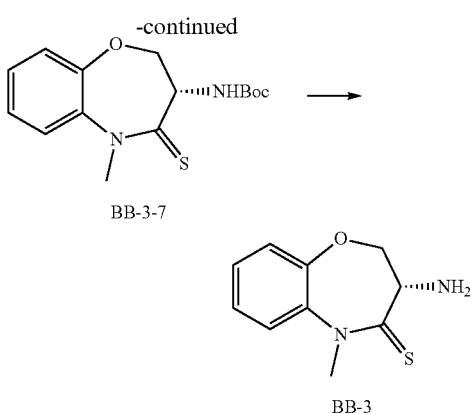

Step 1: Synthesis of Compound BB-3-3

BB-3-2 (20.00 g, 97.46 mmol, 1.00 eq) was dissolved in DMF (50 mL) and the solution was added dropwise to a suspension of NaH (8.19 g, 204.67 mmol, 60% purity, 2.10 eq) in DMF (150 mL). Compound BB-3-1 (13.75 g, 97.46 mmol, 10.26 mL, 1.00 eq) was then added dropwise. The reaction solution was stirred at 20° C. for 16 hours. Ethyl acetate (200 mL) and water (200 mL) were then added to the reaction solution, and the aqueous phase was adjusted to a pH of about 1 with hydrochloric acid. The mixture was extracted with ethyl acetate (200 mL). The organic phase was dried over anhydrous magnesium sulfate, and filtered, and the filtrate was concentrated under reduced pressure to give compound BB-3-3. LCMS m/z=227.1 [M−100+H]⁺.

Step 2: Synthesis of Compound BB-3-4

A solution of compound BB-3-3 (20.00 g, 61.29 mmol, 1.00 eq) and wet Pd/C (5.00 g, 5% purity) in methanol (200.00 mL) was stirred at 20° C. under hydrogen atmosphere (15 psi) for 5 hours. After the completion of the reaction, the reaction solution was filtered, and the filtrate was concentrated under reduced pressure to give compound BB-3-4. LCMS m/z=297.1 [M+H]⁺.

Step 3: Synthesis of Compound BB-3-5

To a solution of compound BB-3-4 (10.00 g, 33.75 mmol, 1.00 eq) and N,N-diisopropylethylamine (4.36 g, 33.75 mmol, 5.89 mL, 1.00 eq) in DMSO (100.00 mL) was added HATU (12.83 g, 33.75 mmol, 1.00 eq). The reaction was stirred at 20° C. for 2 hours. After the completion of the reaction, water (200 mL) and ethyl acetate (200 mL) were added to the reaction solution, and the layers were separated. The organic phase was concentrated under reduced pressure to give a crude product. The crude product was purified by silica gel column chromatography (petroleum ether:ethyl acetate=10:1~1:1) to give compound BB-3-5. LCMS m/z=223.1 [M−56+H]⁺.

Step 4: Synthesis of Compound BB-3-6

To a dry 250 mL three-necked flask were added compound BB-3-5 (6.00 g, 21.56 mmol, 1.00 eq), DMF (60.00 mL) and cesium carbonate (10.54 g, 32.34 mmol, 1.50 eq), and iodomethane (3.06 g, 21.56 mmol, 1.34 mL, 1.00 eq) was then added dropwise. The internal temperature was controlled below 20° C. The reaction was stirred at 16° C.

for 16 hours. After the completion of the reaction, water (100 mL) and ethyl acetate (100 mL) were added to the system, and the layers were separated. The organic phase was washed with saturated brine (100 mL*2), dried over magnesium sulfate, and filtered. The filtrate was concentrated under reduced pressure to give compound BB-3-6. LCMS m/z=237.1 [M−56+H]+.

Step 5: Synthesis of Compound BB-3-7

To a solution of phosphorus pentasulfide (760.35 mg, 3.42 mmol, 363.80 μL, 5 eq) in THF (10 mL) was added sodium carbonate (362.57 mg, 3.42 mmol, 5 eq) at 20° C. and the mixture was stirred for another 0.5 hours. BB-3-6 (0.2 g, 684.16 μmol, 1 eq) was then added, and the reaction solution was placed in an oil bath at 70° C. and stirred for 9.5 hours. A target signal appeared by LCMS monitoring, 20 mL of ethyl acetate was added to the reaction solution, and the mixture was filtered. The resulting filtrate was concentrated under reduced pressure to give compound BB-3-7. LCMS m/z=253.11 [M−56+H]+.

Step 6: Synthesis of Compound BB-3

To BB-3-7 (630.84 mg, 2.05 mmol, 1 eq) was added a solution of hydrochloric acid in ethyl acetate (4 M, 20.00 mL, 39.11 eq), and the mixture was stirred at 23° C. for 1 hour. By LCMS monitoring, the raw materials were completely consumed, and a target signal appeared. The reaction solution was concentrated under reduced pressure to give a crude product, and 30 mL of saturated aqueous sodium bicarbonate solution was then added. The mixture was extracted with ethyl acetate (15 mL*3). The organic phases were combined, dried over anhydrous sodium sulfate, and filtered. The filtrate was concentrated under reduced pressure to give compound BB-3. $^1$H NMR (400 MHz, CDCl$_3$) δ=7.21-7.32 (m, 3H), 7.15-7.19 (m, 1H), 4.40 (dd, =9.92, 6.62 Hz, 1H), 4.10 (dd, J=11.36, 9.81 Hz, 1H), 3.77-3.94 (m, 4H); LCMS m/z=209.1 [M+H]+.

Reference Example 4: Fragment BB-4

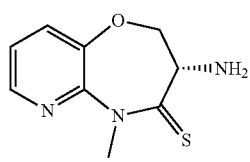

Route for Synthesis

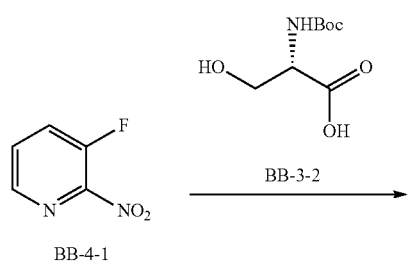

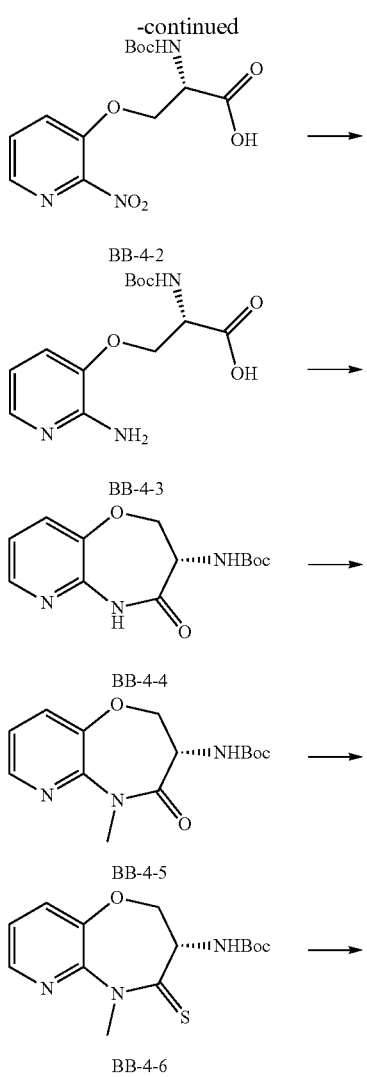

Step 1: Synthesis of Compound BB-4-2

To a solution of BB-3-2 (13.13 g, 63.98 mmol, 1 eq) in DMF (100 mL) was added NaH (5.12 g, 127.96 mmol, 60% purity, 2 eq) at 0° C., and the mixture was stirred for another 1 hour. BB-4-1 (10 g, 70.38 mmol, 1.1 eq) was then added, and the mixture was stirred at 28° C. for 9 hours. A target signal appeared by LCMS monitoring. The reaction solution was added to 1000 mL of water, and the mixture was extracted with ethyl acetate (300 mL*4). The resulting aqueous phase was adjusted to a pH of about 5 with 2N hydrochloric acid, and then extracted with ethyl acetate (300 mL*5). The organic phases were combined, dried over anhydrous sodium sulfate, and filtered. The filtrate was concentrated under reduced pressure to give compound BB-4-2. LCMS m/z=326.0 [M−H]−.

Step 2: Synthesis of Compound BB-4-3

To a solution of BB-4-2 (20.00 g, 61.11 mmol, 1 eq) in methanol (200 mL) was added wet Pd/C (10 g, 30.55 mmol, 5% purity) at 23° C. The mixture was stirred under hydrogen atmosphere (15 psi) for 10 hours. By LCMS monitoring, the raw materials were completely consumed, and a target signal appeared. The reaction solution was filtered, and the resulting filtrate was concentrated under reduced pressure to give compound BB-4-3. LCMS m/z=298.1 [M+H]$^+$.

Step 3: Synthesis of Compound BB-4-4

To a solution of BB-4-3 (16.00 g, 53.82 mmol, 1 eq) in ethyl acetate (400 mL) were added N,N-diisopropylethylamine (20.87 g, 161.45 mmol, 28.12 mL, 3 eq) and 2,4,6-tributyl-1,3,5,2,4,6-trioxatriphosphinane 2,4,6-trioxide (68.49 g, 107.63 mmol, 64.01 mL, 50% purity in ethyl acetate, 2 eq) at 23° C. The mixture was stirred for another 2 hours. By LCMS monitoring, the raw materials were completely consumed, and a target signal appeared. The reaction solution was washed with saturated brine (200 mL*2). The organic phase was dried over anhydrous sodium sulfate, and filtered, and the filtrate was concentrated under reduced pressure to give a crude product. The crude product was purified by silica gel column chromatography (petroleum ether: ethyl acetate=10:1 ~ 1:1) to give compound BB-4-4. LCMS m/z=224.1 [M-56+H]+.

Step 4: Synthesis of Compound BB-4-5

To a solution of BB-4-4 (1 g, 3.58 mmol, 1 eq) in DMF (30 mL) were added cesium carbonate (1.40 g, 4.30 mmol, 1.2 eq) and iodomethane (609.86 mg, 4.30 mmol, 267.48 μL, 1.2 eq) at 20° C. The mixture was stirred for another 1 hour. By LCMS monitoring, the raw materials were completely consumed, and a target signal appeared. The reaction solution was added to 100 mL of water, and the mixture was extracted with ethyl acetate (30 mL*5). The organic phases were combined and washed with 50 mL of saturated brine. The organic phase was dried over anhydrous sodium sulfate, and filtered, and the filtrate was concentrated under reduced pressure to give compound BB-4-5. LCMS m/z=238.1 [M−56+H]$^+$.

Step 5: Synthesis of Compound BB-4-6

To a solution of phosphorus pentasulfide (3.79 g, 17.05 mmol, 10 eq) in THF (30 mL) was added sodium carbonate (1.81 g, 17.05 mmol, 10 eq) at 20° C., and the mixture was stirred for another 0.5 hours. BB-4-5 (0.5 g, 1.70 mmol, 1 eq) was then added, and the reaction solution was placed in an oil bath at 70° C. and stirred for 9.5 hours. The raw materials were substantially consumed by LCMS monitoring, and a target signal appeared. The reaction solution was filtered to give a filtrate, 50 mL of ethyl acetate was added to the filtrate and the mixture was washed with 30 mL of saturated brine. The organic phase was dried over anhydrous sodium sulfate, and filtered, and the filtrate was concentrated under reduced pressure to give a crude product. The crude product was purified by silica gel column chromatography (petroleum ether:ethyl acetate=10:1~1:1) to give compound BB-4-6. LCMS m/z=310.3 [M+H]$^+$.

Step 6: Synthesis of Compound BB-4

To BB-4-6 (0.6 g, 1.94 mmol, 1 eq) was added a solution of hydrochloric acid in ethyl acetate (4 M, 20 mL, 41.25 eq), and the mixture was stirred at 23° C. for 1 hour. By LCMS monitoring, the raw materials were completely consumed, and a target signal appeared. The reaction solution was concentrated under reduced pressure to give a crude product, and 30 mL of saturated sodium bicarbonate solution was added. The mixture was extracted with ethyl acetate (20 mL*3). The organic phases were combined, dried over anhydrous sodium sulfate, and filtered. The filtrate was concentrated under reduced pressure to give compound 3-4. LCMS m/z=210.1 [M+H]$^+$.

Reference Example 5: Fragment BB-5

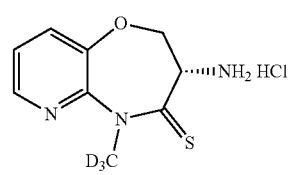

Route for Synthesis

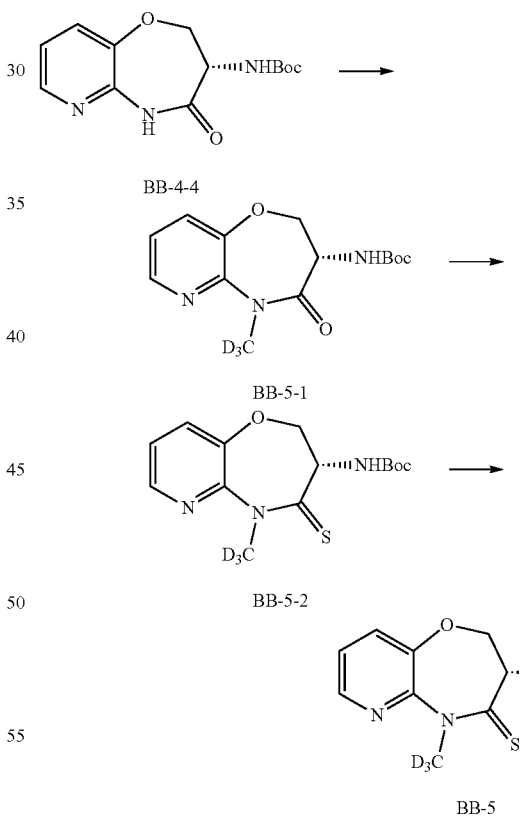

Step 1: Synthesis of Compound BB-5-1

To a solution of BB-4-4 (0.1 g, 358.05 μmol, 1 eq) in tetrahydrofuran (5 mL) were added deuterated iodomethane (101.64 mg, 716.10 μmol, 43.62 μL, 2 eq) and cesium carbonate (349.98 mg, 1.07 mmol, 3 eq) at 25° C., and the mixture was stirred for another 2 hours. Ethyl acetate (20 mL) was added to the reaction solution, and the mixture was then washed with saturated brine (10 mL), and filtered. The filtrate was concentrated under reduced pressure to give a crude product. The crude product was purified by slurrying with methyl tert-butyl ether (5 mL) to give compound BB-5-1. LCMS m/z=297.2 [M+H]+.

Step 2: Synthesis of Compound BB-5-2

To a solution of phosphorus pentasulfide (2.25 g, 10.12 mmol, 1.08 mL, 10 eq) in THF (10 mL) was added sodium carbonate (1.07 g, 10.12 mmol, 10 eq) at 30° C., and the mixture was stirred for 0.5 hours. BB-5-1 (0.3 g, 1.01 mmol, 1 eq) was then added, and the reaction solution was stirred in an oil bath at 70° C. for 10 hours. Ethyl acetate (20 mL) was added to the reaction solution. The mixture was filtered through Celite, and the filtrate was concentrated under reduced pressure to give a crude product. The crude product was purified by column chromatography (petroleum ether:ethyl acetate=10:1~1:1) to give compound BB-5-2. LCMS m/z=312.9 [M+H]+.

Step 3: Synthesis of Compound BB-5

HCl/EtOAc (4 M, 5.69 mL, 59.27 eq) was added to BB-5-2 (0.12 g, 384.12 μmol, 1 eq) at 28° C., and the mixture was stirred for 1 hour. The reaction solution was concentrated under reduced pressure to give compound BB-5. LCMS m/z=213.1 [M+H]+.

Reference Example 6: Fragment BB-6

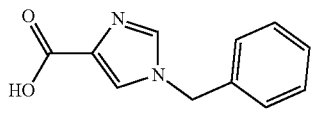

Route for Synthesis

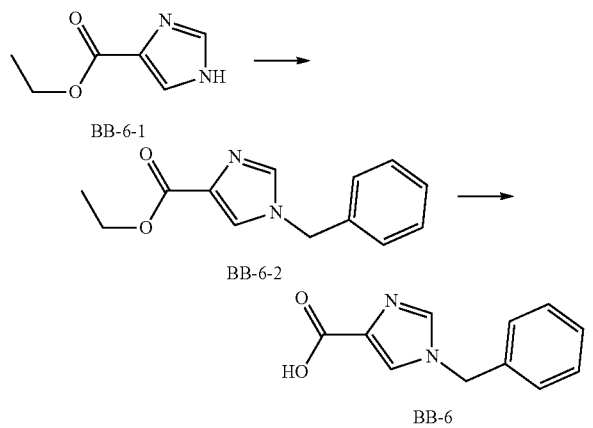

Step 1: Synthesis of Compound BB-6-2

To a solution of BB-6-1 (2 g, 14.27 mmol, 1 eq) and Cs$_2$CO$_3$ (5.11 g, 15.70 mmol, 1.1 eq) in DMF (20 mL) was added benzyl bromide (2.44 g, 14.27 mmol, 1.70 mL, 1 eq) at 25° C., and the mixture was stirred for another 3 hours. By LCMS monitoring, the raw materials were completely consumed, and a target MS appeared. The reaction solution was added to water (100 mL), and the mixture was extracted with ethyl acetate (30 mL*5). The organic phase was dried over anhydrous sodium sulfate, and filtered, and the filtrate was concentrated under reduced pressure. The crude product was purified by flash silica gel column chromatography (petroleum ether:ethyl acetate=10:1~1:1) to give BB-6-2. $^1$H NMR (400 MHz, CDCl$_3$) δ=7.58 (d, J=1.00 Hz, 1H), 7.55 (s, 1H), 7.33-7.40 (m, 3H), 7.14-7.20 (m, 2H), 5.13 (s, 2H), 4.34 (q. J=7.20 Hz, 2H), 1.36 (t, J=7.20 Hz, 3H); LCMS m/z=231.1 [M+1]+.

Step 2: Synthesis of Compound BB-6

To a solution of BB-6-2 (1.50 g, 6.51 mmol, 1 eq) in tetrahydrofuran (26 mL) was added a solution of lithium hydroxide monohydrate (2.19 g, 52.11 mmol, 8 eq) in water (26 mL) at 28° C., and the mixture was stirred for another 12 hours. By LCMS monitoring, the raw materials were completely consumed, and a target MS appeared. The reaction solution was concentrated under reduced pressure. After removing the solvent, water (20 mL) was added, and the mixture was adjusted to a pH of about 2 with 2N hydrochloric acid. The precipitated solid was then filtered to give BB-6. $^1$H NMR (400 MHz, DMSO-d$_6$) δ=7.87 (d, J=2.20 Hz, 2H), 7.27-7.43 (m, 5H), 5.24 (s, 2H); LCMS m/z=201.1 [M−1]−.

Reference Example 7: Fragment BB-7

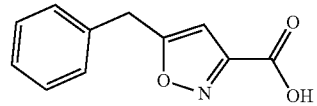 [SMILES: O=C(O)c1cc(Cc2ccccc2)on1]

Route for Synthesis

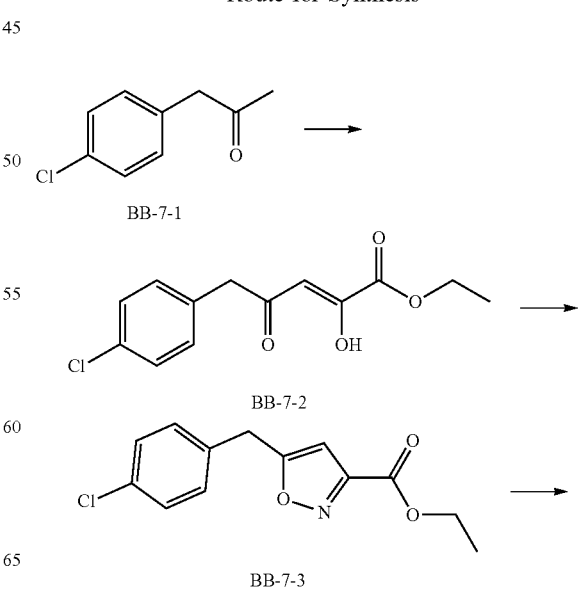

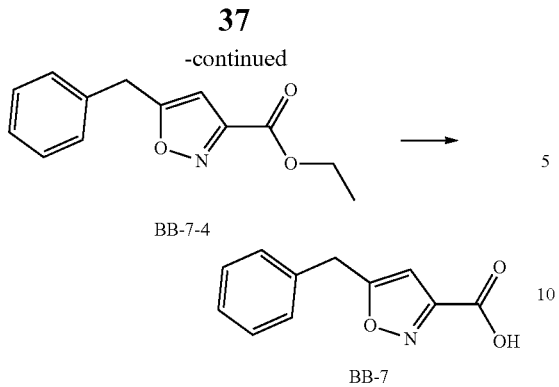

Step 1: Synthesis of Compound BB-7-2

To a solution of BB-7-1 (5 g, 29.65 mmol, 1 eq) in toluene (70 mL) was added diethyl oxalate (4.77 g, 32.62 mmol, 4.45 mL, 1.1 eq) and sodium ethoxide (2.62 g, 38.55 mmol, 1.3 eq) at 0° C., and the mixture was reacted at 20° C. for 12 hours. By LCMS analysis, the raw materials were completely consumed, and a target signal appeared. The reaction solution was concentrated under reduced pressure, diluted with ethyl acetate (200 mL), and washed with saturated brine (200 mL). The organic phase was dried over anhydrous sodium sulfate, and filtered, and the filtrate was concentrated under reduced pressure to give a crude product, which was directly used in the next step without purification. Compound BB-7-2 was obtained. $^1$H NMR (400 MHz, CDCl$_3$) δ=6.87-7.19 (m, 4H), 5.78 (br s, 1H), 4.04 (br s, 2H), 2.92-3.44 (m, 2H), 1.18 (br s, 3H); LCMS m/z=269.1[M+1]$^+$.

Step 2: Synthesis of Compound BB-7-3

To a solution of BB-7-2 (7 g, 26.05 mmol, 1 eq) in ethanol (200 mL) was added hydroxylamine hydrochloride (1.81 g, 26.05 mmol, 1 eq), and the mixture was reacted at 80° C. for 12 hours. By LCMS analysis, the raw materials were completely consumed, and a target signal appeared. The reaction solution was concentrated under reduced pressure to give BB-7-3. $^1$H NMR (400 MHz, CDCl$_3$) δ=7.33 (m, 2H); 7.20 (m, 2H), 6.35 (s, 1H), 4.41-4.47 (m, 2H), 4.13 (q, J=7.20 Hz, 2H), 1.30-1.33 (t, 3H); LCMS m/z=266.1[M+1]$^+$.

Step 3: Synthesis of Compound BB-7-4

To a solution of BB-7-3 (4 g, 15.06 mmol, 1 eq) in ethanol (100 mL) was added Pd/C (4 g, 5% purity), and the mixture was reacted at 30° C. under H$_2$ atmosphere (30 psi) for 12 hours. By LCMS analysis, the raw materials were completely consumed, and a target signal appeared. The reaction solution was filtered through Celite, and the filtrate was concentrated under reduced pressure to give a crude product. The crude product was purified by silica gel column chromatography (dichloromethane:methanol=10:1) to give compound BB-7-4. LCMS m/z=232.1[M+1]$^+$.

Step 4: Synthesis of Compound BB-7

To a solution of BB-7-4 (0.5 g, 2.16 mmol, 1 eq) in tetrahydrofuran (15 mL) and water (5 mL) was added lithium hydroxide monohydrate (453.17 mg, 10.80 mmol, 5 eq), and the mixture was reacted at 30° C. for 2 hours. The raw materials were completely consumed and a new spot appeared by TLC (petroleum ether:ethyl acetate=5:1) monitoring. The reaction solution was concentrated under reduced pressure to remove the organic solvent, and 2 M hydrochloric acid solution was added to adjust pH to about 2. A white solid precipitated. The mixture was filtered, and the filter cake was collected to give BB-7. $^1$H NMR (400 MHz, DMSO-d$_6$) δ=7.24-7.41 (m, 5H), 6.57 (s, 1H), 4.22 (s, 2H).

Reference Example 8: Fragment BB-8

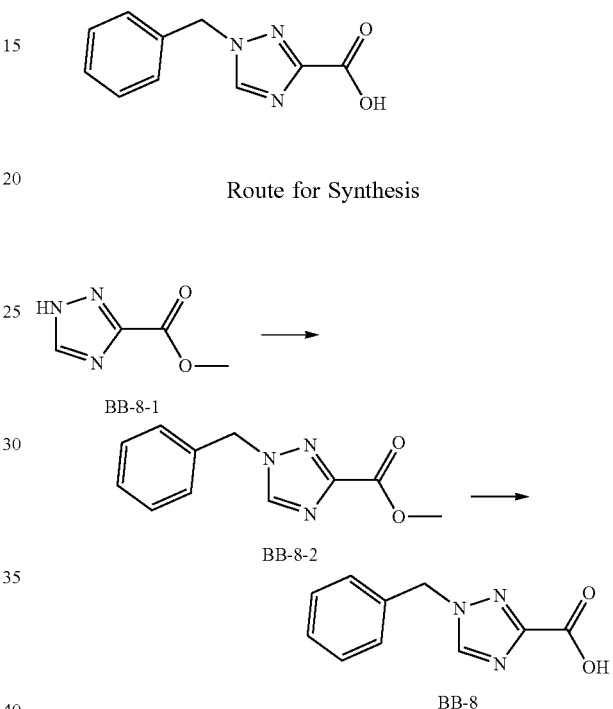

Step 1: Synthesis of Compound BB-8-2

To a solution of BB-8-1 (2 g, 15.74 mmol, 1 eq) in DMF (32 mL) were added cesium carbonate (6.67 g, 20.46 mmol, 1.3 eq) and benzyl bromide (3.23 g, 18.88 mmol, 2.24 mL, 1.2 eq), and the mixture was stirred at 20° C. for 2 hours. By LCMS monitoring, the raw materials were completely consumed, and a target signal appeared. Water (30 mL) and ethyl acetate (30 mL) were added to the reaction solution, and the layers were separated. The organic phase was washed with saturated brine, dried over anhydrous sodium sulfate, and filtered. The filtrate was concentrated under reduced pressure to give a crude product. The crude product was purified by flash silica gel column chromatography (petroleum ether:ethyl acetate=10:1-3:1) to give BB-8-2. $^1$H NMR (400 MHz, CDCl$_3$) δ=8.11 (s, 1H), 7.34-7.43 (m, 3H), 7.27-7.33 (m, 2H), 5.43 (s, 2H), 4.00 (s, 3H); LCMS m/z=218.1 [M+1]$^+$.

Step 2: Synthesis of Compound BB-8

BB-8-2 (0.3 g, 1.38 mmol, 1 eq) was dissolved in tetrahydrofuran (12 mL) and water (4 mL), and lithium hydroxide monohydrate (173.85 mg, 4.14 mmol, 3 eq) was added. The reaction was stirred at 25° C. for 12 hours. By LCMS monitoring, the raw materials were completely consumed, and a target signal peak appeared. Ethyl acetate (10 mL) was added to the reaction solution, and the aqueous phase was adjusted to a pH of 3-4 with 1 M hydrochloric acid. Solid precipitated. The mixture was filtered to give BB-8. $^1$H NMR (400 MHz, DMSO-d$_6$) δ=13.25 (br s, 1H), 8.78 (s, 1H), 7.27-7.40 (m, 5H), 5.47 (s, 2H); LCMS m/z=204.1 [M+1]$^+$.

Reference Example 9: Fragment BB-9

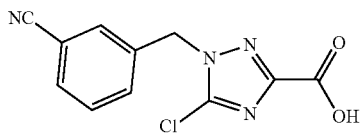 [SMILES: N#Cc1cccc(Cn2nc(C(=O)O)nc2Cl)c1]

Route for Synthesis

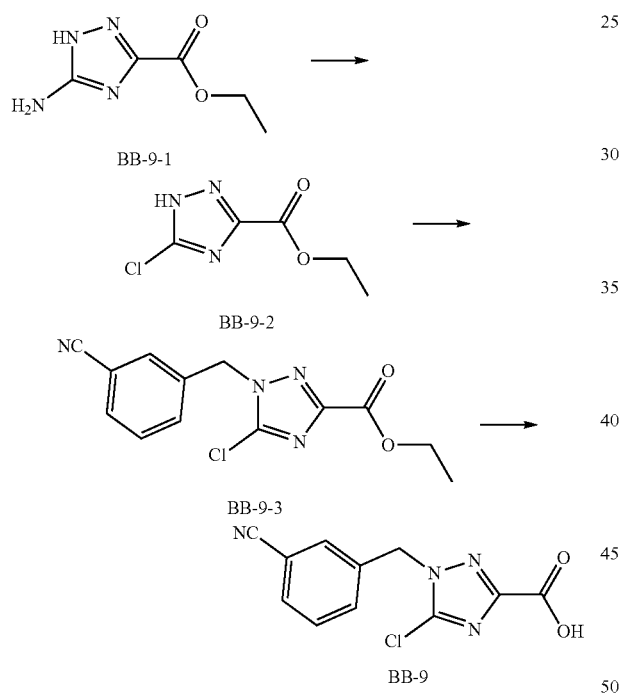

Step 1: Synthesis of Compound BB-9-2

NaNO$_2$ (662.86 mg, 9.60 mmol, 1.5 eq) was added to a solution of BB-9-1 (1 g, 6.40 mmol, 1 eq) in H$_2$SO$_4$ (1 M, 12.80 mL, 2 eq) and water (10 mL) at 0° C., and the mixture was stirred at 0° C. for 0.5 hours. CuCl$_2$ (1.72 g, 12.80 mmol, 2 eq) was dissolved in concentrated hydrochloric acid (15 mL), and the solution was added to the above mixture. The obtained mixture was stirred at 0° C. for 1.5 hours. By LCMS monitoring, the raw materials were completely consumed, and a target signal peak appeared. Ethyl acetate (10 mL) was added to the reaction solution, and the aqueous phase was extracted with ethyl acetate (15 mL*2). The organic phase was washed with saturated brine, dried over anhydrous sodium sulfate, and filtered. The filtrate was concentrated under reduced pressure. The crude product was purified by flash silica gel column chromatography (petroleum ether:ethyl acetate=10:1~1:2) to give BB-9-2. $^1$H NMR (4 (0) MHz, CDCl$_3$) δ=4.46 (q, J=21.60 Hz, 2H), 1.38 (t, J=14.40 Hz, 3H); LCMS m/z=176.0 [M+1]$^+$.

Step 2: Synthesis of Compound BB-9-3

To a solution of BB-9-2 (760.78 mg, 4.33 mmol, 1 eq) in DMF (5 mL) was added cesium carbonate (1.84 g, 5.63 mmol, 1.3 eq) and 3-cyanobenzyl bromide (889.31 mg, 5.20 mmol, 617.58 μL, 1.2 eq), and the reaction was stirred at 20° C. for 2 hours. By LCMS monitoring, the raw materials were completely consumed, and a target signal peak appeared. Water (10 mL) was added to the reaction solution, and the mixture was extracted with ethyl acetate (10 mL*2). The organic phase was washed with saturated brine, dried over anhydrous sodium sulfate, and filtered. The filtrate was concentrated under reduced pressure, and the crude product was purified by flash silica gel column chromatography (petroleum ether:ethyl acetate=20:1~2:1) to give BB-9-3. LCMS m/z=291.0 [M+1]$^+$.

Step 3: Synthesis of Compound BB-9

BB-9-3 (0.08 g, 301.10 μmol, 1 eq) was dissolved in tetrahydrofuran (6 mL) and water (2 mL), and lithium hydroxide monohydrate (37.90 mg, 903.29 μmol, 3 eq) was added. The mixture was reacted at 2° C. for 12 hours. By LCMS monitoring, the raw materials were completely consumed, and a target signal peak appeared. Ethyl acetate (5 mL) was added to the reaction solution. The aqueous phase was adjusted to a pH of about 6 with 1 M hydrochloric acid, and lyophilized to give BB-9. LCMS m/z=263.1 [M+1]$^+$.

Reference Example 10: Fragment BB-10

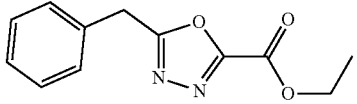 [SMILES: CCOC(=O)c1nnc(Cc2ccccc2)o1]

Route for Synthesis

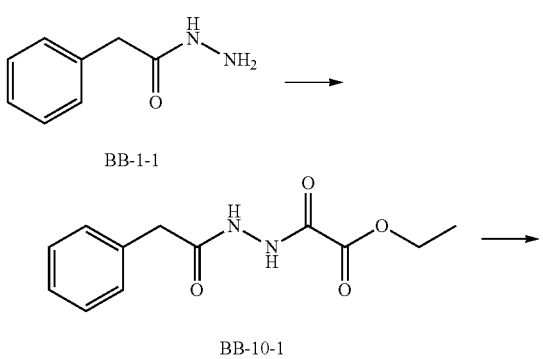

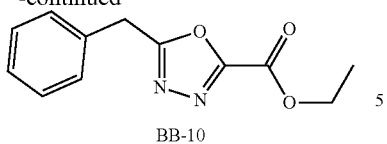

BB-10

Step 1: Synthesis of Compound BB-10-1

To a solution of BB-1-1 (3 g, 19.98 mmol, 1 eq) in dichloromethane (90 mL) was added triethylamine (6.06 g, 59.93 mmol, 8.34 mL, 3 eq). Ethyl chlorooxoacetate (3.55 g, 25.97 mmol, 2.91 mL, 1.3 eq) was added, and the mixture was stirred at 25° C. for 5 hours. By LCMS analysis, the raw materials were completely consumed, and a target signal appeared. The reaction solution was quenched by adding water (60 mL) and extracted with dichloromethane (60 mL*3). The organic phase was dried over anhydrous sodium sulfate, and filtered, and the filtrate was concentrated under reduced pressure. The crude product was purified by flash silica gel column chromatography (petroleum ether:ethyl acetate=5:1-1:1) to give BB-10-1. $^1$H NMR (400 MHz, DMSO-$d_6$) δ=10.73 (br s, 1H), 10.30 (br s, 1H), 7.22-7.34 (m, 5H), 4.26 (q, J=7.00 Hz, 2H), 3.51 (s, 2H), 1.27 (t, J=7.10 Hz, 3H); LCMS m/z=251.1[M+1]$^+$.

Step 2: Synthesis of Compound BB-10

To a solution of BB-10-1 (529.69 mg, 2.12 mmol, 1 eq) in acetonitrile (15 mL) was added phosphorus oxychloride (486.82 mg, 3.17 mmol, 295.04 μL, 1.5 eq). The reaction was stirred at 90° C. for 2 hours. The reaction solution was added to saturated sodium bicarbonate solution (20 mL), and the mixture was stirred vigorously for 5 minutes. The mixture was extracted twice with ethyl acetate (20 mL). The organic phases were combined, washed with saturated brine, dried over anhydrous sodium sulfate, and filtered. The filtrate was concentrated under reduced pressure to give BB-10. $^1$H NMR (400 MHz, CDCl$_3$) δ=7.23-7.10 (m, 5H), 4.36-4.29 (m, 2H), 4.12 (s, 2H), 1.34-1.23 (m, 3H); LCMS m/z=233.1[M+1]$^+$.

Reference Example 11: Fragment BB-11A, BB-11B

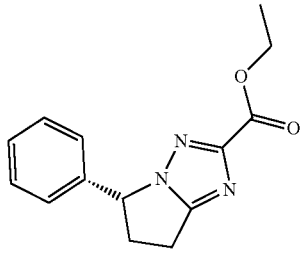

BB-11A

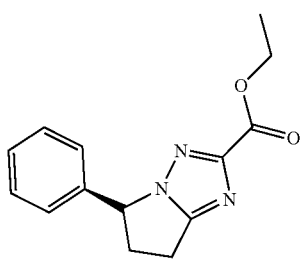

BB-11B

Route for Synthesis

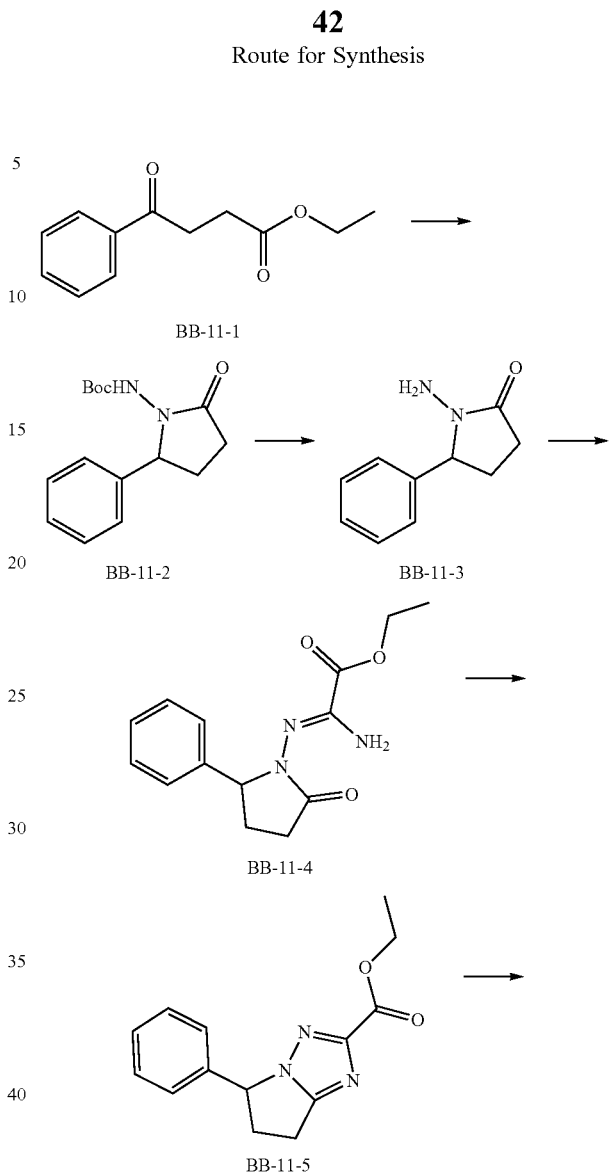

Step 1: Synthesis of Compound BB-11-2

To a solution of BB-11-1 (5 g, 26.01 mmol, 1 eq) in glacial acetic acid (39 mL) and tetrahydrofuran (150 mL) was added tert-butyl carbazate (17.19 g, 130.07 mmol, 5 eq), and the mixture was reacted at 55° C. for 12 hours. The mixture was cooled to room temperature (25° C.), and NaBH$_3$CN (8.17 g, 130.07 mmol, 5 eq) was added in batches. The mixture was heated to 55° C. and reacted for another 12 hours. The reaction solution was cooled to room temperature, and saturated sodium bicarbonate solution was added to the reaction solution to adjust pH to 7-8. The mixture was extracted with ethyl acetate (150 mL*2). The organic phases were combined, washed with saturated brine, dried over anhydrous sodium sulfate, and filtered. The filtrate was concentrated under reduced pressure to give BB-11-2. LCMS m/z=221.1 [M−56+1]$^+$.

Step 2: Synthesis of Compound BB-11-3

11-2 (7 g, 25.33 mmol, 1 eq) was added to HCl/EtOAc (4 M, 60 mL), and the mixture was reacted at 25° C. for 2 hours. The reaction solution was concentrated under reduced pressure to give a crude product. To the crude product was added saturated sodium bicarbonate solution to adjust pH to 7-8. The mixture was extracted with ethyl acetate (50 mL*2). The organic phases were combined, washed with saturated brine, dried over anhydrous sodium sulfate, and filtered. The filtrate was concentrated under reduced pressure to give crude product BB-11-3. LCMS m/z=177.1 [M+1]$^+$.

Step 3: Synthesis of Compound BB-11-4

To a solution of BB-11-3 (4 g, 22.70 mmol, 1 eq) in ethanol (50 mL) was added ethyl 2-ethoxy-2-iminoacetate (16.47 g, 113.50 mmol, 5 eq), and the mixture was reacted at 85° C. for 12 hours. The reaction solution was concentrated under reduced pressure to give a crude product. The crude product was purified by column chromatography (dichloromethane:methanol=10:0 to 5:1) to give BB-11-4. LCMS m/z=276.2 [M+1]$^+$.

Step 4: Synthesis of Compound BB-11-5

BB-11-4 (1.3 g, 4.72 mmol, 1 eq) was added to phosphorous oxychloride (30 mL) at 25° C., and the mixture was reacted at 120° C. for 3 hours. The reaction solution was cooled to room temperature, and then slowly poured into warm water (150 mL). The mixture was adjusted to a pH of 7-8 with saturated sodium bicarbonate, and then extracted with ethyl acetate (100 mL*2). The organic phases were combined, washed with saturated brine, dried over anhydrous sodium sulfate, and filtered. The filtrate was concentrated under reduced pressure to give a crude product. The crude product was purified by column chromatography (dichloromethane:methanol=10:0 to 10:1) to give BB-11-5. $^1$H NMR (400 MHz, DMSO-d$_6$) δ=7.34-7.43 (m, 3H), 7.21-7.28 (m, 2H), 5.58 (br t, J=7.12 Hz, 1H), 4.27 (br dd, J=6.80, 5.04 Hz, 2H), 2.88-3.28 (m, 4H), 1.26 (br t, J=7.12 Hz, 3H), LCMS m/z=258.2 [M+1].

Step 5: Synthesis of Compound BB-11A and BB-11B

The compound BB-11 was analyzed by supercritical fluid chromatography (Chiralcel AD–3 3 μm, 0.46 cm id×15 mL; Mobile phase: A for SFC CO$_2$ and B for MeOH (0.05% IPAm); Gradient: B in A from 10% to 40% in 6 minutes; Flow rate: 4.0 mL/min; Wavelength: 220 nm), and it was shown that retention times of BB-11A and BB-11B were 2.217 min and 2.427 min, respectively, BB-11A and BB-11B were obtained by separation upon supercritical fluid chromatography (Column: DAICEL CHIRALPAK AD (250 mm*50 mm, 10 μm); Mobile phase: [0.1% NH$_3$H$_2$O MEOH]; MeOH %: 30%-30%, 2.56 min). The compound BB-11A was analyzed by supercritical fluid chromatography (Chiralcel AD–3 3 μm, 0.46 cm id×15 mL; Mobile phase: A for supercritical carbon dioxide, B for methanol (containing 0.05% IPAm); Gradient: B from 10% to 40% in 6 minutes; Flow rate: 4.0 mL/min; Wavelength: 220 nm), and it was shown that retention time of BB-11A was 2.235 min, and retention time of BB-11B was 2.439 min.

Reference Example 12: Fragment BB-12

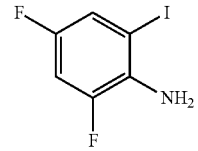

Route for Synthesis

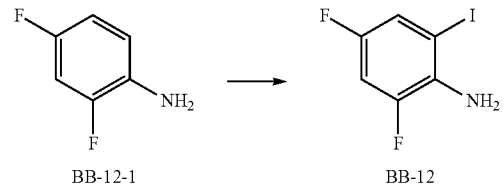

Step 1: Synthesis of Compound BB-12

To a solution of BB-12-1 in ethanol (100 mL) were added I$_2$ (11.40 g, 44.92 mmol, 9.05 mL, 1 eq) and Ag$_2$SO$_4$ (14.01 g, 44.92 mmol, 7.61 mL, 1 eq) at 25° C., and the mixture was stirred for another 12 hours. The reaction solution was filtered through Celite. Water (150 mL) and ethyl acetate (150 mL) were added to the filtrate, and the layers were separated. The aqueous phase was extracted with ethyl acetate (50 mL*2). The organic phases were combined, washed with saturated brine, dried over anhydrous sodium sulfate, and filtered. The filtrate was concentrated under reduced pressure to give a crude product. The crude product was dissolved in ethyl acetate, and hydrochloric acid/ethyl acetate (4 M) was added. The mixture was stirred at room temperature for 0.5 h, and then filtered. The filter cake was collected. Ethyl acetate (50 mL) was added to the cake, and saturated sodium bicarbonate was added to adjust pH to 8~9. The layers were separated. The aqueous phase was extracted with ethyl acetate (25 mL*2). The organic phases were combined, washed with saturated brine, dried over anhydrous sodium sulfate, and filtered. The filtrate was concentrated under reduced pressure (water pump, 45° C.) to give a crude product, and the crude product was purified by column chromatography (petroleum ether:ethyl acetate=10: 1-1:1) to give BB-12. ¹H NMR (400 MHz, CDCl₃) δ=7.22 (dt, J=7.68, 2.37 Hz, 1H), 6.83 (ddd, J=10.85, 8.22, 2.76 Hz, 1H), 3.97 (br s, 2H).

Reference Example 13: Fragment BB-13

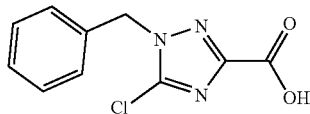 [SMILES: O=C(O)c1nc(Cl)n(Cc2ccccc2)n1]

Route for Synthesis

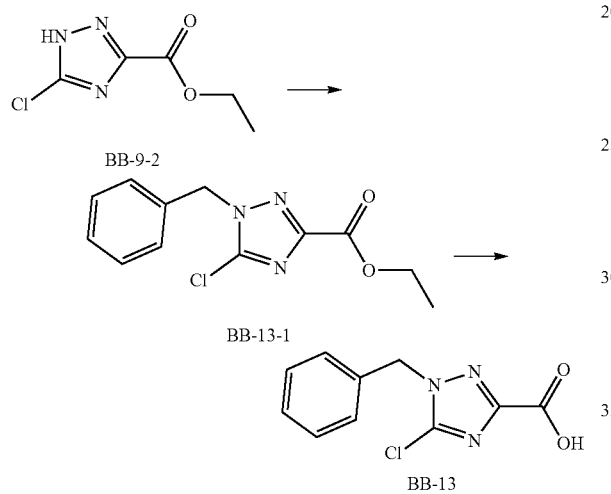

Step 1: Synthesis of Compound BB-13-1

To a solution of BB-9-2 (760.78 mg, 4.33 mmol, 1 eq) in DMF (5 mL) were added cesium carbonate (1.84 g, 5.63 mmol, 1.3 eq) and benzyl bromide (889.31 mg, 5.20 mmol, 617.58 μL, 1.2 eq), and the reaction was stirred at 20° C. for 2 hours. By LCMS monitoring, the raw materials were completely consumed, and a target signal peak appeared. Water (10 mL) was added to the reaction solution, and the mixture was extracted with ethyl acetate (10 mL*2). The organic phase was washed with saturated brine, dried over anhydrous sodium sulfate, and filtered. The filtrate was concentrated under reduced pressure. The crude product was purified by flash silica gel column chromatography (petroleum ether:ethyl acetate=20:1~2:1) to give BB-13-1. ¹H NMR (400 MHz, CDCl₃) δ=7.34-7.41 (m, 3H), 7.29-7.34 (m, 2H), 5.42 (s, 2H), 4.47 (q, J=22.40 Hz, 2H), 1.43 (t, J=15.60 Hz, 3H); LCMS m/z=266.0 [M+1]⁺.

Step 2: Synthesis of Compound BB-13

BB-13-1 (0.08 g, 301.10 μmol, 1 eq) was dissolved in tetrahydrofuran (6 mL) and water (2 mL), and lithium hydroxide monohydrate (37.90 mg, 903.29 μmol, 3 eq) was added. The mixture was reacted at 25° C. for 12 hours. By LCMS monitoring, the raw materials were completely consumed, and a target signal peak appeared, 5 mL of ethyl acetate was added to the reaction solution. The aqueous phase was adjusted to a pH of about 6 with 1 M hydrochloric acid, and lyophilized to give BB-13. ¹H NMR (400 MHz, DMSO-d₆) δ=7.32-7.42 (m, 3H), 7.25-7.30 (m, 2H), 5.48 (s, 2H); LCMS m/z=238.1 [M+1]⁺.

Example 1: WX001

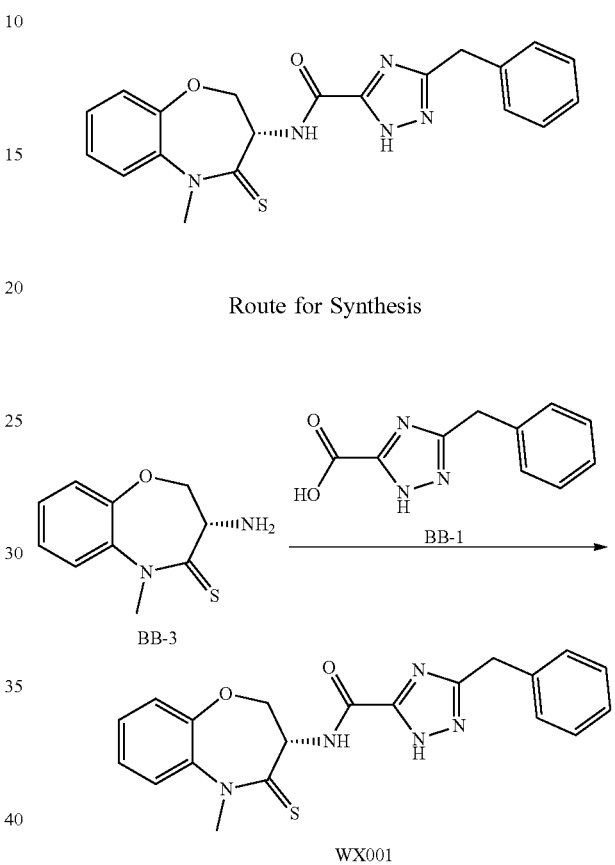

Step 1: Synthesis of Compound WX001

Compound BB-3 (0.58 g, 2.78 mmol, 1 eq), compound BB-1 (849 mg, 4.18 mmol, 1.5 eq), N,N-diisopropylethylamine (1.26 g, 9.75 mmol, 1.70 mL, 3.5 eq) were dissolved in ethyl acetate (10 mL), and then 2,4,6-tributyl-1,3,5,2,4,6-trioxatriphosphinane 2,4,6-trioxide (4.43 g, 6.96 mmol, 4.14 mL, 50% purity in ethyl acetate, 2.5 eq) was added dropwise. After the completion of addition, the mixture was stirred at 25° C. for 12 hours. 20 mL of water was added to the reaction solution and the mixture was extracted with ethyl acetate (5 mL 2). The organic phases were combined and washed with saturated brine (10 mL). The organic phase was dried over anhydrous sodium sulfate, and filtered, and the filtrate was concentrated under reduced pressure to give a crude product. The crude product was purified by silica gel column, and then separated by SFC (Chiralcel OJ-3, 3 μm, 0.46 cm id x 5 cm L; Mobile phase: A for supercritical carbon dioxide, B for methanol (containing 0.05% IPAm); Gradient: B from 10% to 40% in 5 minutes; Flow rate: 4.0 mL/min; Wavelength h: 220 nm) to give compound WX001. 1H NMR (400 MHZ, CDCl3) δ=8.71 (d, J=7.53 Hz, 1H), 7.20-7.38 (m, 9H), 5.15-5.25 (m, 1H), 4.67 (dd, J=6.53, 9.54

Hz, 1H), 4.29 (dd, J=9.79, 10.79 Hz, 1H), 4.21 (s, 2H), 3.89 (s, 3H); LCMS m/z=394.1 [M+H]+. By analyzing with supercritical fluid chromatography (Chiral column: Column: Chiralpak OD-3, 3 μm, 0.46 cm id x 5 cm L; Mobile phase: A: $CO_2$, B: MeOH (0.05% IPAm); Gradient: B/A=10%-40% in 3 minutes; Flow rate: 4.0 mL/min; Wavelength: 220 nm), ee % was equal to 96.36%.

Example 2: WX002

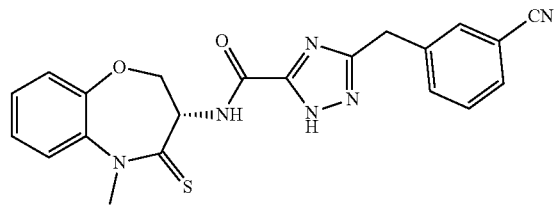 [SMILES: CN1C(=S)[C@@H](NC(=O)c2nc(Cc3cccc(C#N)c3)n[nH]2)COc2ccccc21]

Route for Synthesis

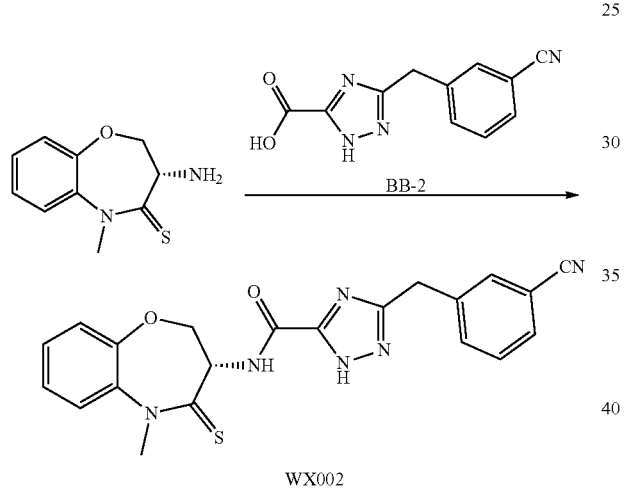

Step 1: Synthesis of Compound WX002

To a solution of BB-3 (0.06 g, 288.07 umol, 1 eq) and BB-2 (131.48 mg, 576.15 umol, 2 eq) in DMF (10 mL) were added 2,4,6-tributyl-1,3,5,2,4,6-trioxatriphosphinane 2,4,6-trioxide (458.30 mg, 720.19 umol, 428.32 μL, 50% purity in ethyl acetate, 2.5 eq) and N,N-diisopropylethylamine (111.69 mg, 864.22 umol, 150.53 μL, 3 eq), and the mixture was stirred at 25° C. for 10 hours. By LCMS monitoring, the raw materials were completely consumed, and a target signal appeared. 20 mL of ethyl acetate was added to the reaction solution and the mixture was washed with 15 mL of saturated brine. The organic phase was dried over anhydrous sodium sulfate, and filtered, and the filtrate was concentrated under reduced pressure to give a crude product. The crude product was purified by preparative HPLC (Column: Xtimate C18 150 mm*25 mm*5 um; Mobile phase: [water (10 mM $NH_4HCO_3$)-ACN]; acetonitrile %: 35%-65%, 10.5 min) to give compound WX002. 1H NMR (400 MHZ, DMSO-$d_6$) δ=8.60 (br d, J=8.16 Hz, 1H), 7.69-7.81 (m, 2H), 7.51-7.65 (m, 3H), 7.36-7.46 (m, 2H), 7.25-7.33 (m, 1H), 4.97 (dt, J=10.58, 7.72 Hz, 1H), 4.35-4.52 (m, 2H), 4.21 (s, 2H), 3.79 (s, 3H); LCMS m/z =419.1 [M+H]+. By analyzing with supercritical fluid chromatography (Chiral column: Column: Chiralpak OD-3, 3 μm, 0.46 cm id x 5 cm L; Mobile phase: A: $CO_2$, B: MeOH (0.05% IPAm); Gradient: B/A=10%-40% in 3 minutes; Flow rate: 4.0 mL/min; Wavelength: 220 nm), ee % was equal to 100%.

Example 3: WX003

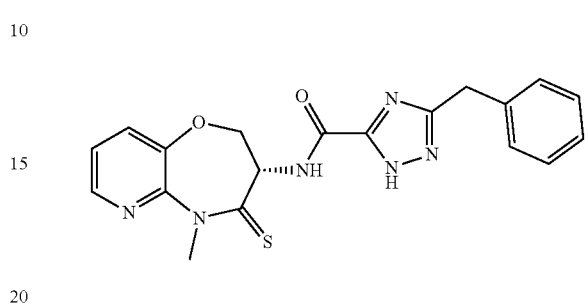

Route for Synthesis

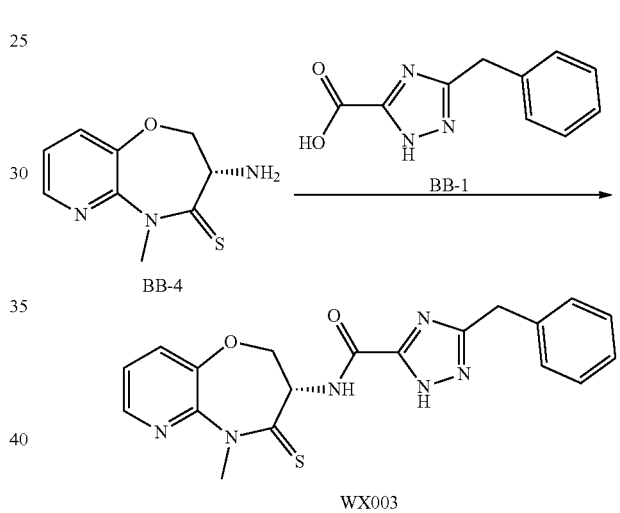

Step 1: Synthesis of Compound WX003

To a solution of BB-4 (60 mg, 286.71 umol, 1 eq) and BB-1 (87.39 mg, 430.07 umol, 1.5 eq) in DMF (10 mL) were added 2,4,6-tributyl-1,3,5,2,4,6-trioxatriphosphinane 2,4,6-trioxide (456.13 mg, 716.78 umol, 426.29 μL, 50% purity in ethyl acetate, 2.5 eq) and N,N-diisopropylethylamine (111.16 mg, 860.13 umol, 149.82 μL, 3 eq), and the mixture was stirred at 25° C. for 10 hours. By LCMS monitoring, the raw materials were completely consumed, and a target signal appeared. 30 mL of ethyl acetate was added to the reaction solution and the mixture was washed with 20 mL of saturated brine. The organic phase was dried over anhydrous sodium sulfate, and filtered, and the filtrate was concentrated under reduced pressure to give a crude product. The crude product was purified by preparative HPLC (Column: Xtimate C18 150 mm*25 mm*5 um; Mobile phase: [water (10 mM $NH_4HCO_3$)-ACN]; acetonitrile %: 35%-65%, 10.5 min) to give compound WX003. $^1$H NMR (400 MHZ, DMSO-$d_6$) δ=8.63 (br s, 1H), 8.46 (dd, J=4.63, 1.54 Hz, 1H), 7.79 (d, J=7.94 Hz, 1H), 7.48 (dd, J=8.05, 4.74 Hz, 1H), 7.23-7.37 (m, 5H), 5.01 (dt, J=10.80, 7.28 Hz, 1H), 4.43-4.72 (m, 2H), 4.14 (br s, 2H), 3.80 (s, 3H); LCMS m/z=395.2 [M+H]+. By analyzing with supercritical fluid chromatography (Chiral column: Column: Chiralpak OD-3, 3 μm, 0.46 cm id x 5 cm L; Mobile phase: A: CO$_2$, B: MeOH (0.05% IPAm); Gradient: B/A=10%-40% in 3 minutes; Flow rate: 4.0 mL/min; Wavelength: 220 nm), ee % was equal to 96.3%.

Example 4: WX004

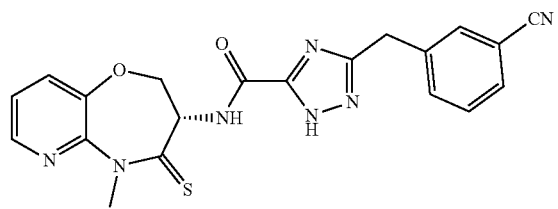

Route for Synthesis

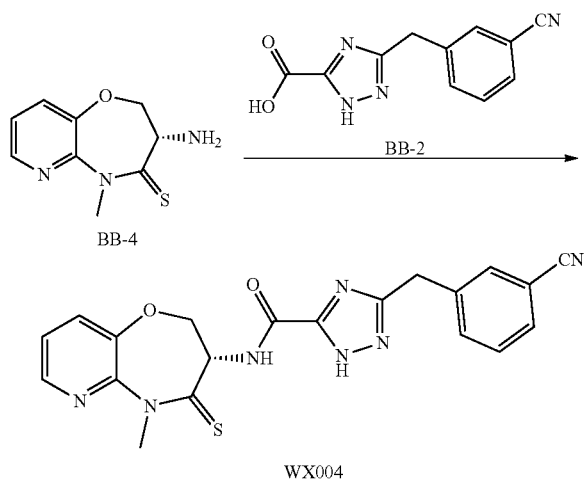

Step 1: Synthesis of Compound WX004

To a solution of BB-4 (60 mg, 286.71 umol, 1 eq) and BB-2 (130.86 mg, 573.43 umol, 2 eq) in DMF (10 mL) were added 2,4,6-tributyl-1,3,5,2,4,6-trioxatriphosphinane 2,4,6-trioxide (456.13 mg, 716.78 μmol, 426.29 μL, 50% purity in ethyl acetate, 2.5 eq) and N,N-diisopropylethylamine (111.16 mg, 860.14 umol, 149.82 μL, 3 eq), and the mixture was stirred at 25° C. for 10 hours. By LCMS monitoring, the raw materials were completely consumed, and a target signal appeared. 30 mL of ethyl acetate was added to the reaction solution and the mixture was washed with 20 mL of saturated brine. The organic phase was dried over anhydrous sodium sulfate, and filtered, and the filtrate was concentrated under reduced pressure to give a crude product. The crude product was purified by preparative HPLC (Column: Xtimate C18 15 mm*25 mm*5 μm; Mobile phase: [water (10 mM NH$_4$HCO$_3$)-ACN]; acetonitrile %: 35%-65%, 10.5 min) to give compound WX004. 1H NMR (400 MHZ, DMSO-d$_6$) δ=8.73 (br s, 1H), 8.46 (d, J=4.85 Hz, 1H), 7.69-7.86 (m, 3H), 7.44-7.65 (m, 3H), 5.01 (dt, J=11.08, 7.14 Hz, 1H), 4.48-4.68 (m, 2H), 4.22 (s, 2H), 3.80 (s, 3H); LCMS m/z=420.1 [M+H]+. By analyzing with supercritical fluid chromatography (Chiral column: Column: Chiralpak OD-3, 3 μm, 0.46 cm id x 5 cm L; Mobile phase: A: CO$_2$, B: MeOH (0.05% IPAm); Gradient: B/A=10%-40% in 3 minutes; Flow rate: 4.0 mL/min; Wavelength: 220 nm), ee % was equal to 100%.

Example 5: WX005

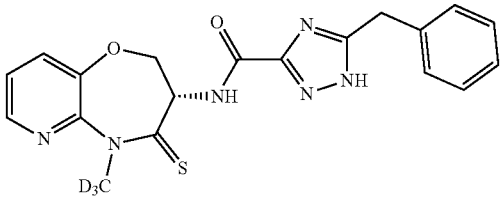 [SMILES: [2H]C([2H])([2H])N1C(=S)[C@@H](NC(=O)c2n[nH]c(Cc3ccccc3)n2)COc2cccnc21]

Route for Synthesis

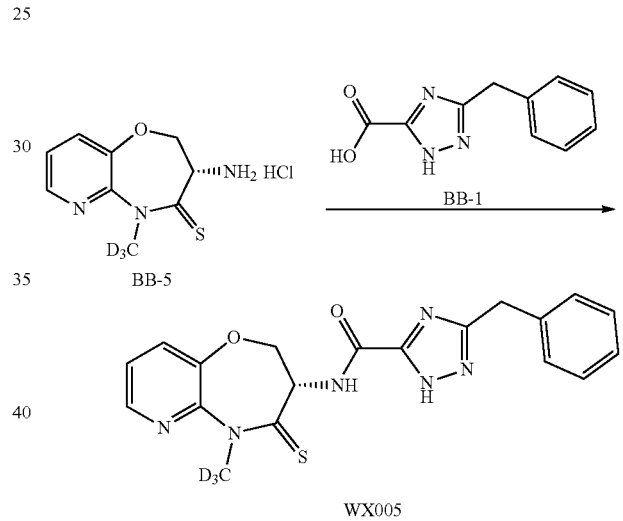

Step 1: Synthesis of Compound WX005

To a solution of BB-5 (100 mg, 471.06 umol, 1 eq) and BB-1 (130.86 mg, 573.43 μmol, 1.2 eq) in DMF (10 mL) were added 2,4,6-tributyl-1,3,5,2,4,6-trioxatriphosphinane 2,4,6-trioxide (599.53 mg, 942.12 μmol, 560.31 μL, 50% purity in ethyl acetate, 2.5 eq) and N,N-diisopropylethylamine (182.64 mg, 1.41 mmol, 246.15 μL, 3 eq), and the mixture was stirred at 25° C. for 10 hours. By LCMS monitoring, the raw materials were completely consumed, and a target signal appeared. Ethyl acetate (30 mL) was added to the reaction solution, and the mixture was washed with saturated brine (20 mL). The organic phase was dried over anhydrous sodium sulfate, and filtered, and the filtrate was concentrated under reduced pressure to give a crude product. The crude product was purified by preparative HPLC (Column: Phenomenex Luna C18 150 mm*30 mm*5 um; Mobile phase: [water (0.05% HCl)-ACN]; acetonitrile %: 20%- 50%, 12 min) to give compound WX005. $^1$H NMR (400 MHZ, DMSO-d6) δ=8.62 (br s, 1H), 8.46 (dd, J=1.75, 4.82 Hz, 1H), 7.79 (dd, J=1.32, 7.89 Hz, 1H), 7.48 (dd, J=4.82, 7.89 Hz, 1H), 7.20-7.37 (m, 5H), 5.01 (td, J=7.34, 11.18 Hz, 1H), 4.60 (br s, 1H), 4.49-4.55 (m, 1H), 4.14 (br s, 2H); LCMS m/z=398.2 [M+H]+. By analyzing with supercritical fluid chromatography (Chiral column: Column: Chiralpak OD-3, 3 μm, 0.46 cm id x 5 cm L; Mobile phase: A: CO$_2$, B: MeOH (0.05% IPAm); Gradient: B/A=10%-40% in 3 minutes; Flow rate: 4.0 mL/min; Wavelength: 220 nm), ee % was equal to 100%.

Example 6: WX006

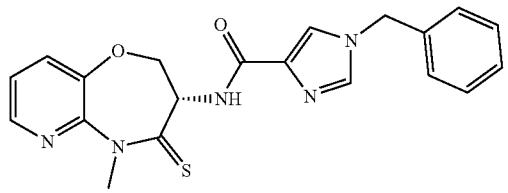 [SMILES: CN1C(=S)[C@@H](NC(=O)c2cn(Cc3ccccc3)cn2)COc2cccnc21]

Route for Synthesis

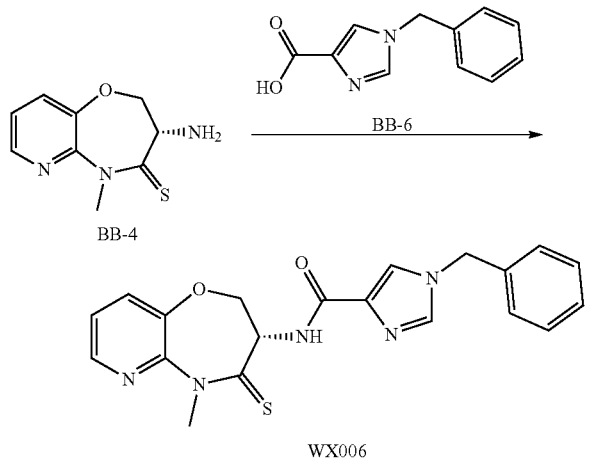

Step 1: Synthesis of Compound WX006

To a solution of BB-4 (10 mg, 47.79 μmol, 1 eq) and BB-1 (11.60 mg, 57.34 μmol, 1.2 eq) in DMF (1 mL) were added 2,4,6-tributyl-1,3,5,2,4,6-trioxatriphosphinane 2,4,6-trioxide (60.82 mg, 95.57 μmol, 56.84 μL, 50% purity in ethyl acetate, 2.5 eq) and N,N-diisopropylethylamine (18.53 mg, 143.36 μmol, 24.97 μL, 3 eq), and the mixture was stirred at 25° C. for 10 hours. By LCMS monitoring, the raw materials were completely consumed, and a target signal appeared. The reaction solution was directly purified by preparative HPLC (Column: Phenomenex Luna C18 150 mm*30 mm*5 um; Mobile phase: [water (0.05% HCl)-ACN]; acetonitrile %: 20%- 50%, 12 min) to give compound WX006. $^1$H NMR (400 MHZ, CDCl3) δ=9.01 (br s, 1H), 8.34-8.46 (m, 2H), 7.51-7.64 (m, 2H), 7.43 (br s, 3H), 7.28-7.31 (m, 2H), 7.22-7.26 (m, 1H), 5.29 (br s, 2H), 5.20 (br d, J=7.02 Hz, 1H), 4.58-4.69 (m, 2H), 3.91 (s, 3H); LCMS m/z=394.2 [M+H]+. By analyzing with supercritical fluid chromatography (Chiral column: Column: Chiralpak OD-3, 3 μm, 0.46 cm id x 5 cm L; Mobile phase: A: CO$_2$, B: MeOH (0.05% IPAm); Gradient: B/A=10%-40% in 3 minutes; Flow rate: 4.0 mL/min; Wavelength: 220 nm), ee % was equal to 100%.

Example 7: WX007

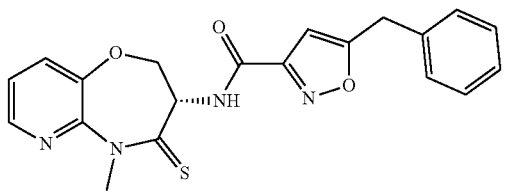 [SMILES: CN1C(=S)[C@@H](NC(=O)c2cc(Cc3ccccc3)on2)COc2cccnc21]

Route for Synthesis

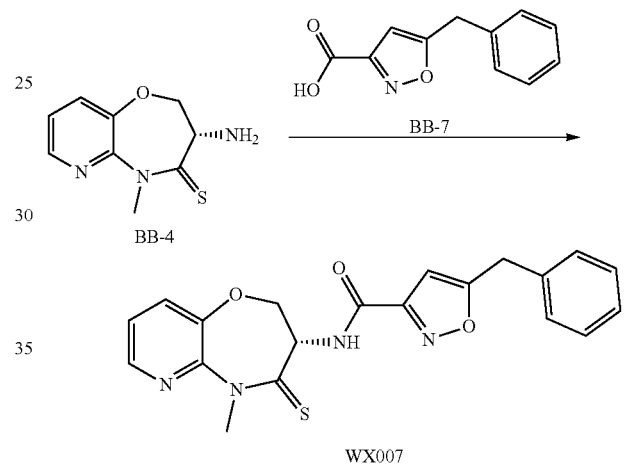

Step 1: Synthesis of Compound WX007

To a solution of BB-4 (10 mg, 47.79 μmol, 1 eq) and BB-7 (11.65 mg, 57.35 μmol, 1.2 eq) in DMF (1 mL) were added 2,4,6-tributyl-1,3,5,2,4,6-trioxatriphosphinane 2,4,6-trioxide (60.82 mg, 95.57 μmol, 56.84 μL, 50% purity in ethyl acetate, 2.5 eq) and N,N-diisopropylethylamine (18.53 mg, 143.36 μmol, 24.97 μL, 3 eq), and the mixture was stirred at 25° C. for 10 hours. By LCMS monitoring, the raw materials were completely consumed, and a target signal appeared. The reaction solution was directly purified by preparative HPLC (Column: Phenomenex Luna C18 150 mm*30 mm*5 um; Mobile phase: [water (0.05% HCl)-ACN]; acetonitrile %: 20%- 50%, 12 min) to give compound WX007. $^1$H NMR (400 MHZ, DMSO-d6) δ=8.98 (d, J=8.33 Hz, 1H), 8.46 (dd, J=1.32, 4.82 Hz, 1H), 7.77 (dd, J=1.75, 7.89 Hz, 1H), 7.47 (dd, J=4.60, 8.11 Hz, 1H), 7.22-7.40 (m, 5H), 6.54 (s, 1H), 5.00 (td, J=7.45, 11.40 Hz, 1H), 4.59-4.70 (m, 1H), 4.48-4.56 (m, 1H), 4.22 (s, 2H), 3.79 (s, 3H); LCMS m/z=395.1 [M+H]+. By analyzing with supercritical fluid chromatography (Chiral column: Column: Chiralpak OD-3, 3 μm, 0.46 cm id x 5 cm L; Mobile phase: A: CO$_2$, B: MeOH (0.05% IPAm); Gradient: B/A=10%-40% in 3 minutes; Flow rate: 4.0 mL/min; Wavelength: 220 nm), ee % was equal to 100%.

53
Example 8: WX008

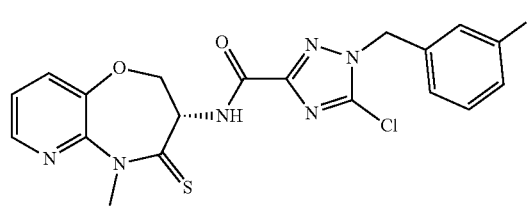

Route for Synthesis

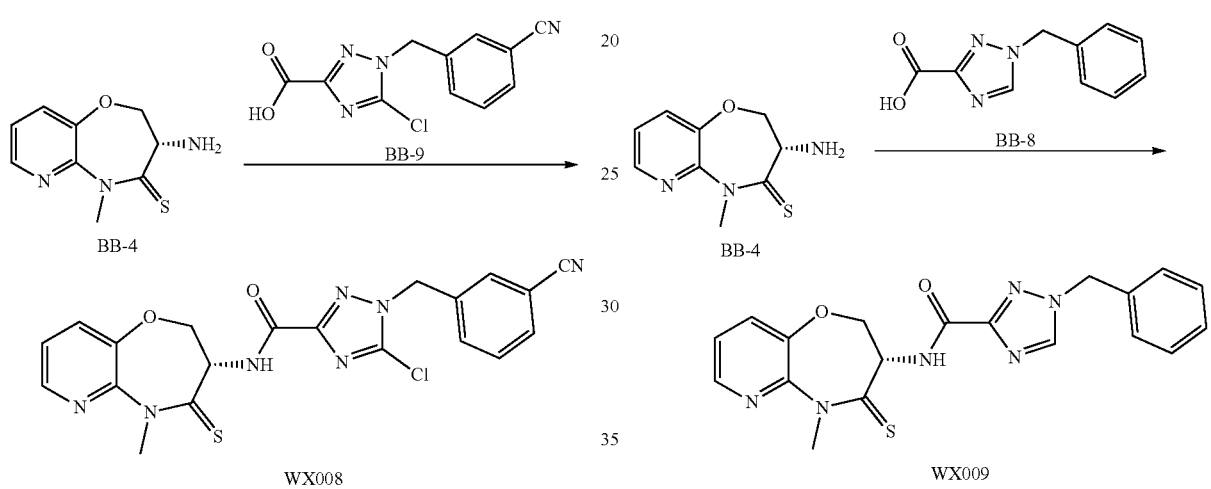

Step 1: Synthesis of Compound WX008

To a solution of BB-4 (10 mg, 47.79 μmol, 1 eq) and BB-8 (15.06 mg, 57.35 μmol, 1.2 eq) in DMF (1 mL) were added 2,4,6-tributyl-1,3,5,2,4,6-trioxatriphosphinane 2,4,6-trioxide (60.82 mg, 95.57 μmol, 56.84 μL, 50% purity in ethyl acetate, 2.5 eq) and N,N-diisopropylethylamine (18.53 mg, 143.36 μmol, 24.97 μL, 3 eq), and the mixture was stirred at 25° C. for 10 hours. By LCMS monitoring, the raw materials were completely consumed, and a target signal appeared. The reaction solution was directly purified by preparative HPLC (Column: Phenomenex Luna C18 150 mm*30 mm*5 um; Mobile phase: [water (0.05% HCl)-ACN]; acetonitrile %: 20%- 50%, 12 min) to give compound WX008. $^1$H NMR (400 MHZ, DMSO-d6) δ=8.85 (d, J=7.89 Hz, 1H), 8.46 (d, J=3.07 Hz, 1H), 7.75-7.89 (m, 3H), 7.61 (d, J=4.82 Hz, 2H), 7.48 (dd, J=4.82, 7.89 Hz, 1H), 5.58 (s, 2H), 4.94-5.06 (m, 1H), 4.65 (t, J=10.74 Hz, 1H), 4.45-4.57 (m, 1H), 3.80 (s, 3H); LCMS m/z=454.1 [M+H]+. By analyzing with supercritical fluid chromatography (Chiral column: Column: Chiralpak OD-3, 3 μm, 0.46 cm id x 5 cm L; Mobile phase: A: CO$_2$, B: MeOH (0.05% IPAm); Gradient: B/A=10%-40% in 3 minutes; Flow rate: 4.0 mL/min; Wavelength: 220 nm), ee % was equal to 100%.

54
Example 9: WX009

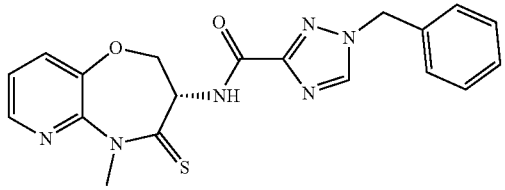 [SMILES: CN1C(=S)[C@@H](NC(=O)c2ncn(Cc3ccccc3)n2)COc2cccnc21]

Route for Synthesis

Step 1: Synthesis of Compound WX009

To a solution of BB-4 (10 mg, 47.79 μmol, 1 eq) and BB-9 (11.65 mg, 57.35 μmol, 1.2 eq) in DMF (1 mL) were added 2,4,6-tributyl-1,3,5,2,4,6-trioxatriphosphinane 2,4,6-trioxide (60.82 mg, 95.57 μmol, 56.84 μL, 50% purity in ethyl acetate, 2.5 eq) and N,N-diisopropylethylamine (18.53 mg, 143.36 μmol, 24.97 μL, 3 eq), and the mixture was stirred at 25° C. for 10 hours. By LCMS monitoring, the raw materials were completely consumed, and a target signal appeared. The reaction solution was directly purified by preparative HPLC (Column: Phenomenex Luna C18 150 mm*30 mm*5 um; Mobile phase: [water (0.05% HCl)-ACN]; acetonitrile %: 20%- 50%, 12 min) to give compound WX009. $^1$H NMR (400 MHZ, DMSO-d6) δ=8.84 (s, 1H), 8.71 (d, J=7.89 Hz, 1H), 8.46 (dd, J=1.53, 4.60 Hz, 1H), 7.79 (dd, J=1.53, 8.11 Hz, 1H), 7.48 (dd, J=4.82, 7.89 Hz, 1H), 7.26-7.42 (m, 5H), 5.49 (s, 2H), 4.94-5.08 (m, 1H), 4.48-4.63 (m, 2H), 3.80 (s, 3H); LCMS m/z=395.1 [M+H]+. By analyzing with supercritical fluid chromatography (Chiral column: Column: Chiralpak OD-3, 3 μm, 0.46 cm id x 5 cm L; Mobile phase: A: CO$_2$, B: MeOH (0.05% IPAm); Gradient: B/A=10%-40% in 3 minutes; Flow rate: 4.0 mL/min; Wavelength: 220 nm), ee % was equal to 100%.

Example 10: WX010

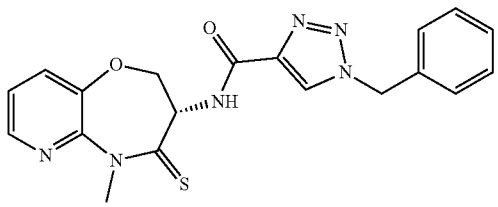 [SMILES: CN1C(=S)[C@@H](NC(=O)c2cn(Cc3ccccc3)nn2)COc2cccnc21]

Route for Synthesis

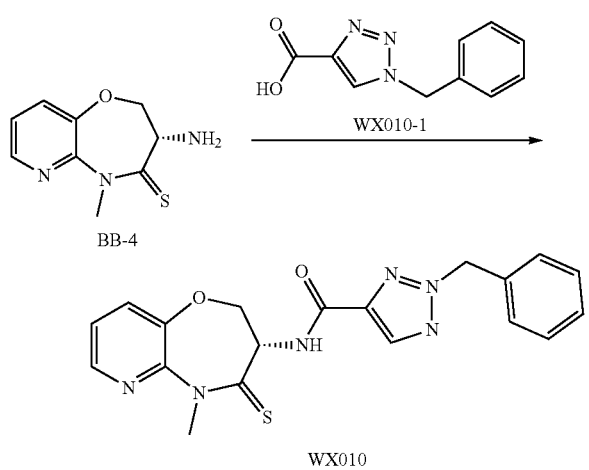

Step 1: Synthesis of Compound WX010

To a solution of BB-4 (10 mg, 47.79 μmol, 1 eq) and WX010-1 (11.65 mg, 57.35 μmol, 1.2 eq) in DMF (1 mL) were added 2,4,6-tributyl-1,3,5,2,4,6-trioxatriphosphinane 2,4,6-trioxide (60.82 mg, 95.57 μmol, 56.84 μL, 50% purity in ethyl acetate, 2.5 eq) and N,N-diisopropylethylamine (18.53 mg, 143.36 μmol, 24.97 μL, 3 eq), and the mixture was stirred at 25° C. for 10 hours. By LCMS monitoring, the raw materials were completely consumed, and a target signal appeared. The reaction solution was directly purified by preparative HPLC (Column: Phenomenex Luna C18 150 mm*30 mm*5 um; Mobile phase: [water (0.05% HCl)-ACN]; acetonitrile %: 20%- 50%, 12 min) to give compound WX010. $^1$H NMR (400 MHZ, DMSO-d6) δ=8.75 (d, J=8.33 Hz, 1H), 8.69 (s, 1H), 8.46 (dd, J=1.53, 4.60 Hz, 1H), 7.79 (dd, J=1.53, 8.11 Hz, 1H), 7.48 (dd, J=4.82, 7.89 Hz, 1H), 7.30-7.41 (m, 5H), 5.65 (s, 2H), 4.97-5.10 (m, 1H), 4.58-4.68 (m, 1H), 4.47-4.57 (m, 1H), 3.80 (s, 3H); LCMS m/z=395.1 [M+H]+. By analyzing with supercritical fluid chromatography (Chiral column: Column: Chiralpak OD-3, 3 μm, 0.46 cm id x 5 cm L; Mobile phase: A: $CO_2$, B: MeOH (0.05% IPAm); Gradient: B/A=10%-40% in 3 minutes; Flow rate: 4.0 mL/min; Wavelength: 220 nm), ee % was equal to 100%.

Example 11: WX011

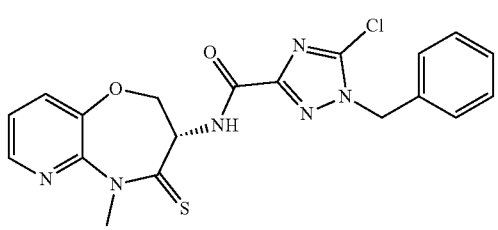 [SMILES: CN1C(=S)[C@@H](NC(=O)c2nc(Cl)n(Cc3ccccc3)n2)COc2cccnc21]

Route for Synthesis

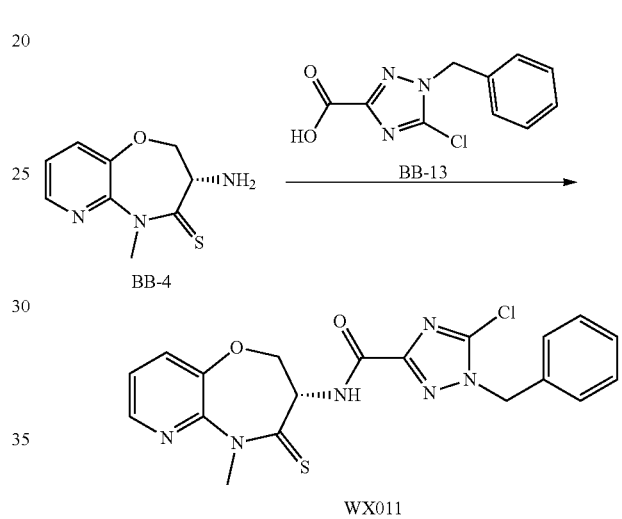

Step 1: Synthesis of Compound WX011

To a solution of BB-4 (10 mg, 47.79 μmol, 1 eq) and BB-13 (14.76 mg, 62.13 μmol, 1.2 eq) in DMF (1 mL) were added 2,4,6-tributyl-1,3,5,2,4,6-trioxatriphosphinane 2,4,6-trioxide (60.82 mg, 95.57 μmol, 56.84 μL, 50% purity in ethyl acetate, 2.5 eq) and N,N-diisopropylethylamine (18.53 mg, 143.36 μmol, 24.97 μL, 3 eq), and the mixture was stirred at 25° C. for 10 hours. By LCMS monitoring, the raw materials were completely consumed, and a target signal appeared. The reaction solution was directly purified by preparative HPLC (Column: Phenomenex Luna C18 150 mm*30 mm*5 um; Mobile phase: [water (0.05% HCl)-ACN]; acetonitrile %: 20%- 50%, 12 min) to give compound WX011. $^1$H NMR (400 MHZ, DMSO-d6) δ=8.83 (d, J=7.89 Hz, 1H), 8.41-8.49 (m, 1H), 7.77 (dd, J=1.32, 7.89 Hz, 1H), 7.46 (dd, J=4.82, 7.89 Hz, 1H), 7.30-7.42 (m, 3H), 7.26 (d, J=7.02 Hz, 2H), 5.48 (s, 2H), 4.98 (td, J=7.13, 11.62 Hz, 1H), 4.59-4.67 (m, 1H), 4.49 (dd, J=6.80, 9.87 Hz, 1H), 3.78 (s, 3H); LCMS m/z=429.0 [M+H]+. By analyzing with supercritical fluid chromatography (Chiral column: Column: Chiralpak OD-3, 3 μm, 0.46 cm id x 5 cm L; Mobile phase: A: $CO_2$, B: MeOH (0.05% IPAm); Gradient: B/A=10%-40% in 3 minutes; Flow rate: 4.0 mL/min; Wavelength: 220 nm), ee % was equal to 100%.

Example 12: WX012

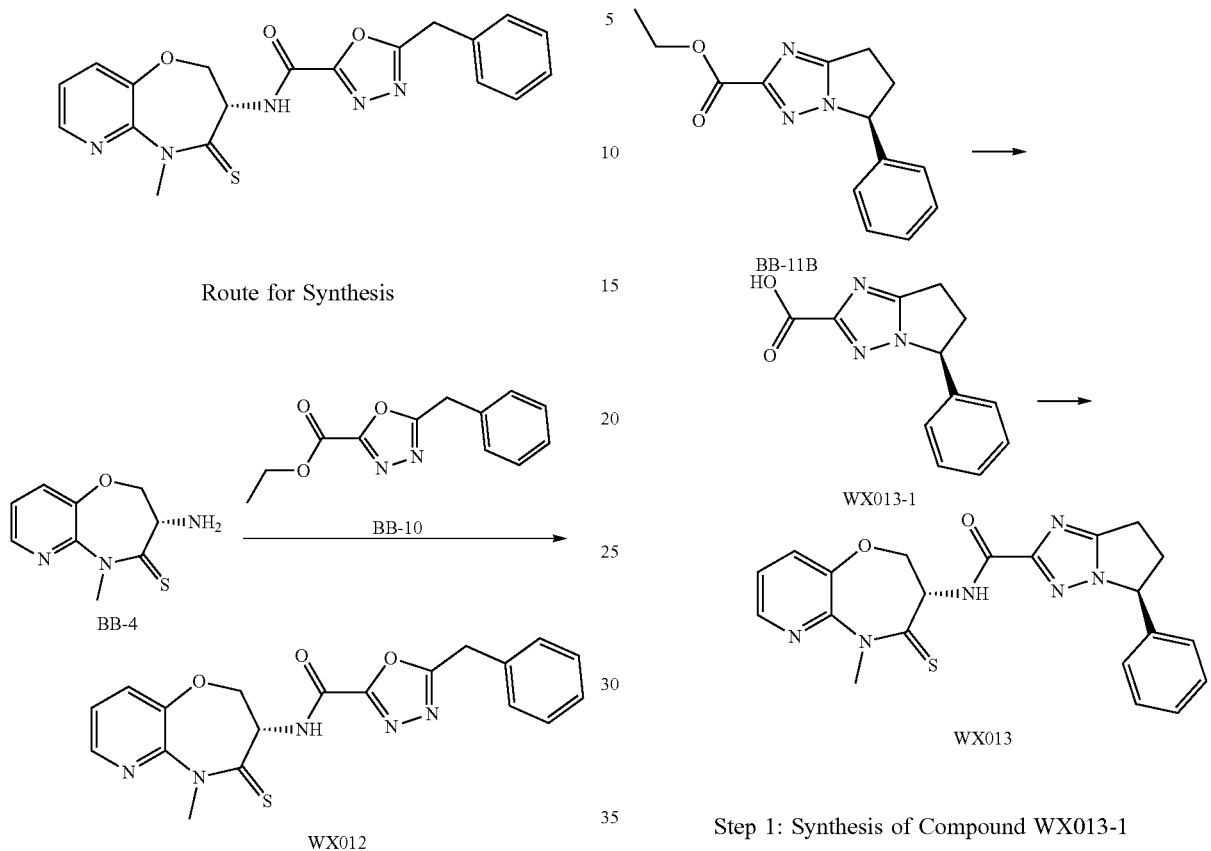

Step 1: Synthesis of Compound WX012

To a solution of BB-4 (15 mg, 71.68 μmol, 1 eq) and BB-10 (33.29 mg, 143.36 μmol, 2 eq) in toluene (3 mL) was added trimethyl aluminum (2 M, 53.76 μL, 1.5 eq), and the mixture was then stirred at 25° C. for 1 hour. By LCMS monitoring, the raw materials were completely consumed, and a target signal appeared. The reaction solution was directly purified by preparative HPLC (Column: Phenome Luna C18 150 mm*30 mm*5 μm; Mobile phase: [water (0.05% HCl)-ACN]; acetonitrile %: 20%-50%, 12 min) to give compound WX012. LCMS m/z=396.2 [M+H]$^+$.

Example 13: WX013

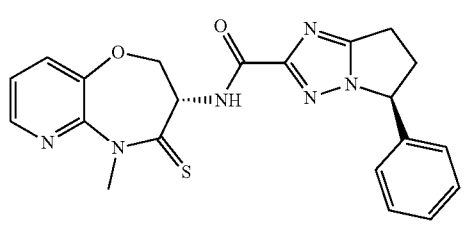 [SMILES: CN1C(=S)[C@@H](NC(=O)c2nc3n(n2)[C@H](c2ccccc2)CC3)COc2cccnc21]

Step 1: Synthesis of Compound WX013-1

LiOH.H$_2$O (245.59 mg, 5.85 mmol, 3 eq) was added to a solution of BB-11B (501.93 mg, 1.95 mmol, 1 eq) in tetrahydrofuran (9 mL) and water (3 mL), and the mixture was reacted at 25° C. for 2 hours. Water (10 mL) and ethyl acetate (10 mL) were added to the reaction solution, and the layers were separated. The aqueous phase was extracted with ethyl acetate (10 mL*2). The resulting aqueous phase was adjusted to a pH of 5-6 with 1 M HCl, and extracted with ethyl acetate (10 mL*2). The organic phases were combined, washed with saturated brine, dried over anhydrous sodium sulfate, and filtered. The filtrate was concentrated under reduced pressure (water pump, 45° C.) to give WX013-1. LCMS m/z=230.2 [M+1]$^+$. $^1$H NMR (400 MHz, DMSO-d$_6$) δ=12.75-13.57 (m, 1H), 7.33-7.44 (m, 3H), 7.18-7.28 (m, 2H), 5.57 (dd, J=7.97, 6.21 Hz, 1H), 3.06-3.22 (m, 2H), 2.94-3.03 (m, 1H), 2.53-2.61 (m, 1H).

Step 2: Synthesis of Compound WX013

N,N-diisopropylethylamine (23.16 mg, 179.20 μmol, 31.21 μL, 2.5 eq) and WX013-1 (24.65 mg, 107.52 μmol, 1.5 eq) were added to a solution of BB-1 (15 mg, 71.68 μmol, 1 eq) in DMF (1.5 mL), and propylphosphonic anhydride (T$_3$P, 68.42 mg, 107.52 μmol, 63.94 μL, 50% purity, 1.5 eq) was then added. The mixture was reacted at 25° C. for 1 hour. The reaction solution was filtered, and the filtrate was collected. The collected filtrate was purified by preparative HPLC (Column: Phenomenex Luna C18 150 mm*30 mm*5 μm; Mobile phase: [water (0.05% HCl)-ACN]; acetonitrile %: 20%-50%, 12 min) to give WX013. LCMS m/z=421.1

[M+1]⁺. ¹H NMR (400 MHz, DMSO-d₆) δ=8.68 (d, J=8.04 Hz, 1H), 8.46 (dd, J=4.72, 1.32 Hz, 1H), 7.78 (dd, J=8.04, 1.38 Hz, 1H), 7.47 (dd, J=8.04, 4.64 Hz, 1H), 7.32-7.43 (m, 3H), 7.24 (br d, J=6.65 Hz, 2H), 5.44-5.68 (m, 1H), 5.00 (dt, J=11.40, 7.40 Hz, 1H), 4.42-4.68 (m, 2H), 3.79 (s, 3H), 2.90-3.23 (m, 4H).

Example 14: WX14

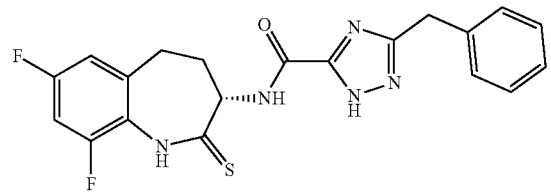 [SMILES: O=C(N[C@H]1CCc2cc(F)cc(F)c2NC1=S)c1nc(Cc2ccccc2)n[nH]1]

Route for Synthesis

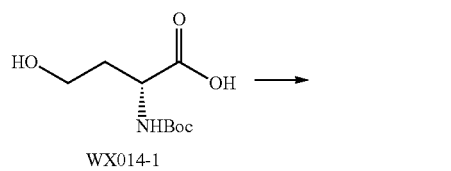
WX014-1

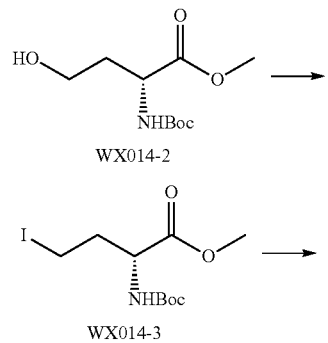
WX014-2

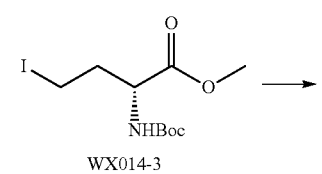
WX014-3

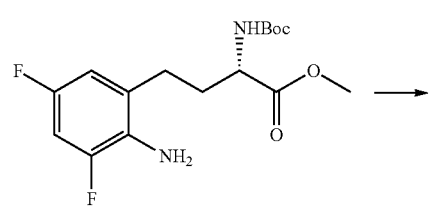
WX014-4

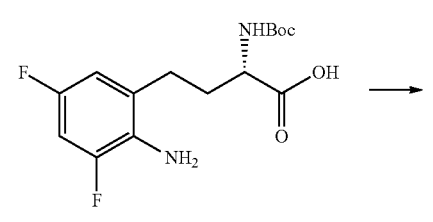
WX014-5

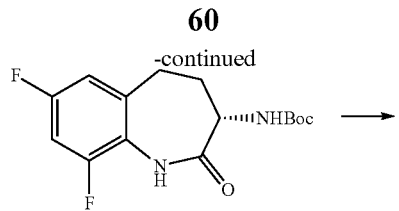
WX014-6

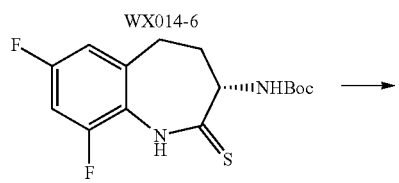
WX014-7

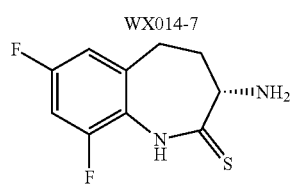
WX014-8

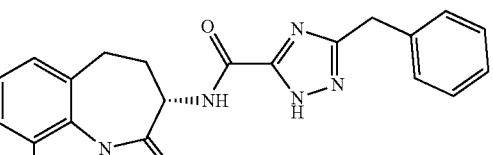
WX014

Step 1: Synthesis of Compound WX014-2

WX014-1 was dissolved in a solution of THF (100 mL) and MeOH (100 mL), and the reaction flask was placed in an ice water bath (0° C.). Trimethylsilyl diazomethane (2 M, 47.89 mL, 2.1 eq) was added to the flask, and the mixture was allowed to warm to 25° C. and stirred for 2 hours. Glacial acetic acid was added dropwise until the reaction solution turned pale yellow. The reaction solution was concentrated under reduced pressure to give compound WX014-2.

Step 2: Synthesis of Compound WX014-3

Triphenylphosphine (14.30 g, 54.53 mmol, 1.2 eq) and imidazole (3.71 g, 54.53 mmol, 1.2 eq) were dissolved in dichloromethane (120 mL) at 25° C., and I₂ (13.84 g, 54.53 mmol, 10.98 mL, 1.2 eq) was slowly added to the above mixture solution. The mixture solution was stirred for 10 minutes, and a solution of WX014-2 in DCM (80 mL) was added to the above solution. The mixture was reacted at 25° C. for 12 hours. The reaction solution was filtered, and the filtrate was concentrated under reduced pressure to give a crude product. The crude product was purified by column chromatography (petroleum ether:ethyl acetate=10:1-1:1) to give WX014-3. LCMS m/z=244.1 [M−100+1]⁺. ¹H NMR (400 MHz, CDCl₃) δ=5.10 (br d, J=4.82 Hz, 1H), 4.35 (br d, J=3.96 Hz, 1H), 3.77 (s, 3H), 3.18 (t, J=7.46 Hz, 2H), 2.30-2.49 (m, 1H), 2.18 (dq, J=14.32, 7.22 Hz, 1H), 1.43-1.47 (m, 9H).

Step 3: Synthesis of Compound WX014-4

1,2-Dibromoethane (82.12 mg, 437.12 μmol, 32.96 μL, 0.3 eq) was added to zinc powder (285.83 mg, 4.37 mmol, 3 eq) in DMF (2 mL). The mixture was stirred at 60° C. for 30 minutes, and then cooled to room temperature (25° C.). Trimethylchlorosilane (9.50 mg, 87.42 μmol, 11.10 μL, 0.06 eq) was added into the reaction flask, and the mixture was stirred at 25° C. for 30 minutes. A solution of WX014-2 in DMF (2 mL) was added to the above solution, and the mixture was reacted at 25° C. for 30 minutes, and then allowed to stand for 30 minutes. The upper emulsion was taken out and slowly added to a solution of tris(dibenzylideneacetone)dipalladium (44.08 mg, 48.14 μmol, 0.05 eq), tri-o-methylphenylphosphine (58.61 mg, 192.55 μmol, 0.2 eq), and B-12 in DMF (2 mL), and the mixture was reacted at 20° C. for 1 hour. Water (5 mL) and methyl tert-butyl ether (5 mL) were added to the reaction solution, and the layers were separated. The aqueous phase was extracted with methyl tert-butyl ether (5 mL*2). The organic phases were combined, washed with saturated brine, dried over anhydrous sodium sulfate, and filtered. The filtrate was concentrated under reduced pressure to give WX014-4. LCMS m/z=289.1 [M−56+1]⁺.

Step 4: Synthesis of Compound WX014-5

LiOH.H₂O (219.33 mg, 5.23 mmol, 3 eq) was added to a solution of WX014-4 in tetrahydrofuran (15 mL) and water (15 mL), and the mixture was reacted at 25° C. for 2 hours. 10 mL of Water and 10 mL of ethyl acetate were added to the reaction solution, and the layers was separated. The aqueous phase was extracted with ethyl acetate (10 mL*2). The resulting aqueous phase was adjusted to a pH of 5~6 with 1 M HCl, and extracted with ethyl acetate (10 mL*2). The organic phases were combined, washed with saturated brine, dried over anhydrous sodium sulfate, and filtered. The filtrate was concentrated under reduced pressure to give WX014-5. LCMS m/z=275.1 [M−56+1]⁺.

Step 5: Synthesis of Compound WX014-6

Propylphosphonic anhydride (895.80 mg, 1.41 mmol, 837.20 μL, 50% purity, 1.5 eq) was added to a solution of N,N-diisopropylethylamine (303.22 mg, 2.35 mmol, 408.65 μL, 2.5 eq) and WX014-5 in DMF (20 mL), and the mixture was reacted at 25° C. for 2 hours. Water (15 mL) and ethyl acetate (15 mL) were added to the reaction solution, and the layers were separated. The aqueous phase was extracted with ethyl acetate (15 mL*2). The organic phases were combined, washed with saturated brine, dried over anhydrous sodium sulfate, and filtered. The filtrate was concentrated under reduced pressure to give a crude product. The crude product was purified by column chromatography (petroleum ether:ethyl acetate=10:1~1:1) to give WX014-6. ¹H NMR (400 MHz, CDCl₃) δ=7.40 (br s, 1H), 6.76-6.87 (m, 2H), 5.46 (br d, J=7.46 Hz, 1H), 4.22-4.37 (m, 2H), 2.88-3.03 (m, 1H), 2.63-2.73 (m, 2H), 1.42 (s, 9H).

Step 6: Synthesis of Compound WX014-7

Lawsson's reagent (77.70 mg, 192.12 μmol, 1.5 eq) was added to a solution of WX014 (40 mg, 128.08 μmol, 1 eq) in toluene (5 mL) at 20° C., and the mixture was reacted at 70° C. for 12 hours. The reaction solution was concentrated under reduced pressure to give a crude product. The crude product was purified by column chromatography (petroleum ether:ethyl acetate=10:1~1:1) to give WX014-7. LCMS m/z=273.1 [M−56+1]⁺.

Step 7: Synthesis of Compound WX014-8

HCl/EtOAc (4 M, 2 mL) was added to a solution of WX014-7 in ethyl acetate (3 mL), id the mixture was reacted at 25° C. for 2 hours. The reaction solution was concentrated under reduced pressure (water pump, 40° C.) to give a crude product WX014-8. LCMS m/z=229.2 [M+1]⁺.

Step 8: Synthesis of Compound WX014

DIPEA (18.31 mg, 141.66 μmol, 24.67 μL, 2.5 eq) mid T₃P (54.09 mg, 84.99 μmol, 50.55 μL, 50% purity, 1.5 eq) were added to a solution of WX014-8 (15 mg, 56.66 μmol, 1 eq. HCl) and BB-1 (14.97 ng, 73.66 μmol, 1.3 eq) in DMF (2 mL), and the mixture was reacted at 25° C. for 2 hours. Water (5 mL) and ethyl acetate (5 mL) were added to the reaction solution, and the layers were separated. The aqueous phase was extracted with ethyl acetate (5 mL*2). The organic phases were combined, washed with saturated brine, dried over anhydrous sodium sulfate, and filtered. The filtrate was concentrated wider reduced pressure to give a crude product. The crude product was purified by preparative HPLC (Column: Phenomenex Luna C18 150 mm*30 mm*5 μm; Mobile phase: [water (0.05% HCl)-ACN]; acetonitrile %: 20%-50%, 12 min) to give WX014. LCMS m/z=414.2 [M+1]⁺. ¹H NMR (400 MHz, CD₃OD) δ=7.21-7.37 (m, 5H), 6.97-7.13 (m, 2H), 4.71 (br d, J=4.14 Hz, 1H), 4.18 (br s, 2H), 2.84-2.96 (m, 1H), 2.64-2.83 (m, 2H), 2.17 (td, J=11.67, 7.78 Hz, 1H).

Example 15: WX015

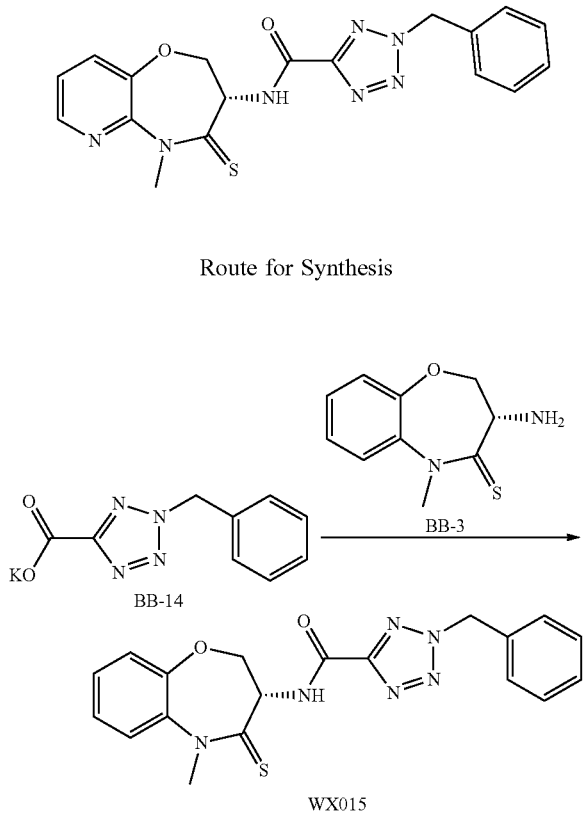

Route for Synthesis

Step 1: Synthesis of Compound WX015

To a round bottom flask containing N,N-dimethylformamide (10 mL) were added BB-3 (20 n, 96.02 μmol, 1.1 eq)

and DIPEA (23.69 mg, 183.32 μmol, 31.93 μL, 2.1 eq). After dissolved, BB-14 (21.24 mg, 87.30 μmol, 1 eq) and T₃P (55.55 mg, 87.30 μmol, 51.92 μL, 50% purity, 1 eq) were added, and then the mixture was reacted with stirring at 25° C. for 12 hours. LCMS showed that the raw materials were basically consumed. The reaction solution was concentrated under reduced pressure to about 5 mL. HPLC (Column: Welch Xtimate C18 150*25 mm*5 μm; Mobile phase: [water (0.225% FA)-ACN]; acetonitrile %: 35%-65%, 8 min) was used for purification to give product WX015. ¹H NMR (400 MHz, CDCl₃) δ=8.78 (br d, J=7.5 Hz, 1H), 7.43-7.35 (m, 5H), 7.35-7.26 (m, 4H), 5.82 (s, 2H), 5.21 (td, J=6.9, 11.0 Hz, 1H), 4.71 (dd, J=6.5, 9.5 Hz, 1H), 4.33-4.21 (m, 1H), 3.87 (s, 3H); LCMS m/z=395.1 [M+1]⁺.

Example 16: WX16

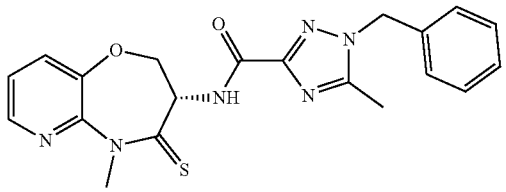 [SMILES: Cc1nc(C(=O)N[C@H]2COc3cccnc3N(C)C2=S)nn1Cc1ccccc1]

Route for Synthesis

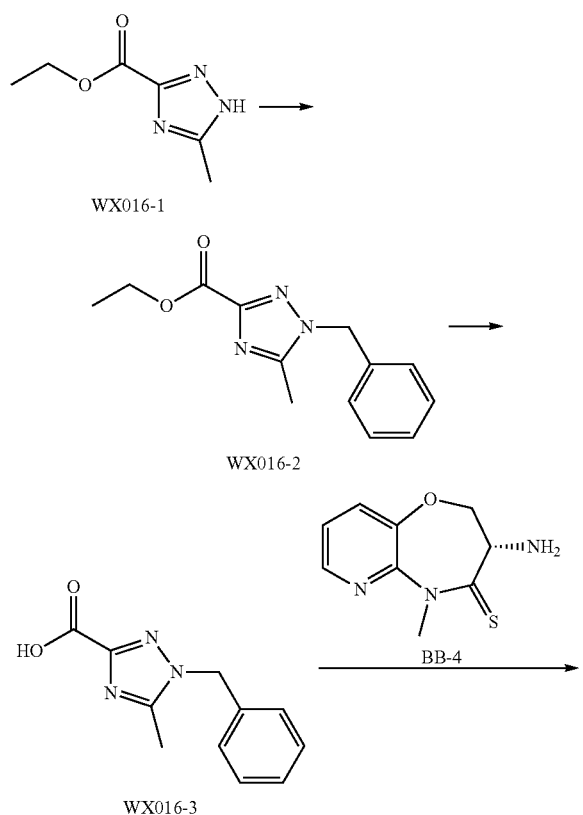

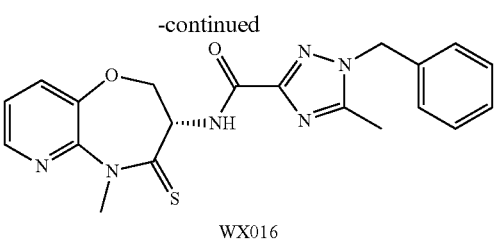

WX016

Step 1: Synthesis of Compound WX016-2

To a round bottom flask was added DMSO (10 mL), and then WX016-1 (1.31 g, 8.44 mmol, 1 eq), K₂CO₃ (1.40 g, 10.13 mmol, 1.2 eq) and benzyl bromide (1.59 g, 9.29 mmol, 1.10 mL, 1.1 eq) were slowly added. The mixture was continuously stirred at 25° C. for 12 hours. After the completion of the reaction, water (50 mL) was added to the reaction solution, and the mixture was extracted twice with ethyl acetate (30 mL×2). The organic phases were combined, washed with saturated brine (5 mL×2), and concentrated under reduce pressure to give a crude product. The crude product was purified by column chromatography (petroleum ether:ethyl acetate=1001~1:1) to give WX016-2. ¹H NMR (400 MHz, CDCl₃) δ=7.39-7.30 (m, 3H), 7.19 (dd, J=1.8, 7.6 Hz, 2H), 5.39 (s, 2H), 4.49 (q, J=7.1 Hz, 2H), 2.43 (s, 3H), 1.44 (t, J=7.1 Hz, 3H); LCMS m/z=246.1 [M+1]⁺.

Step 2: Synthesis of Compound WK016-3

To a round bottom flask were added THF (7.5 mL) and H₂O (2.5 mL), and then WX016-2 (1 g, 4.08 mmol, 1 eq) and LiOH.H₂O (513.26 mg, 12.23 mmol, 3 eq) were slowly added. The mixture was reacted with stirring at 25° C. for 2 hours. The reaction solution was concentrated under reduced pressure, and 2N hydrochloric acid was added dropwise to adjust pH to acidic. The mixture was filtered to give a filter cake which was the target compound WX016.3. ¹H NMR (400 MHz, CDCl₃) δ=7.42-7.28 (m, 3H), 7.25-7.19 (m, 2H), 5.40 (s, 2H), 2.56 (s, 3H); LCMS m/z=217.9 [M+1]⁺.

Step 3: Synthesis of Compound WX016

To a round bottom flask were added N,N-dimethylformamide (1 mL), WX016-3 (80 mg, 368.28 μmol, 1 eq) and BB-4 (77.07 mg, 368.28 μmol, 1 eq), and then T₃P (351.54 mg, 552.43 μmol, 328.55 μL, 50% purity, 1.5 eq) and DIPEA (142.79 mg, 1.10 mmol, 192.45 μL, 3 eq) were added. The mixture was continuously stirred at 25° C. for 5 hours, and then concentrated to give a crude product. The crude product was purified by preparative HPLC (Column: Welch Xtimate C18 150*25 mm*5 μm; Mobile phase: [water (0.225% FA)-ACN]; acetonitrile %: 35%-65%, 8 min) to give compound WX016. ¹H NMR (400 MHz, CDCl₃) δ=8.72 (br d, J=7.3 Hz, 1H), 8.37 (dd, J=1.4, 4.6 Hz, 1H), 7.56 (dd, J=1.3, 8.0 Hz, 1H), 7.38-7.27 (m, 4H), 7.18 (br d, J=6.0 Hz, 2H), 5.36 (s, 2H), 5.23 (td, J=6.8, 11.0 Hz, 1H), 4.78 (dd, J=6.5, 9.5 Hz, 1H), 4.32 (dd, J=9.8, 11.0 Hz, 1H), 3.93 (s, 3H), 2.41 (s, 3H); LCMS m/z=409.1 [M+1]⁺.

Example 17: WX17

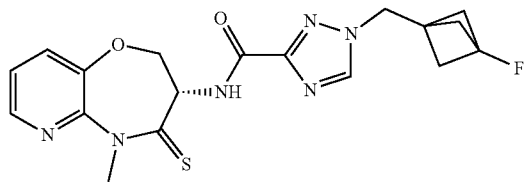 [SMILES: CN1C(=S)[C@@H](NC(=O)c2ncn(CC34CC(F)(C3)C4)n2)COc2cccnc21]

Route for Synthesis

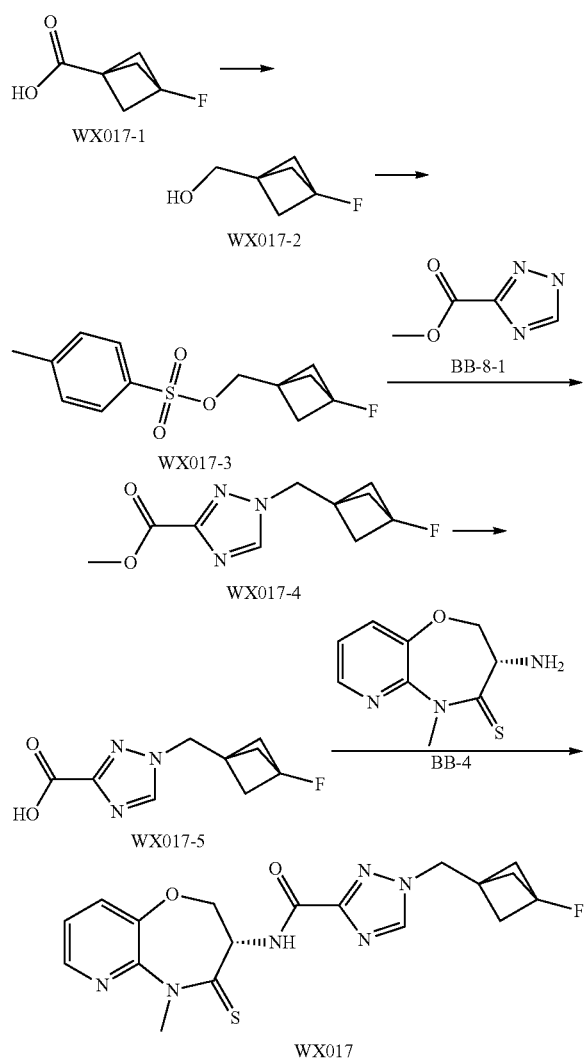

Step 1: Synthesis of Compound WX017-2

To a reaction flak were added lithium aluminum hydride (629.99 mg, 16.60 mmol, 2 eq) and THF (5 mL) at 25° C., and then a solution of WX017-1 (1.08 g, 8.30 mmol, 1 eq) in THF (5 mL) was slowly added dropwise. After the completion of addition, the mixture was heated to 35° C., and continuously stirred for 1 hour. The reaction was quenched by adding 6 mL of saturated aqueous $Na_2SO_4$ solution. The mixture was filtered, and washed with ethyl acetate (10 mL×3 times). The organic phase were combined, dried over anhydrous $MgSO_4$, and filtered. The filtrate was concentrated wider reduced pressure. The crude product was purified by silica gel column chromatography (petroleum ether:ethyl acetate=100:1~5:1) to give compound WX017-2. $^1H$ NMR (400 MHz, $CDCl_3$) δ=3.84 (s, 2H), 2.01 (d, J=2.5 Hz, 6H).

Step 2: Synthesis of Compound WX017-3

To a reaction flask were added WX017-2, DCM (10 mL), and pyridine (1.40 g, 17.70 mmol, 1.43 mL, 4.11 eq), and then p-toluenesulfonyl chloride (1.23 g, 6.46 mmol, 1.5 eq) was slowly added. The mixture was heated to 40° C. and reacted for 24 hours. A new spot (Rf=0.7) appeared by TLC (petroleum ether:ethyl acetate=5:1) monitoring. The reaction solution was directly concentrated under reduced pressure, and the crude product was purified by silica gel column chromatography (petroleum ether:ethyl acetate=100:1-30:1) to give compound WX017-3. $^1H$ NMR (400 MHz, $CDCl_3$) δ=7.78 (d, J=8.3 Hz, 2H), 7.35 (d, J=8.0 Hz, 2H), 4.24 (s, 2H), 2.46 (s, 3H), 1.99 (d, J=2.3 Hz, 6H).

Step 3: Synthesis of Compound WX017-4

To a eggplant-shaped bottle, acetonitrile (10 mL). WX017-3 (500 mg, 1.85 mmol, 1.1 eq) and BB-8-1 (213.72 mg, 1.68 mmol, 1 eq) were added at 25° C. and then $K_2CO_3$ (278.88 mg, 2.02 mmol, 1.2 eq) was added. The mixture was heated to 70° C. and reacted for 48 hours. The reaction solution was concentrated, and the crude product was purified by silica gel column (eluent: petroleum ether:ethyl acetate=100:1-1:2) to give compound WX017-4. $^1H$ NMR (400 MHz, $CDCl_3$) δ=8.12 (s, 1H), 4.57 (s, 2H), 4.01 (s, 3H), 2.05 (d, J=2.5 Hz, 6H).

Step 4: Synthesis of Compound WX017-5

To a round bottom flask containing THF (2 mL) was added WX017-4 (100 mg, 444.01 μmol, 1 eq) at 25° C. After dissolved, a solution of $LiOH.H_2O$ (55.90 mg, 1.33 mmol, 3 eq) in MeOH (1 mL) was added aropwise, and the mixture was reacted at 25° C. for 5 hours. The mixture was concentrated under reduced pressure and the residue was dissolved in tetrahydrofuran (5 mL). 1N dilute hydrochloric acid was added to adjust pH to 4, and toluene (5 mL) was then added. The mixture was mixed well, and the solvent was then evaporated to dryness under reduced pressure to give a crude product of WX017-5, which was directly used in the ne % t step without purification.

Step 5: Synthesis of Compound WX017

To a reaction flask were added ethyl acetate (10 mL), WX017-5 (207 mg, 588.09 μmol, 1 eq), and BB-4 (143.52 mg, 588.09 μmol, 1 eq) at 25° C. After dissolved, $T_3P$ (1.12 g, 1.76 mmol, 1.05 mL, 30% purity, 3 eq) and DIPEA (228.02 mg, 1.76 mmol, 307.30 μL, 3 eq) were added, and the mixture was reacted at 25° C. for 8 hours. After the completion of the reaction, ethyl acetate (10 mL) was added. The organic phase was washed with water (10 mL×3 times), followed by saturated brine (10 mL-1 time), and concentrated under reduced pressure to give a crude product. The crude product was purified by preparative HPLC (Column: Welch Xtimate C18 150*25 mm*5 μm; Mobile phase:

[Water (0.05% NH$_3$H$_2$O)-ACN]; acetonitrile %: 35%-65%, 8 min) to give compound WX017. $^1$H NMR (400 MHz, CDCl$_3$) δ=8.83 (br d, J=6.8 Hz, 1H), 8.37 (dd, J=1.4, 4.6 Hz, 1H), 8.06 (s, 1H), 7.57 (dd, J=1.3, 8.0 Hz, 1H), 7.29 (dd, J=4.8, 8.0 Hz, 1H), 5.20 (td, 6.7, 11.2 Hz, 1H), 4.80 (dd, J=6.4, 9.4 Hz, 1H), 4.54 (s, 2H), 4.33 (dd, J=9.8, 11.0 Hz, 1H), 3.94 (s, 3H), 2.05 (d, J=2.3 Hz, 6H); LCMS m/z=403.2 [M+1]$^+$.

Example 18: WX018

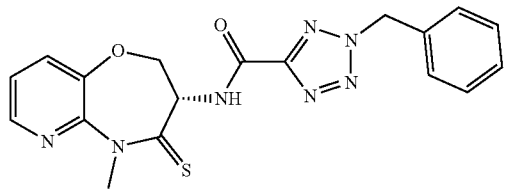 [SMILES: CN1C(=S)[C@@H](NC(=O)c2nnn(Cc3ccccc3)n2)COc2cccnc21]

Route for Synthesis

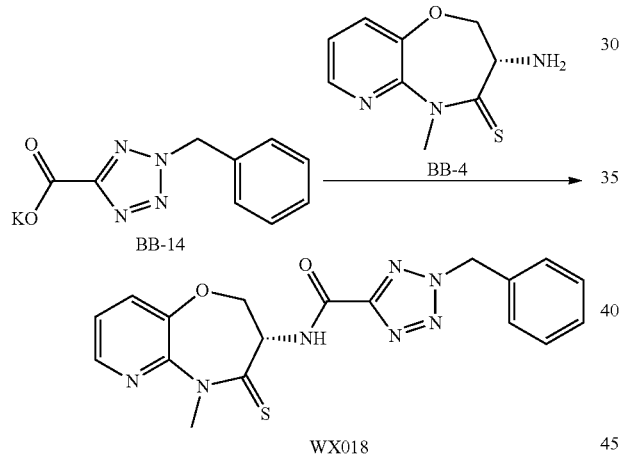

Synthesis of Compound WX015

To a round bottom flask containing N,N-dimethylformamide (10 mL) % we added BB-4 (200 mg, 955.71 μmol, 1.1 eq) and DIPEA (235.80 mg, 1.82 mmol, 317.80 μL, 2.1 eq). After dissolved, BB-14 (210.50 mg, 866.83 μmol, 1 eq) and T$_3$P (552.89 mg, 868.83 μmol, 516.72 μL, 50% purity, 1 eq) were added, and the mixture was then stirred at 25° C. for 12 hours. The reaction solution was concentrated under reduced pressure to about 5 mL. HPLC (Column: Welch Xtimate C18150*25 mm*5 μm; Mobile phase: [water (0.225% FA)-ACN]; acetonitrile %: 35%-65% 8 min) was used for purification to give compound WX018. $^1$HNMR (400 MHz, CDCl$_3$) δ=8.86 (br d, J=6.8 Hz, 1H), 8.38 (dd, J=1.6, 4.6 Hz, 1H), 7.69-7.27 (m, 7H), 5.83 (s, 2H), 5.20 (td, J=6.7, 11.2 Hz, 1H), 4.78 (dd, J=6.3, 9.5 Hz, 1H), 4.33 (dd, J=9.7, 11.2 Hz, 1H), 3.93 (s, 3H); LCMS m/z=396.1 [M+1]$^+$.

Example 19: WX19

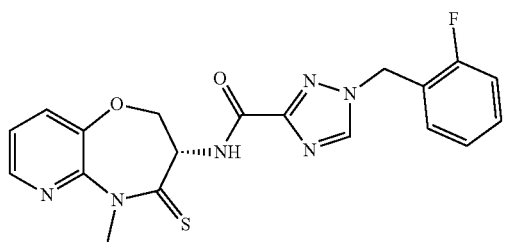 [SMILES: CN1C(=S)[C@@H](NC(=O)c2ncn(Cc3ccccc3F)n2)COc2cccnc21]

Route for Synthesis

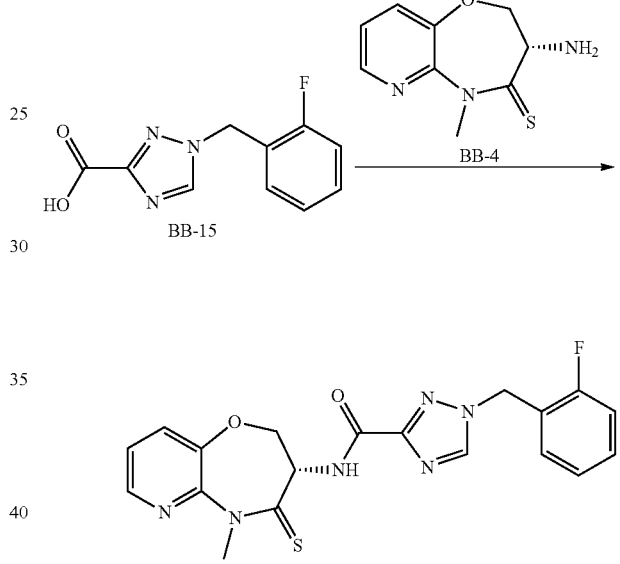

Step 1: Synthesis of Compound WX019

To a round bottom flask containing N,N-dimethylformamide (10 mL) awe added BB-15 (156.11 mg, 745.97 μmol, 1.1 eq), BB-4 (150 mg, 678.16 μmol, 1 eq), T$_3$P (431.55 mg, 678.16 μmol, 403.32 μL, 50% purity, 1 eq), and DIPEA (184.06 mg, 1.42 mmol, 248.06 μL, 2.1 eq), and then stirring was started. The mixture was reacted with stirring at 25° C. for 12 hours. After the completion of the reaction, the reaction solution was concentrated under reduced pressure to about 5 mL. HPLC (Column: Welch Xtimate C18 150*25 mm*5 μm; Mobile phase: [water (0.225% FA)-ACN]; acetonitrile %: 35%-65%, 8 min) was used for purification to give product WX019. $^1$H NMR (400 MHz, CDCl$_3$) δ=81 (br d, J=7.3 Hz, 1H), 8.37 (dd, J=1.5, 4.8 Hz, 1H), 8.14 (s, 1H), 7.56 (dd, J=1.5, 8.0 Hz, 1H), 7.41-7.27 (m, 3H), 7.21-7.06 (m, 2H), 5.45 (s, 2H), 5.20 (td, J=6.7, 11.2 Hz, 1H), 4.78 (dd, J=6.5, 9.5 Hz, 1H), 4.31 (dd, J=9.5, 11.0 Hz, 1H), 3.93 (s, 3H); $^{19}$F NMR (376 MHz, CDCl$_3$) δ=−109.59~−130.05 (m, 1F); LCMS m/z=413.1 [M+1]$^+$.

Example 20: WX020

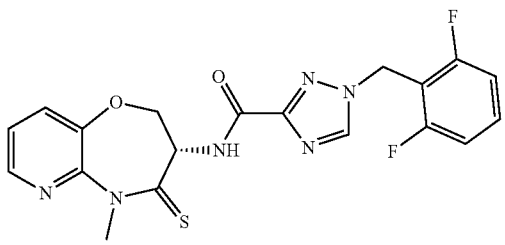 [SMILES: CN1C(=S)[C@@H](NC(=O)c2ncn(Cc3c(F)cccc3F)n2)COc2cccnc21]

Route for Synthesis

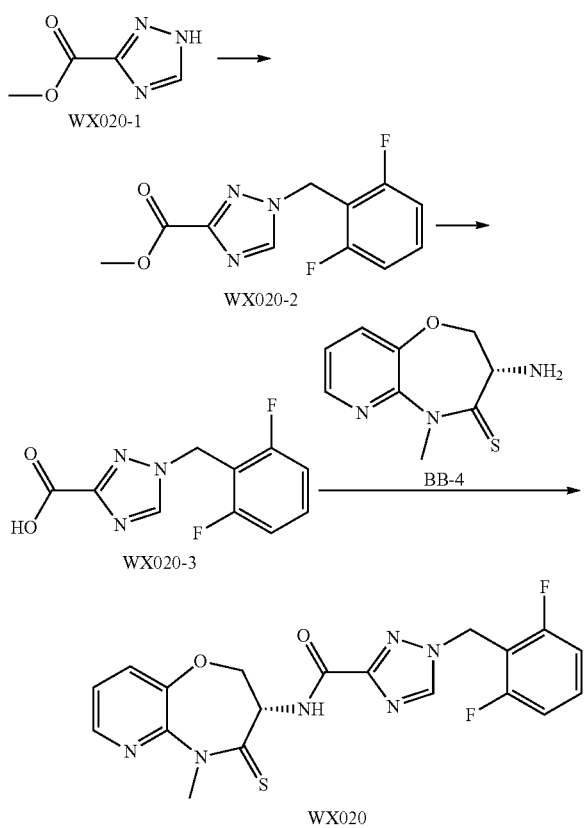

Step 1: Synthesis of Compound WX020-2

To acetonitrile (15 mL) were added WX020-1 (3 g, 23.60 mmol, 1 eq), 2,6-difluorobenzyl bromide (5.37 g, 25.96 mmol, 1.1 eq), and K$_2$CO$_3$ (3.91 g, 28.32 mmol, 1.2 eq), and then stirring was started. The mixture was reacted at 50° C. for 12 hours. After the reaction was completed by TLC monitoring, the reaction solution was filtered to remove K$_2$CO$_3$, and the filter cake was washed three times with ethyl acetate (15 mL). Saturated brine (50 mL) was added to the filtrate, and then an organic phase was obtained after extraction. The aqueous phase was extracted with EA (30 mL) gain. The organic phases were combined, and concentrated under reduced pressure to give a crude product. The crude product was purified by silica gel column (eluent: petroleum ether:ethyl acetate=100:1~100:100) to give compound WX020-2. $^1$H NMR (400 MHz, CDCl$_3$) δ=8.17 (s, 1H), 7.46-7.33 (m, 1H), 7.04-6.91 (m, 2H), 5.51 (s, 2H), 4.13-3.85 (m, 3H).

Step 2: Synthesis of Compound WX020-3

To a round bottom flask containing THF (30 mL) was added WX020-2 (1 g, 3.95 mmol, 1 eq). After dissolved, a solution of LiOH.H$_2$O (331.43 ng, 7.90 mmol, 2 eq) in H$_2$O (5 mL) was added, and the mixture was reacted with stirring at 20° C. for 2 hours. The reaction solution was adjusted to a pH of 6 with 1 M diluted hydrochloric acid, and the mixture was then concentrated under reduced pressure to remove the solvent to give a crude product WX020-3; LCMS m/z=239.9 [M+1]$^+$.

Step 3: Synthesis of Compound WX020

To a round bottom flask containing N,N-dimethylformamide (10 mL) were added BB-4 (192.49 mg, 919.82 μmol, 1.1 eq), WX020-3 (200 mg, 836.20 μmol, 1 eq), T$_3$P (532.12 mg, 836.20 μmol, 497.31 μL, 50% purity, 1 eq), and DIPEA (226.95 mg, 1.76 mmol, 305.86 μL, 2.1 eq), and the mixture was reacted with stirring at 25° C. for 12 hours. The reaction solution was concentrated under reduced pressure to about 5 mL, and the residue was purified by preparative HPLC (Column Welch Xtimate C18 150*25 mm*5 μm; Mobile phase: [water (0.225% FA)-ACN]; acetonitrile %: 35%-65%, 8 min) to give compound WX020. $^1$H NMR (400 MHz, CDCl$_3$) δ=8.79 (br d, J=7.0 Hz, 1H), 8.36 (dd, 3=1.5, 4.8 Hz, 1H), 8.14 (s, 1H), 7.55 (dd, J=1.5, 8.0 Hz, 1H), 7.43-7.26 (m, 2H), 6.97 (t, J=7.9 Hz, 2H), 5.49 (s, 2H), 5.19 (td, J=6.7, 11.1 Hz, 1H), 4.77 (dd, J=6.3, 9.5 Hz, 1H), 4.30 (dd, J=9.7, 10.9 Hz, 1H), 3.92 (s, 3H); $^{19}$F NMR (376 MHz, CDCl$_3$) δ=−104.74~120.36 (m, 1F); LCMS m/z=431.1 [M+1]$^+$.

Example 21: WX021

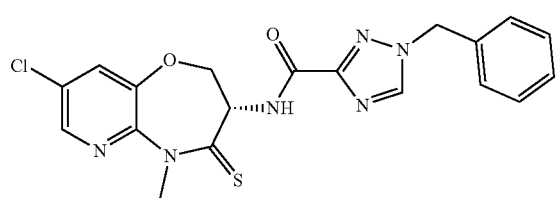 [SMILES: CN1C(=S)[C@@H](NC(=O)c2ncn(Cc3ccccc3)n2)COc2cc(Cl)cnc21]

Route for Synthesis

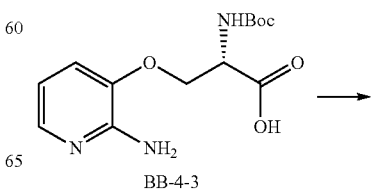

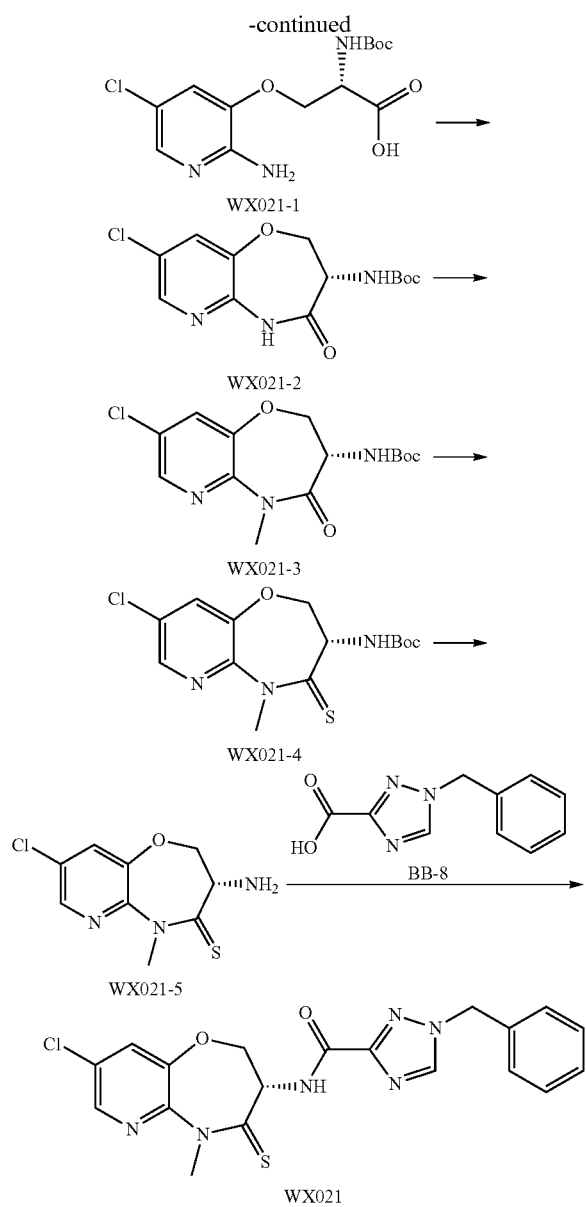

mmol, 5.74 mL, 50% purity, 2 eq), and DIPEA (1.87 g, 14.47 mmol, 2.52 mL, 3 eq), and the mixture was reacted at 20° C. for 3 hours. The reaction solution was poured into saturated brine (300 mL), mid the layers were separated to give an organic phase. The aqueous phase was extracted twice with ethyl acetate (100 mL). The organic phases was combined and concentrated under reduced pressure to give a crude product. The crude product was purified by silica gel column (petroleum ether:ethyl acetate=100:20~100:00) to give compound WX021-2. $^1$H NMR (400 MHz, CDCl$_3$) δ=8.22 (br s, 1H), 8.04 (d, J=2.0 Hz, 1H), 7.41 (d, J=2.3 Hz, 4H), 5.59 (br s, 1H), 4.71-4.46 (m, 2H), 4.23-4.05 (m, 1H), 1.46 (s, 9H); LCMS m/z=257.8 [M−56+]$^+$.

Step 3: Synthesis of Compound WX021-3

To a round bottom flask containing N,N-dimethylacetamide (10 mL) were added WX021-2 (200 mg, 637.48 μmol, 1 eq), iodomethane (1.17 g, 8.24 mmol, 513.16 μL, 12.93 eq), and cesium carbonate (415.41 mg, 1.27 mmol, 2 eq). The mixture was reacted with stirring at 25° C. under nitrogen for 1 hour. After the completion of the reaction, the reaction solution was poured into saturated brine (20 mL), and the mixture was extracted three times with ethyl acetate (15 mL). The organic phases were combined and concentrated under reduced pressure to give a crude product. The crude product was dissolved in ethyl acetate (2 mL), and purified by preparative TLC (petroleum ether:ethyl acetate=3:1) to give a product WX021-3. $^1$H NMR (400 MHz, CDCl$_3$) δ=8.23 (d, J=2.3 Hz, 1H), 7.47 (d, J=2.0 Hz, 1H), 5.55 (br s, 1H), 4.82-4.49 (m, 2H), 4.35-4.14 (m, 1H), 3.47 (s, 3H), 1.41 (s, 9H).

Step 4: Synthesis of Compound WX021-4

To a round bottom flask containing toluene (10 mL) were added WX021-3 (177 mg, 540.02 μmol, 1 eq) and Lawson's reagent (327.63 ng, 810.04 μmol, 1.5 eq) at 25° C., and the mixture was slowly heated to 110° C. and reacted for 12 hours. The reaction solution was poured into saturated brine (100 mL), and the mixture was extracted three times with ethyl acetate (30 mL). The organic phases were combined, and concentrated under reduced pressure to give a crude product. The crude product was purified by preparative TLC (petroleum ether:ethyl acetate=3:1) to give compound WX021-4. LCMS m/z=287.8 [M−56+1]$^+$.

Step 5: Synthesis of Compound WX021-5

To a round bottom flask containing dichloromethane (5 mL) was added WX021-4 (35 mg, 101.0 μmol, 1 eq) at 25° C. Trifluoroacetic acid (174.10 mg, 1.53 mmol, 113.06 μL, 15 eq) was added dropwise with stirring, and the mixture was continuously reacted for 2 hours. The reaction solution was evaporated to dryness under reduced pressure to give a crude product of WX021-5, which was used directly in the net step.

Step 6: Synthesis of Compound WX021

To a round bottom flask containing N,N-dimethylacetamide (5 mL) were added WX021-5 (20 mg, 82.06 μmol, 1 eq), BB-8 (16.68 mg, 82.06 μmol, 1 eq), T$_3$P (52.22 mg, 82.06 μmol, 48.81 μL, 30% purity, 1 eq), and DIPEA (22.27 mg, 172.33 μmol, 30.02 μL, 2.1 eq), and the mixture was reacted at 25° C. for 5 hours. Saturated brine (30 mL) was added, and the mixture was extracted with ethyl acetate (30

Step 1: Synthesis of Compound WX021-1

To a round bottom flask containing DCM (20 mL) was added BB-3-4 (2 g, 6.73 mmol, 1 eq), and the mixture was stirred at 40° C. NCS (968.1 mg, 7.40 mmol, 1.1 eq) was slowly added, and then the reaction was continuously stirred at 40° C. for 5 hours. The reaction solution was concentrated under reduced pressure to give a crude product. The crude product was purified by silica gel column (eluent: DCM:MeOH=100~100:10) to give compound WX021-1. $^1$H NMR (400 MHz, CD$_3$OD) δ=7.54 (d, J=1.5 Hz, 1H), 7.34 (d, J=1.8 Hz, 1H), 6.95-6.77 (m, 1H), 5.49 (s, 2H), 4.70-4.60 (m, 2H), 4.53 (br dd, J=4.3, 9.5 Hz, 1H), 4.39-4.26 (m, 1H), 1.46 (s, 9H), LCMS m/z=331.9 [M+1]$^+$.

Step 2: Synthesis of Compound WX021-2

To a round bottom flak containing DCM (10 mL) were added WX021-1 (1.60 g, 4.82 mmol, 1 eq), T$_3$P (6.14 g, 9.65 mL×3). The organic phase was concentrated under reduced pressure to give a crude product. The crude product was purified by HPLC (formic acid system) (Column: Xtimate C18 100*30 mm*3 µm; Mobile phase [water (0.225% FA)-ACN]; acetonitrile %: 40%-70%, 8 min) to give compound WX021. $^1$H NMR (400 MHz, CDCl$_3$) δ=8.77 (br d, J=7.3 Hz, 1H), 8.32 (d, J=2.3 Hz, 1H), 8.04 (s, 1H), 7.57 (d, J=2.0 Hz, 1H), 7.44-7.34 (m, 3H), 7.32-7.27 (m, 2H), 5.40 (s, 2H), 5.26-5.16 (m, 1H), 4.77 (dd, J=3, 9.5 Hz, 1H), 4.39-4.27 (m, 1H), 3.90 (s, 3H); LCMS m/z=429.0 [M+1]$^+$.

J=2.0 Hz, 1H), 8.14 (s, 1H), 7.57 (d, J=2.3 Hz, 1H), 7.41-7.31 (m, 2H), 7.20-7.07 (m, 2H), 5.45 (s, 2H), 5.30-5.08 (m, 1H), 4.76 (dd, 3-6.3, 9.5 Hz, 1H), 4.32 (t, J=10.3 Hz, 1H), 3.93-3.87 (m, 1H); $^{19}$F NMR (376 MHz, CDCl$_3$) δ=−110.66~−127.90 (m, 1F); LCMS m/z=447.1[M+1]$^+$.

Example 23: WX023

Example 22: WX022

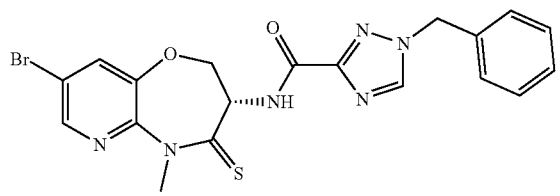

Route for Synthesis

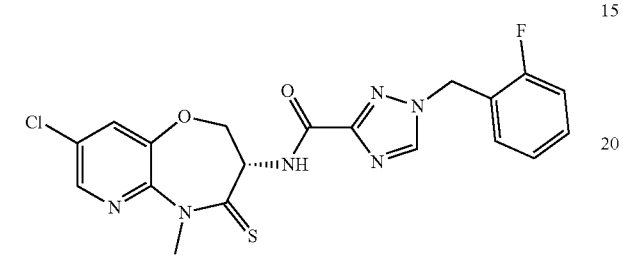

Step 1: Synthesis of Compound WX022

To N,N-dimethylacetamide (5 mL) were added WX021-5 (20 mg, 82.06 µmol, 1 eq). BB-15 (18.15 mg, 82.06 µmol, 1 eq), T$_3$P (52.22 mg, 82.06 µmol, 48.81 µL, 50% purity, 1 eq), and DIPEA (22.27 ng, 172.33 µmol, 30.02 µL, 2.1 eq), and the mixture was reacted at 25° C. for 5 hours, 30 mL of saturated brine was added, and the mixture was extracted with ethyl acetate (30 mL×3) to give an organic phase. The organic phase was concentrated under reduced pressure to give a crude product. The crude product was purified by preparative HPLC (Column: Xtimate C18 100*30 mm*3 µm; Mobile phase: [water (0.225% FA)-ACN]; acetonitrile %: 42%-72%, 8 min) to give compound WX022. $^1$H NMR (400 MHz, CDCl$_3$) δ=8.77 (br d, 3-6.5 Hz, 1H), 8.32 (d,

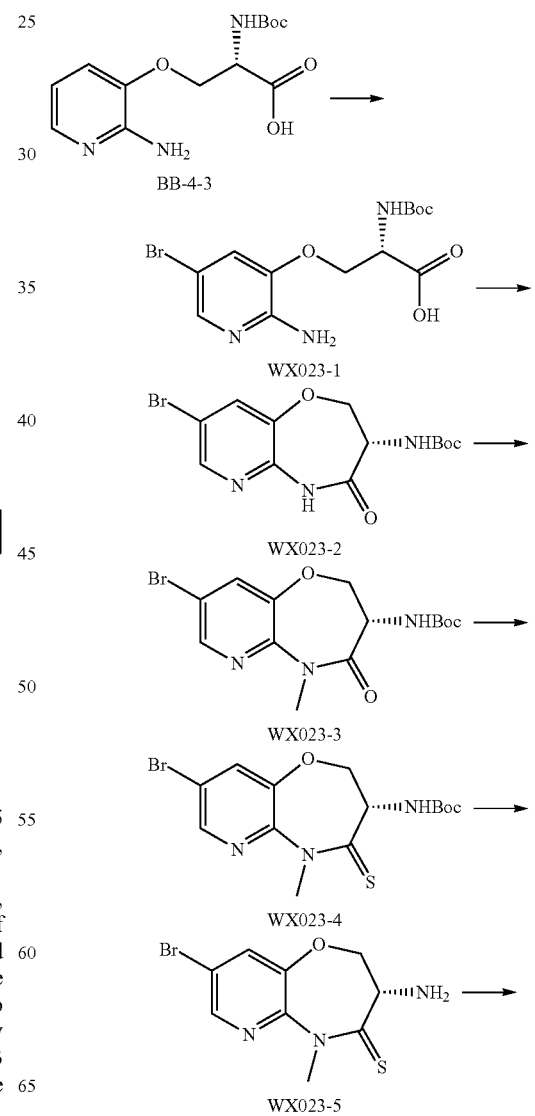

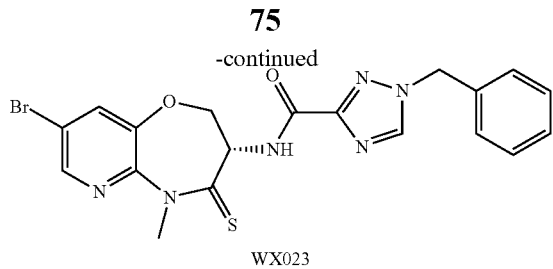

WX023

Step 1: Synthesis of Compound WX023-1

BB-4-3 (3.00 g, 10.09 mmol, 1 eq) and N-bromosuccinimide (1.98 g, 11.10 mmol, 1.1 eq) were slowly added to DCM (30 mL) at 25° C., and the reaction solution was continuously stirred at 25° C. under nitrogen for 12 hours. The reaction solution was slowly poured into water (100 mL), and the mixture was extracted with dichloromethane (100 mL×2). The organic phases were combined and washed successively with water (100 mL) and saturated brine (100 mL) to give an organic phase. The organic phase was concentrated under reduced pressure. The crude product was purified by silica gel column chromatography (dichloromethane:methanol=100:1~100:5) to give compound WX023-1.

Step 2: Synthesis of Compound WX023-2

To a round bottom flask was added ethyl acetate (100 mL) a 25° C. WX023-1 (5.60 g, 14.89 mmol, 1 eq), $T_3P$ (14.21 g, 22.33 mmol 13.28 mL, 50% purity, 1.5 eq) and DIPEA (3.85 g, 29.77 mmol, 5.19 mL, 2 eq) were then slowly added. The reaction solution was continuously stirred at 25° C. under nitrogen for 1 hour. The reaction solution was slowly poured into water (200 mL), and the mixture was extracted with ethyl acetate (200 mL×2). The organic phases were combined and washed successively with water (200 mL) and saturated brine (200 mL) to give an organic phase. The organic phase concentrated under reduced pressure. The crude product was purified by silica gel column chromatography (petroleum ether:ethyl acetate=100:1~1:1) to give compound WX023-2.

Step 3: Synthesis of Compound WX023-3

To a round bottom flask was added N,N-dimethylformamide (10 mL) at 25° C. WX023-2 (1.80 g, 5.03 mmol, 1 eq), iodomethane (5.71 g, 40.23 mmol, 2.50 mL, 8.01 eq) and cesium carbonate (3.60 g, 11.06 mmol, 2.2 eq) were then slowly added. The reaction solution was continuously stirred at 25° C. under nitrogen for 1 hour. The reaction solution was slowly poured into water (100 mL), and the mixture was extracted with ethyl acetate (100 mL×2). The organic phases were combined and washed successively with water (100 mL) and saturated brine (100 mL). The organic phase was concentrated under reduced pressure to give a crude product. The crude product was purified by silica gel column chromatography (petroleum ether:ethyl acetate=100:1-3:1) to give compound WX023-3. $^1$H NMR (400 MHz, CDCl$_3$) δ=8.32 (d, J=2.0 Hz, 1H), 7.61 (d, J=2.3 Hz, 1H), 5.55 (br d, J=4.8 Hz, 1H), 4.79-4.44 (m, 2H), 4.34-4.11 (m, 1H), 3.46 (s, 3H), 1.40 (s, 9H).

Step 4: Synthesis of Compound WX023-4

To a round bottom flask was added toluene (50 mL) at 25° C., and then WX023-3 (1.35 g, 3.63 mmol, 1 eq) and Lawsson's reagent (2.20 g, 5.44 mmol, 1.5 eq) were slowly added. The reaction solution was continuously stirred at 110° C. under nitrogen for 11 hours. The reaction solution was slowly poured into water (100 mL), and the mixture was extracted with ethyl acetate (100 mL×2). The organic phases were combined aid washed successively with water (100 mL) and saturated brine (100 mL). The organic phase was concentrated under reduced pressure to give a crude product. The crude product was purified by silica gel column chromatography (petroleum ether:ethyl acetate=100:1~1:1) to give compound WX023-4. $^1$H NMR (400 MHz, CDCl$_3$) δ=8.38 (d, J=2.0 Hz, 11H), 7.65 (d, J=2.3 Hz, 1H), 6.10 (br d, J=7.3 Hz, 1H), 4.81-4.67 (m, 1H), 4.58 (dd, J=6.1, 9.4 Hz, 1H), 4.23 (dd, J=9.5, 11.3 Hz, 1H), 3.87 (s, 3H), 1.41 (s, 9H).

Step 5: Synthesis of Compound WX023-5

To a round bottom flask was added dichloromethane (40 mL) at 25° C., and then WX023-4 (980 mg, 2.52 mmol, 1 eq) and trifluoroacetic acid (6.16 g, 54.02 mmol, 4, 21.40 eq) were slowly added. The reaction solution was continuously stirred at 25° C. under nitrogen for 11 hours. The reaction solution was slowly poured into saturated aqueous sodium bicarbonate solution (100 mL), and the mixture was extracted twice with dichloromethane (100 mL×2). The organic phase were combined and washed successively with water (100 mL) mad saturated brine (100 mL). The organic phase was concentrated under reduced pressure to give a crude compound WX023-5, which was used directly in the next step without purification. $^1$H NMR (400 MHz, CDCl$_3$) δ=8.32 (d, J=2.0 Hz, 1H), 7.59 (d, J=2.3 Hz, 1H), 4.40 (dd, J=6.3, 10.0 Hz, 1H), 4.10 (t, J=10.8 Hz, 11H), 3.88-3.71 (m, 4H).

Step 6: Synthesis of Compound WX023

To a round bottom flask was added N,N-dimethylacetamide (5 mL) at 25° C. WX023-5 (288 mg, 999.43 µmol, 1 eq), $T_3P$ (954.00 mg, 1.50 mmol, 891.59 µL, 50% purity, 1.5 eq), BB-8 (406.16 mg, 2.00 mmol, 2 eq) and DIPEA (387.50 mg, 3.00 mmol, 522.24 µL, 3 eq) were then slowly added. The reaction solution was continuously stirred at 25° C. under nitrogen for 2 hours. The reaction solution was slowly poured into water (100 mL), and the mixture was extracted with ethyl acetate (100 mL×2). The organic phases were combined and washed successively with water (100 mL) and saturated brine (100 mL). The organic phase was concentrated under reduced pressure to give a crude product. The crude product was purified by preparative HPLC (Column: Xtimate C18 100*30 mm*3 µm; Mobile phase: [water (0.225% FA)-ACN]; acetonitrile %: 42%-72%, 8 min) to give compound WX023. $^1$H NMR (400 MHz, CDCl$_3$) δ=8.77 (br d, J=7.0 Hz, 1H), 8.42 (d, J=2.0 Hz, 1H), 8.04 (s, 1H), 7.71 (d, J=2.0 Hz, 1H), 7.45-7.33 (m, 3H), 7.33-7.27 (m 0.2H), 5.40 (s, 2H), 5.21 (td, J=6.7, 11.3 Hz, 1H), 4.77 (dd, J=6.3, 9.5 Hz, 1H), 4.33 (dd, J=9.8, 11.0 Hz, 1H), 3.90 (s, 3H); LCMS m/z=475.0 [M+1]$^+$.

Example 24: WX024

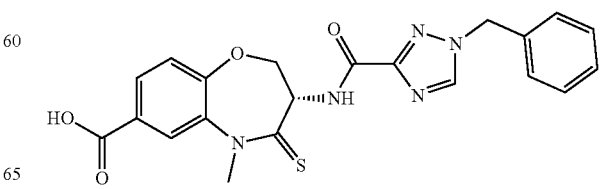

Route for Synthesis

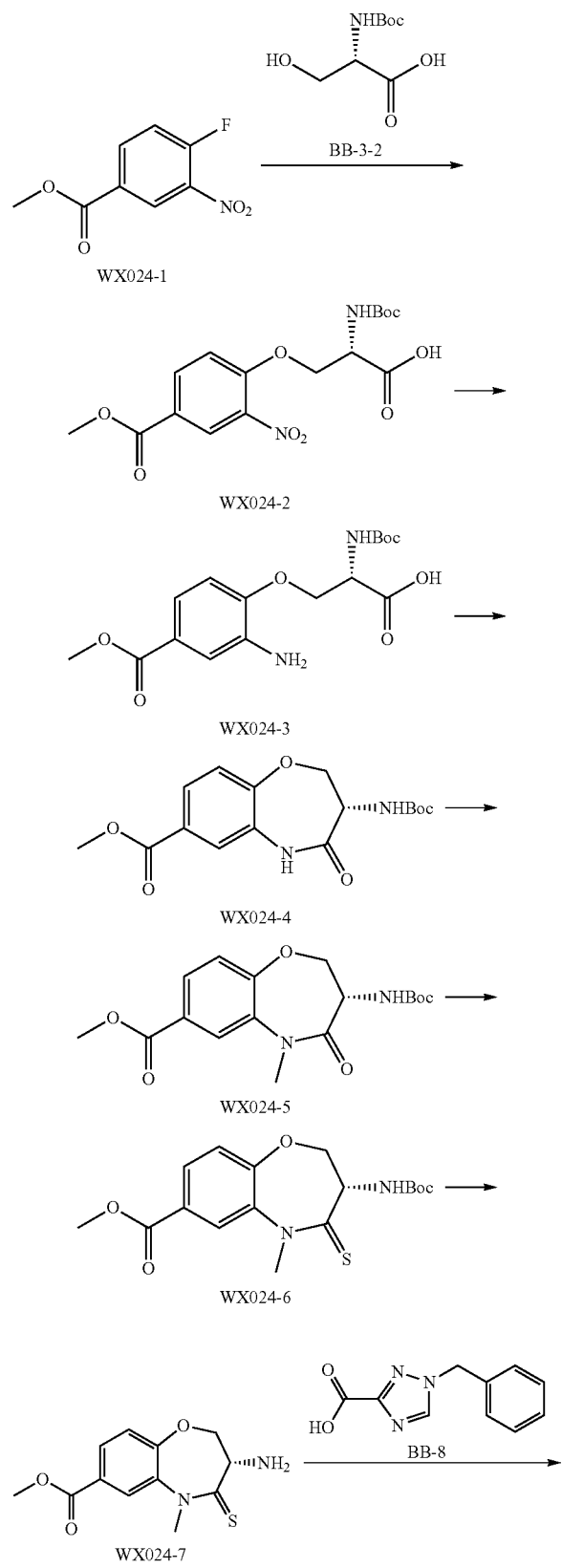

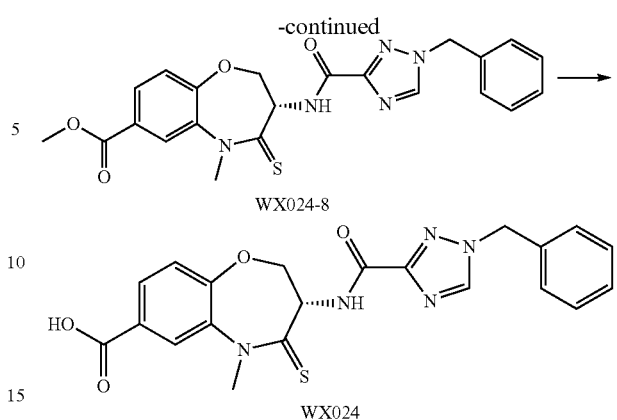

Step 1: Synthesis of Compound WX024-2

To a round bottom flask was added THF (100 mL). WX024-1 (10 g, 50.22 mmol, 1 eq), BB-3-2 (11.34 g, 55.24 mmol, 1.1 eq) and cesium carbonate (29.45 g, 90.39 mmol, 1.8 eq) were then slowly added. The mixture was continuously stirred at 65° C. for 16 hours. The reaction solution was poured into water (300 mL), and 2 M diluted hydrochoric acid was then added dropwise to adjust pH to 3. The mixture was extracted with ethyl acetate (500 mL×2). The organic phases were combined and washed with saturated brine (50 mL×2). The organic phase was concentrated under reduced pressure to give compound WX024-2. $^1$H NMR (400 MHz, CDCl$_3$) δ=8.46 (d, J=1.8 Hz, 11H), 8.20 (dd, J=2.0, 8.8 Hz, 1H), 7.12 (d, J=8.8 Hz, 1H), 5.62 (br d, J=8.0 Hz, 1H), 4.83-4.61 (m, 2H), 4.45 (dd, J=3.0, 9.3 Hz, 1H), 3.93 (s, 3H), 1.45 (s, 10H).

Step 2: Synthesis of Compound WX024-3

To a hydrogenation bottle was added MeOH (300 mL). WX024-2 (25.8 g, 67.13 mmol, 1 eq) and Pd/C (2.6 g, 26.02 mmol, 10% purity) were then slowly added. The atmosphere was replaced three times with argon gas, and the mixture was continuously stirred at 30° C. under H$_2$ (40 Psi) atmosphere for 24 hours. A new spot appeared by TLC (petroleum ether:ethyl acetate:acetic acid=1:1:0.1) monitoring. The reaction solution was filtered through Celite, and the filtrate was concentrated under reduced pressure to give compound WX024-3. $^1$H NMR (400 MHz, CDCl$_3$) δ=7.50-7.44 (m, 11H), 7.39 (br s, 1H), 6.70 (d, J=8.5 Hz, 1H), 6.53 (br s, 2H), 6.00 (br d, J=7.5 Hz, 1H), 4.73 (br d, J=7.0 Hz, 1H), 4.43 (br d, J=8.5 Hz, 1H), 4.31-4.24 (m, 1H), 3.85 (s, 3H), 1.41 (s, 9H).

Step 3: Synthesis of Compound WX024-4

To a round bottom flask was added ethyl acetate (200 mL). WX024-3, T$_3$P (33.67 g, 52.91 mmol, 31.47 mL, 50% purity, 1.5 eq), and DIEA (13.68 g, 105.83 mmol, 18.43 mL, 3 eq) were then slowly added, and the mixture was continuously stirred at 25° C. for 2 hours. The reaction solution was extracted with water (200 mL), and the layers were separated. The aqueous phase was extracted with ethyl acetate (200 mL×2). The organic phases were combined, washed with saturated brine (100 mL×2), and concentrated under reduced pressure. The crude product was purified by silica gel column chromatography (petroleum ether:ethyl acetate=100:1~1:1) to give compound WX024.4. $^1$H NMR (400 MHz, CDCl$_3$) δ=8.15 (br s, 1H), 7.80 (dd, J=2.0, 8.5 Hz, 11H), 7.73 (d, J=2.0 Hz, 1H), 7.13 (d, J=8.3 Hz, 1H), 5.62 (br d, J=5.3 Hz, 1H), 4.71-4.59 (m, 2H), 4.33-4.23 (m, 11), 3.95-3.89 (m, 3H), 1.43 (s, 9H).

Step 4: Synthesis of Compound WK024-5

To a round bottom flask was added N,N-dimethylformamide (200 mL). WX024-4 (17 g, 50.54 mmol, 1 eq), cesium carbonate (49.40 g, 151.63 mmol, 3 eq) and iodomethane (21.52 g, 151.63 mmol, 9.44 mL, 3 eq) were then slowly added, and the mixture was continuously stirred at 25° C. for 2 hours. Water (300 mL) was added to the reaction solution, and the mixture was extracted with ethyl acetate (300 mL×2). The organic phases were combined, washed with saturated brine (100 mL×2), and concentrated under reduced pressure. The crude product was purified by silica gel column chromatography (petroleum ether:ethyl acetate=100:1~1:1) to give compound WX024-5. $^1$H NMR (400 MHz, CDCl$_3$) δ=7.92-7.83 (m, 2H), 7.18 (d, J=8.4 Hz, 1H), 5.50 (br d, J=6.1 Hz, 1H), 4.72-4.52 (m, 2H), 4.28-4.17 (m, 1H), 3.92 (s, 3H), 3.42 (s, 3H), 1.38 (s, 9H).

Step 5: Synthesis of Compound WX024-6

To a round bottom flask was added toluene (40 mL). WX024-5 (4.01 g, 11.45 mmol, 1 eq), Lawsson's reagent (5.09 g, 12.59 mmol, 1.1 eq) and Boc$_2$O (10.60 g, 48.55 mmol, 11.15 mL, 4.24 eq) were then slowly added. The mixture was heated to 110° C., and stirred for 12 hours. The reaction solution was slowly poured into saturated brine (30 mL), and the mixture was extracted with ethyl acetate (100 mL×2). The organic phases were combined, washed with saturated brine (30 mL×2), and concentrated under reduced pressure to give a crude product. The crude product was purified by silica gel column chromatography (petroleum ether:ethyl acetate=100:1~1:1) to give compound WX024-6. $^1$H NMR (400 MHz, CDCl$_3$) δ=7.99-7.92 (m, 2H), 7.21 (d, J=8.3 Hz, 1H), 6.02 (br d, J=7.8 Hz, 1H), 4.80-4.69 (m, 1H), 4.53 (dd, J=6.3, 9.5 Hz, 1H), 4.22 (dd, J=9.5, 11.3 Hz, 1H), 3.94 (s, 3H), 3.86 (s, 3H), 1.46-1.33 (m, 9H).

Step 6: Synthesis of Compound WX024-7

To a round bottom flask was added ethyl acetate (10 mL). WX024-6 (500 mg, 1.36 mmol, 1 eq) and HCV/ethyl acetate (4 M, 10 mL, 29.31 eq) were then slowly added, and the mixture was continuously stirred at 25° C. for 2 hours. The reaction solution was concentrated under reduced pressure to give compound WX024-7. $^1$H NMR (400 MHz, CDCl$_3$) δ=8.04-7.89 (m, 2H), 7.28 (br s, 1H), 4.93 (br s, 1H), 4.63 (br s, 1H), 4.44 (br s, 1H), 3.93 (s, 3H), 3.88-3.85 (m, 1H), 3.81 (s, 3H).

Step 7: Synthesis of Compound WX024-8

To a round bottom flask was added N,N-dimethylformamide (5 mL). WX024-7 (245 mg, 809.18 µmol, 1 eq. HCl). BB-8 (164.42 mg, 809.18 µmol, 1 eq), HATU (461.51 ng, 1.21 mmol, 1.5 eq) and DIPEA (313.74 mg, 2.43 mmol, 422.83 µL, 3 eq) were then slowly added, and the mixture was continuously stirred at 25° C. for 2 hours. The reaction solution was poured into water (20 mL), and the mixture was extracted with ethyl acetate (20 mL×2). The organic phases were combined, washed with saturated brine (5 mL×2), and concentrated under reduced pressure to give a crude product. The crude product was purified by silica gel column chromatography (petroleum ether:ethyl acetate=100:1~1:100) to give compound WX024-8. $^1$H NMR (400 MHz, CDCl$_3$) δ=8.70 (br d, J=7.3 Hz, 1H), 8.02-7.94 (m, 3H), 7.42-7.34 (m, 3H), 7.31-7.28 (m, 2H), 5.39 (s, 2H), 5.20 (td, J=6.8, 11.0 Hz, 1H), 4.72 (dd, 3=6.5, 9.4 Hz, 1H), 4.31 (t, J=10.3 Hz, 1H), 3.95 (s, 3H), 3.89 (s, 3H).

Step 8: Synthesis of Compound WX024

To a round bottom flask were added THF (4 mL) and H$_2$O (1 mL). WX024-8 (50 mg, 110.74 µmol, 1 eq) and LiOH.H$_2$O (4.65 mg, 110.74 µmol, 12.79 µL, 1 eq) were then slowly added, and the mixture was continuously stirred at 25° C. for 2 hours. The reaction solution was separated by HPLC(Column: Phenomenex Gemini-NX 80*40 mm*3 µm; Mobile phase: [water (0.05% NH$_3$.H$_2$O+10 mM NH$_4$HCO$_3$)-ACN]; acetonitrile %:11%-31%, 8 min) to give compound WX024. $^1$H NMR (400 MHz, CDCl$_3$) δ=8.78 (br s, 1H), 8.18-7.82 (m, 3H), 7.36 (br s, 5H), 5.64-5.32 (m, 2H), 5.26 (br s, 1H), 4.72 (br s, 1H), 4.32 (br s, 1H), 3.86 (br s, 3H); LCMS m/z=438.1 [M+1]$^+$.

Example 25: WX025

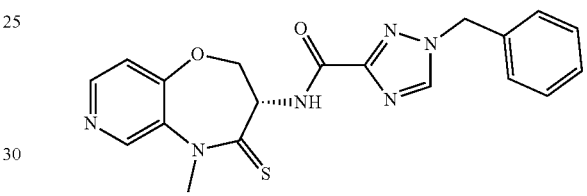

Route for Synthesis

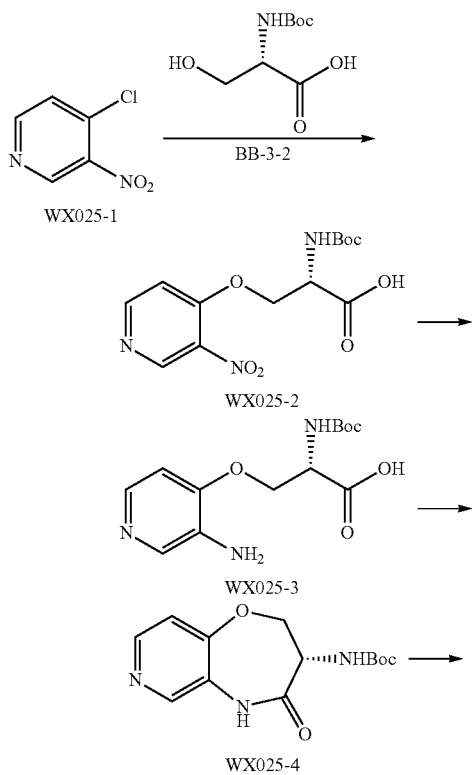

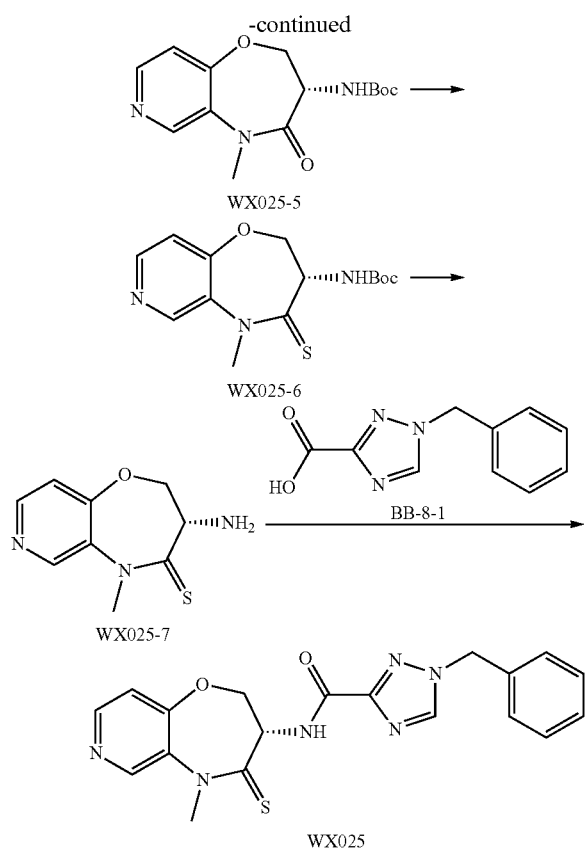

Step 1: Synthesis of Compound WX025-2

NaH (2.78 g, 69.38 mmol, 60% purity, 2.2 eq) was added to a solution of BB-3-2 (7.12 & 34.69 mmol, 1.1 eq) in N,N-dimethylformamide (80 mL) at 0° C. under nitrogen, and the mixture was reacted for 2 hours. The reaction solution was placed in an ice-water bath, and WX025-1 (5 g, 31.54 mmol, 1 eq) was added to the above solution. The reaction solution was heated to 25° C. and reacted for 12 hours. The reaction solution was slowly added to ice water (100 mL), and the mixture was extracted with ethyl acetate (150 mL×2). The aqueous phase was adjusted to a pH of 5-6 with 1 M HCl, and extracted with ethyl acetate (150 mL×2). The organic phases were combined, washed with saturated brine, dried over anhydrous sodium sulfate, and filtered. The filtrate was concentrated under reduced pressure to give compound WX025-2. LCMS m/z=328.1 [M+1]$^+$.

Step 2: Synthesis of Compound WX025-3

Pd/C (3 g, 5% purity) was added to a solution of WX025-2 (9 g, 27.30 mmol, 1 eq) in ethyl acetate (60 mL) and methanol (30 mL). The atmosphere was replaced three times with H$_2$, and the mixture was reacted at 25° C. wider H$_2$ (15 Psi) atmosphere for 12 hours. The reaction solution was filtered through Celite, and the filtrate was concentrated under reduced pressure to give compound WX025-3. LCMS m/z=298.1 [M+1]$^+$.

Step 3: Synthesis of Compound WX025-4

T$_3$P (20.87 g, 32.79 mmol, 19.50 mL, 50% purity, 1.5 eq) was added to a solution of DIPEA (7.06 g, 54.66 mmol, 9.52 mL, 2.5 eq) and WX025-3 (6.5 g, 21.86 mmol, 1 eq) in N,N-dimethylformamide (200 mL), and the mixture was reacted at 25° C. for 3 hours. Water (200 mL) was added to the reaction solution in an ice bath, and the mixture was extracted with ethyl acetate (200 mL×2). The organic phases were combined, washed with saturated brine, dried over anhydrous sodium sulfate, and filtered. The filtrate was concentrated under reduced pressure to give a crude product. The crude product was purified by column chromatography (petroleum ether:ethyl acetate=10:1-1:2) to give compound WX025-4. $^1$H NMR (400 MHz, CDCl$_3$) δ=8.37 (br s, 1H), 8.20-8.31 (m, 2H), 6.97 (d, J=5.70 Hz, 1H), 5.69 (br d, J=4.38 Hz, 1H), 4.54-4.71 (m, 2H), 4.22-4.35 (m, 1H), 1.45-1.52 (m, 9H); LCMS m/z=280.1[M+1]$^+$.

Step 4: Synthesis of Compound WX025-5

Iodomethane (384.21 mg, 2.71 mmol, 168.51 μL, 1.05 eq) was added to a solution of WX025-4 (0.72 g, 2.58 mmol, 1 eq) and cesium carbonate (1.01 g, 3.09 mmol, 1.2 eq) in tetrahydrofuran (14 mL), and the mixture was reacted at 20° C. for 12 hours. Water (25 mL) and ethyl acetate (25 mL) were added to the reaction solution, and the layers were separated. The aqueous phase was extracted with ethyl acetate (25 mL×2). The organic phases were combined, washed with saturated brine, dried over anhydrous sodium sulfate, and filtered. The filtrate was concentrated under reduced pressure to give a crude product. The crude product was purified by column chromatography (dichloromethane:methanol=10:0-10:1) to give compound WX025-5. $^1$H NMR (400 MHz, CDCl$_3$) δ=8.50 (s, 1H), 8.39 (d, J=5.27 Hz, 1H), 7.06 (d, J=5.40 Hz, 1H), 5.54 (br d, J=6.02 Hz, 1H), 4.56-4.73 (m, 2H), 4.25-4.37 (m, 1H), 3.47 (s, 3H), 1.41 (s, 9H); LCMS m/z=294.1 [M+1]$^+$.

Step 5: Synthesis of Compound WX025-6

Lawwson's reagent (110.32 mg, 272.74 μmol, 0.8 eq) was added to a solution of WX025-5 (0.1 g, 340.93 μmol, 1 eq) in toluene (2 mL) at 20° C., and the mixture was reacted at 90° C. for 12 hours. Ethyl acetate (5 mL) was added to the reaction solution. The mixture was filtered, and the filtrate was concentrated under reduced pressure to give a crude product. The crude product was purified by column chromatography (petroleum ether:ethyl acetate=10:1-1:2) to give compound WX025-6. LCMS m/z=310.1 [M+1]$^+$.

Step 6: Synthesis of Compound WX025-7

HCV/ethyl acetate (3 mL) was added to a solution of WX025-6 (53 mg, 171.31 μmol, 1 eq) in ethyl acetate (3 mL), and the mixture was reacted at 25° C. for 2 hours. The reaction solution was concentrated under reduced pressure to give compound WX025-7. LCMS m/z=210.1 [M+1]$^+$.

Step 7: Synthesis of Compound WX025

DIPEA (77.82 mg, 602.10 μmol, 104.87 μL, 3 eq) and T$_3$P (127.72 mg, 401.40 μmol, 119.36 μL, 2 eq) were added to a solution of WX025-7 (42 mg, 200.70 μmol, 1 eq) and 3-8 (61.17 mg, 301.05 μmol, 1.5 eq) in N,N-dimethylformamide (3 mL), and the mixture was reacted at 25° C. for 2 hours. Water (S mL) and ethyl acetate (S mL) were added to the reaction solution, and the layers were separated. The aqueous phase was extracted with ethyl acetate (5 mL×2). The organic phases were combined, washed with saturated brine, dried over anhydrous sodium sulfate, and filtered. The filtrate was concentrated under reduced pressure to give a crude product. The crude product was separated by preparative HPLC (Column: Phenomenex Luna C18 150 mm*30 mm*5 μm; Mobile phase: [water (0.05% HCl)-ACN]; acetonitrile %: 20%-50%, 12 min) to give compound WX025. $^1$H NMR (400 MHz, DMSO-$d_6$) δ=8.83 (d, J=8.16 Hz, 2H), 8.64-8.65 (m, 1H), 8.67 (d, J=7.72 Hz, 1H), 8.54 (d, J=5.28 Hz, 1H), 7.26-7.42 (m, 6H), 5.49 (s, 2H), 5.04 (dt, J=11.24, 6.84 Hz, 1H), 4.44-4.64 (m, 2H), 3.83 (s, 3H); LCMS m/z=395.2 [M+1]$^+$.

Example 26: WX026

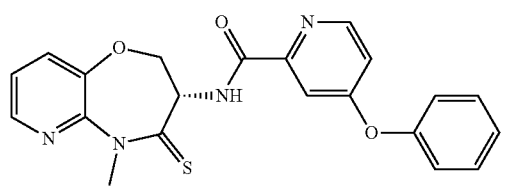 [SMILES: CN1C(=S)[C@@H](NC(=O)c2cc(Oc3ccccc3)ccn2)COc2cccnc21]

Route for Synthesis

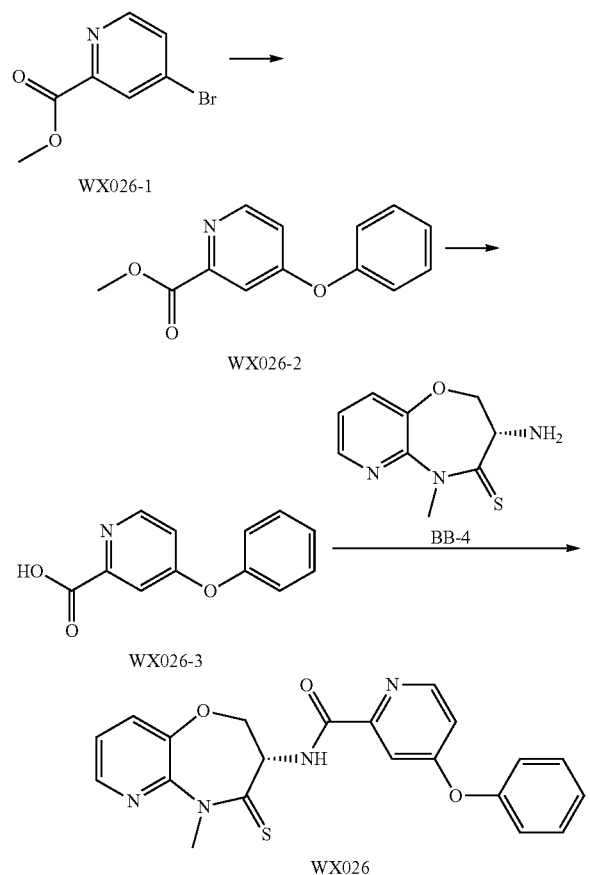

Step 1: Synthesis of Compound WX026-2

To a solution of WX026-1 (1 g, 4.63 mmol, 1 eq) and phenol (871.27 mg, 9.26 mmol, 814.27 μL, 2 eq) in N,N-dimethylformamide (10 mL) were added potassium carbonate (1.28 g, 9.26 mmol, 2 eq), cuprous bromide (66.40 mg, 462.89 μmol, 14.10 μL, 0.1 eq), and acetylacetone (23.17 mg, 231.45 μmol, 23.77 μL, 0.05 eq), and the mixture was stirred at 90° C. for another 10 hours. Water (100 mL) was added to the reaction solution, and the mixture was extracted with ethyl acetate (30 mL×3). The organic phases were combined, dried over anhydrous sodium sulfate, and filtered, and the filtrate was concentrated under reduced pressure to give compound WX026-2. LCMS m/z=230.2 [M+1]$^+$.

Step 2: Synthesis of Compound WX026-3

To a solution of WX026-2 (0.45 g, 1.96 mmol, 1 eq) in tetrahydrofuran (5 mL) was added a solution of LiOH.H$_2$O (164.76 mg, 3.93 mmol, 2 eq) in water (1 mL), and the mixture was stirred at 18° C. for 1 hour. Ethyl acetate (20 mL) was added to the reaction solution, and the mixture was adjusted to a pH of 2 with 2N hydrochloric acid. The organic phase was dried over hydrous sodium sulfate, filtered, and concentrated under reduced pressure to give compound WX026-3. LCMS m/z=216.1 [M+1]$^+$.

Step 3: Synthesis of Compound WX026

To a solution of BB-4 (0.3 g, 679.40 μmol, 1 eq) in N,N-dimethylformamide (2 ML) were added WX026-3 (153.52 mg, 713.37 μmol, 1.05 eq), DIPEA (263.42 mg, 2.04 mmol, 355.01 μL, 3 eq), and T$_3$P (648.52 mg, 1.02 mmol, 606.09 μL, 30% purity, 1.5 eq) at 18° C., and the mixture was stirred for 1 hour. The reaction solution was purified by HPLC (Column: Phenomenex Luna C18 150 mm*30 mm*5 μm; Mobile phase: [water (0.05% HCl)-ACN]; acetonitrile %: 20%-50%, 12 min) to give compound WX026. $^1$H NMR (400 MHz, DMSO-$d_6$) δ=8.84 (s, 1H), 8.60 (d, J=7.89 Hz, 1H), 8.36 (dd, J=1.32, 4.82 Hz, 1H), 7.70 (dd, J=1.53, 8.11 Hz, 11), 7.25-7.46 (m, 5H), 5.49 (s, 2H), 4.85 (td, J=7.67, 11.40 Hz, 1H), 4.63-4.75 (m, 1H), 4.51 (dd, J=7.45, 9.65 Hz, 1H), 4.03 (br s, 3H); LCMS m/z=407.1 [M+1]$^+$.

Example 27: WX027

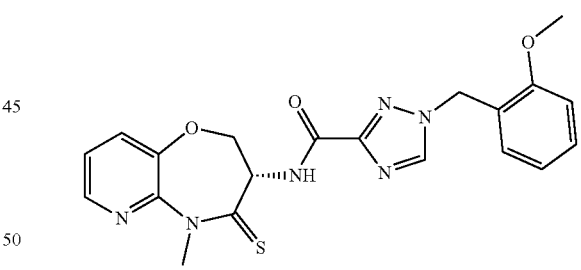

Route for Synthesis

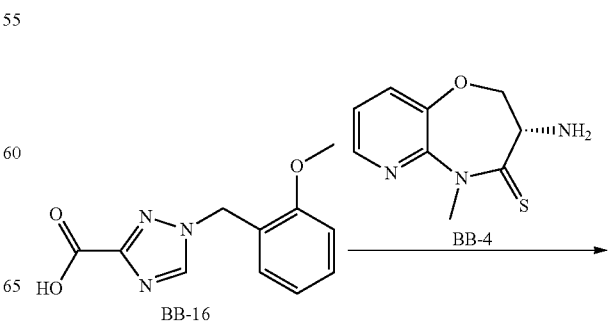

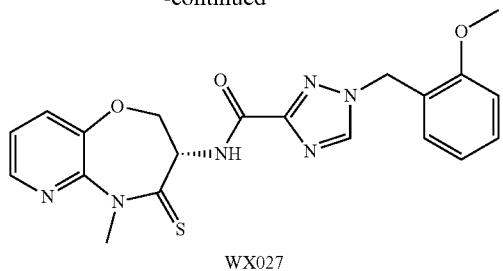

WX027

Step 1: Synthesis of Compound WX027

To a round bottom flask was added N,N-dimethylacetamide (5 mL) at 25° C. BB-4 (20 mg, 45.29 μmol, 1 eq), T₃P (43.23 mg, 67.94 μmol, 40.41 μL, 50% purity, 1.5 eq). BB-16 (15.85 mg, 67.94 μmol, 1.5 eq) and DIPEA (17.56 mg, 135.88 μmol, 23.67 μL, 3 eq) were then slowly added, and the reaction solution was continuously stirred at 25° C. under nitrogen for 2 hours. The reaction solution was slowly poured into water (100 mL), and the mixture was extracted with ethyl acetate (100 mL×2). The organic phases were combined, washed successively with water (100 mL) and saturated brine (100 mL), and concentrated under reduced pressure to give a crude product. The crude product was separated by preparative HPLC (Column: Xtimate C18 100*30 mm*3 μm; Mobile phase: [water (0.225% FA)-ACN]; acetonitrile %: 42%-72%, 8 min) to give compound WX027. ¹H NMR (400 MHz, CDCl₃) δ8.78 (br d, J=7.0 Hz, 1H), 8.47-8.25 (m, 1H), 8.08 (s, 1H), 7.60-7.50 (m, 1H), 7.35 (t, J=7.9 Hz, 1H), 7.32-7.26 (m, 2H), 6.96 (t, J=7.4 Hz, 1H), 6.91 (d, J=8.0 Hz, 1H), 5.38 (s, 2H), 5.20 (td, J=6.7, 11.4 Hz, 1H), 4.77 (dd, J=6.3, 9.5 Hz, 1H), 4.38-4.23 (m, 1H), 3.92 (s, 3H), 3.84 (s, 3H); LCMS m/z=425.1 [M+1]⁺.

Example 28: WX028

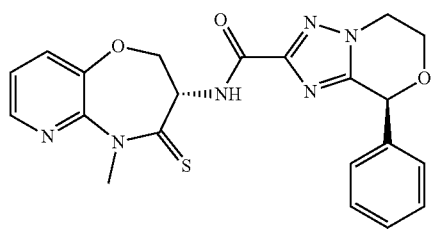 [SMILES: CN1C(=S)[C@@H](NC(=O)c2nc3n(n2)CCO[C@H]3c2ccccc2)COc2cccnc21]

Route for Synthesis

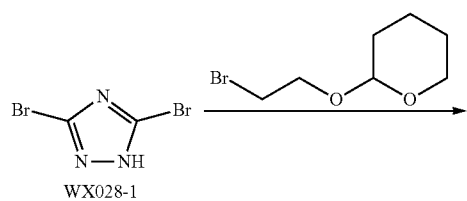

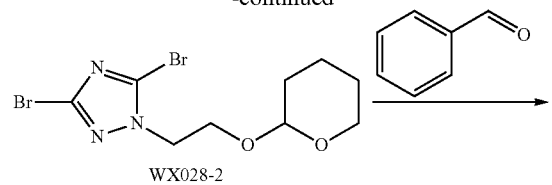

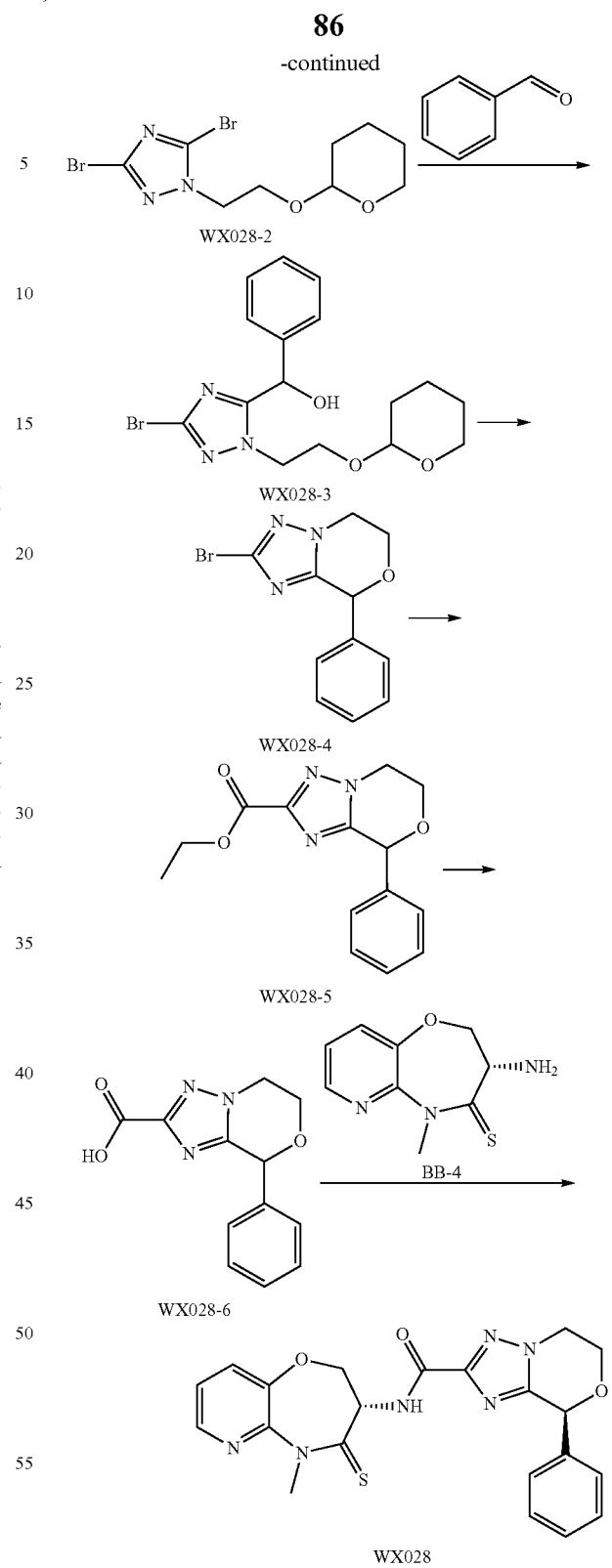

Step 1: Synthesis of Compound WX028-2

To a round bottom flask was added MeCN (80 mL), and WX029-1 (4 g, 17.63 mmol, 1 eq) was then slowly added. After dissolved, 2-(2-bromoethoxy)tetrahydropyran (4.42 g, 21.16 mmol, 3.21 mL, 1.2 eq) and DIPEA (2.51 g, 19.40 mmol, 3.38 mL, 1.1 eq) were added, and the mixture was heated to 90° C. and continuously stirred for 3 hours. Water (100 mL) was added to the reaction solution, and the mixture was extracted with ethyl acetate (100 mL×2). The organic phases were combined, washed with saturated brine (30 mL×2), and concentrated under reduced pressure to give a crude product. The crude product was purified by silica gel column chromatography (petroleum ether:ethyl acetate=100:1~1:1) to give compound WX02-2. $^1$H NMR (400 MHz, CDCl$_3$) δ=4.55 (br s, 1H), 4.34 (t, J=5.3 Hz, 2H), 4.12-4.06 (m, 1H), 3.79 (td, J=5.4, 10.8 Hz, 1H), 3.64-3.53 (m, 1H), 3.50-3.41 (m, 1H), 1.76-1.58 (m, 2H), 1.57-1.43 (m, 4H).

Step 2: Synthesis of Compound WX028-3

To a round bottom flask was added THF (50 mL), and WX02-2 (4.99 g, 14.06 mmol, 1 eq) was then slowly added. The mixture was cooled to −78° C. and n-butyllithium (2.5 M, 6.75 mL, 1.2 eq) was added. The mixture was stirred for 1 hour, and benzaldehyde (2.98 g, 28.11 mmol, 2.84 mL, 2 eq) was slowly added. The mixture was stirred at −78° C. for 0.5 hour, md then heated to −50° C. and stirred for another 0.5 hours. After the completion of the reaction, the reaction solution was poured into a mixed solution of saturated ammonium chloride (200 mL) and ethyl acetate (200 mL), and the layers were separated. The aqueous phase was extracted with ethyl acetate (200 mL). The organic phases were combined, washed with saturated brine (50 mL×2), and concentrated under reduced pressure to give a crude product. The crude product was purified by silica gel column chromatography (petroleum ether:ethyl acetate=100:1~1:1) to give compound WX028-3. $^1$H NMR (400 MHz, CDCl$_3$) δ=7.45-7.29 (m, 5H), 6.09 (d, J=5.8 Hz, 1H), 4.51 (br s, 1H), 4.34 (ddq, J=3.5.5.3, 7.2 Hz, 1H), 4.26-4.15 (m, 1H), 4.07-3.97 (m, 1H), 3.78-3.56 (m, 2H), 3.47 (dt, J=5.9, 10.7 Hz, 1H), 1.85-1.64 (m, 2H), 1.52 (br d, J=6.3 Hz, 4H).

Step 3: Synthesis of Compound WX028-4

To a round bottom flask was added toluene (50 mL). WX028-3 (4.7 g, 12.30 mmol, 1 eq) and TsOH.H$_2$O (3.04 g, 15.98 mmol, 1.3 eq) were then slowly added, and the mixture was continuously stirred at 110° C. for 5 hours. Water (50 mL) was added to the reaction solution, and the mixture was extracted with ethyl acetate (50 mL×2). The organic phases were combined, washed with saturated brine (20 mL×2), and concentrated wider reduced pressure.

The crude product was purified by silica gel column chromatography (petroleum ether-ethyl acetate=100:1~1:1) to give compound WX028-4. $^1$H NMR (400 MHz, CDCl$_3$) δ=7.45-7.34 (m, 5H), 5.87 (s, 1H), 4.33-4.27 (m, 2H), 4.19-4.06 (m, 2H).

Step 4: Synthesis of Compound WX028-5

To an autoclave was added EtOH (20 mL). WX028-4 (500 mg, 1.78 mmol, 1 eq), Pd(dppf)Cl$_2$ (261.21 mg, 336.99 μmol, 0.2 eq) and TEA (1.81 g, 17.85 mmol, 2.48 mL, 10 eq) ware then slowly added. The atmosphere was replaced three times with argon gas, and the mixture was continuously stirred at 100° C. wider CO (1 MPa) atmosphere for 24 hours. Water (50 mL) was added to the reaction solution, and the mixture was extracted with ethyl acetate (50 mL×2). The organic phases were combined, washed with saturated brine (10 mL×2), mid concentrated under reduced pressure to give a crude product. The crude product was separated by preparative HPLC (Column: Xtimate C18 100*30 mm*3 μm; Mobile phase: [water (0.225% FA)-ACN]; acetonitrile %: 42%-72%, 8 min) to give compound WX0285. $^1$H NMR (400 MHz, CDCl$_3$) δ=7.47-7.31 (m, 5H), 6.02-5.93 (m, 1H), 4.54-4.38 (m, 4H), 4.34-4.25 (m, 1H), 4.19-4.10 (m, 1H), 1.42 (t, J=7.1 Hz, 3H).

Step 5: Synthesis of Compound WX02&-6

To a round bottom flask were added THF (4 mL) and H$_2$O (1 mL). WX028-4 (260 ag, 951.38 μmol, 1 eq) and LiOH.H$_2$O (119.77 mg, 2.85 mmol, 3 eq) were then slowly added. The mixture was continuously stirred at 25° C. for 1 hour. The reaction solution was concentrated to dryness by rotary evaporation under reduced pressure to remove THF, 1 M aqueous HCl solution was added dropwise to adjust pH to 3, and the mixture was filtered to give a product WX028-6. $^1$H NMR (400 MHz, DMSO-d$_6$) δ=7.40 (s, 5H), 6.00 (s, 1H), 4.50-4.40 (m, 1H), 4.40-4.29 (m, 2H), 4.26-4.11 (m, 1H).

Step 6: Synthesis of Compound WX021-7

To a round bottom flask was added N,N-dimethylformamide (1 mL). WX0284 (30 mg, 122.33 μmol, 1 eq), BB-4 (54.02 mg, 122.33 μmol, 1 eq), T$_3$P (116.77 mg, 183.50 μmol, 109.13 μL, 50% purity, 1.5 eq) and DIPEA (47.43 mg, 366.99 μmol, 63.92 μL, 3 eq) were then slowly added, and the mixture was continuously stirred at 25° C. for 2 hours. The reaction solution was separated by preparative HPLC (Column: Xtimate C18 100*30 mm*3 μm; Mobile phase: [water (0.225% FA)-ACN]; acetonitrile %: 35%-65%, 8 min) to give a racemate of compound WX028, which was then resolved by chiral SFC (Column: DAICEL CHIRALCEL OD (250 mm*30 mm, 10 μm); Mobile phase: [Neu-ETOH]; ethanol %: 45%-45%, min) to give the active isomer WX02. $^1$H NMR (400 MHz, CDCl$_3$) δ=8.65 (br d, J=7.1 Hz, 1H), 8.37 (br d, J=3.3 Hz, 1H), 7.56 (br d, J=7.8 Hz, 1H), 7.48-7.36 (m, 5H), 7.32-7.27 (m, 1H), 5.99 (s, 1H), 5.33-5.16 (m, 1H), 4.74 (dd, J=6.4, 9.5 Hz, 1H), 4.40 (br d, J=4.3 Hz, 2H), 4.36-4.24 (m, 2H), 4.19-4.07 (m, 1H), 3.92 (s, 3H); LCMS m/z=437.1 [M+1]$^+$.

Example 29: WX029

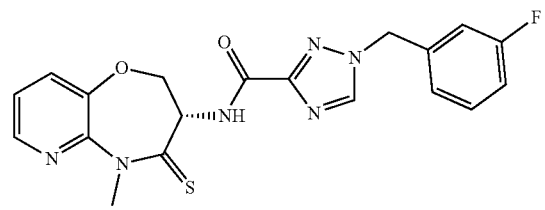 [SMILES: CN1C(=S)[C@@H](NC(=O)c2ncn(Cc3cccc(F)c3)n2)COc2cccnc21]

Route for Synthesis

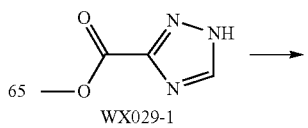

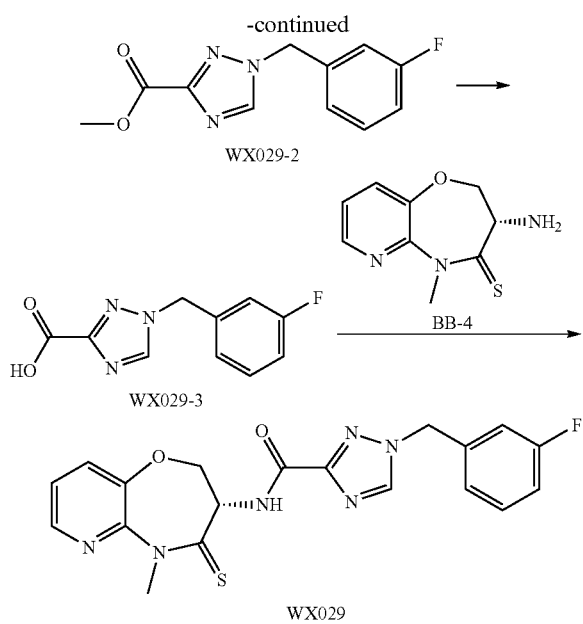

Step 1: Synthesis of Compound WX029-2

To a round bottom flask was added MeCN (20 mL) at 25° C., and WX029-1 (2.02 g, 15.89 mmol, 1 eq), K₂CO₃ (4.39 g, 31.79 mmol, 2 eq) and 3-fluorobenzyl chloride (2.76 g, 19.07 mmol, 2.28 mL, 1.2 eq) were then slowly added. The reaction solution was continuously stirred at 60° C. under nitrogen for 12 hours. The reaction solution was slowly poured into water (100 mL) and the mixture was extracted with ethyl acetate (100 mL×2). The organic phases were combined, washed successively with water (100 mL) and saturated brine (100 mL), and concentrated under reduced pressure to give a crude product. The crude product %% purified by silica gel column chromatography (petroleum ether:ethyl acetate=100:20~100:75) to give compound WX029-2. ¹H NMR (400 MHz, CDCl₃) δ=8.14 (s, 1H), 7.36 (dt, J=5.9.8.0 Hz, 1H), 7.11-7.03 (m, 2H), 6.99 (br d, J=9.0 Hz, 1H), 5.42 (s, 2H), 4.14-3.89 (m, 3H).

Step 2: Synthesis of Compound WX029-3

To a round bottom flask were added THF (14 mL) and H₂O (2 mL) at 25° C., md WX029-2 and LiOH.H₂O (642.21 mg, 15.31 mmol, 3 eq) were then slowly added. The reaction solution was continuously stirred at 25° C. wider nitrogen for 1 hour. The reaction solution was adjusted to a pH of 6~7 with diluted hydrochloric acid (1 M), and the precipitate was filtered and dried to give compound WX029-3.

Step 3: Synthesis of Compound WX029

To a round bottom flask was added N,N-dimethylacetamide (5 mL) at 25° C., aid WX029-3 (15.03 mg, 67.94 umol, 1.5 eq), T₃P (43.23 mg, 67.94 μmol, 40.41 μL, 50% purity, 1.5 eq), BB-4 (15.03 mg, 67.94 μmol, 1.5 eq) and DIPEA (17.56 mg, 135.87 μmol, 23.67 μL, 3 eq) were then slowly added. The reaction solution was continuously stirred under nitrogen for 2 hours. The reaction solution was slowly poured into water (100 mL), and the mixture was extracted with ethyl acetate (100 mL×2). The organic phases were combined, washed successively with water (100 mL) and saturated brine (100 mL), and concentrated under reduced pressure to give a crude product. The crude product was purified by preparative HPLC (Column: Xtimate C18 100*30 mm*3 μm; Mobile phase: [water (0.225% FA)-ACN]; acetonitrile %: 35%-65%, 8 min) to give a product WX029. ¹H NMR (400 MHz, CDCl₃) δ=8.83 (br d, J=7.0 Hz, 1H), 8.37 (d, J=3.8 Hz, 11H), 8.10 (s, 1H), 7.57 (d, J=8.0 Hz, 1H), 7.40-7.27 (m, 2H), 7.15-6.87 (m, 3H), 5.40 (s, 2H), 5.29-5.07 (m, 1H), 4.79 (dd, J=6.3, 9.3 Hz, 1H), 4.32 (t, J=10.3 Hz, 1H), 3.93 (s, 3H); 19F NMR (376 MHz, CDCl₃) δ=−111.33 (s, 1F); LCMS m/z=413.0 [M+1]⁺.

Example 30: WX030

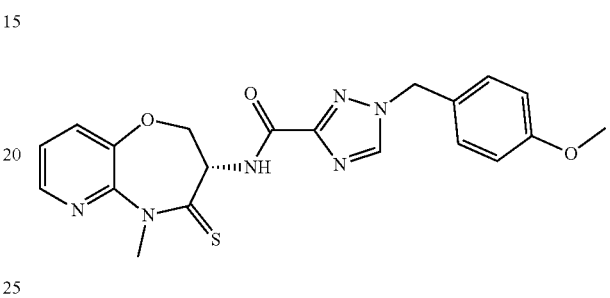

Route for Synthesis

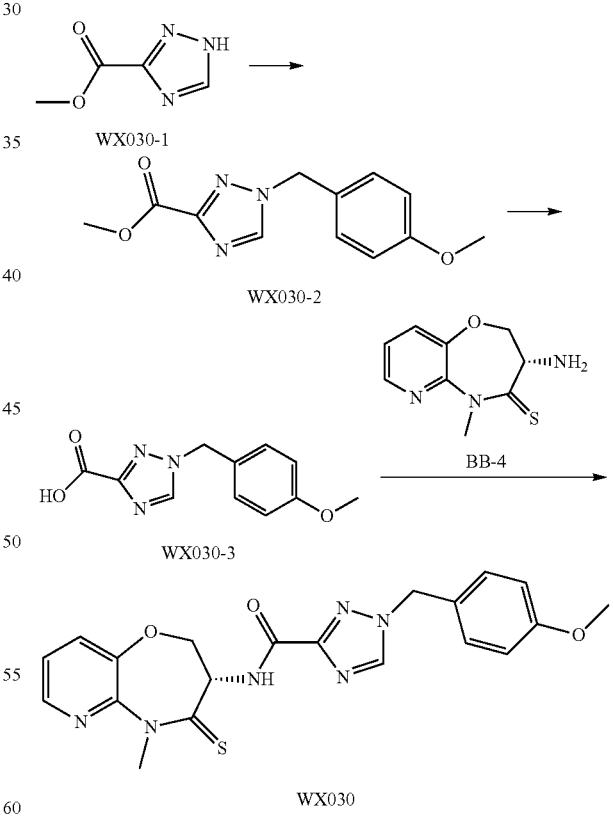

Step 1: Synthesis of Compound WX030-2

To a round bottom flask was added MeCN (20 mL) at 25° C., and WX030-1 (2.04 g, 16.05 mmol, 1 eq). K₂CO₃ (4.44 g, 32.10 mmol, 2 eq) and 4-methoxybenzyl chloride (3.02 g, 19.26 mmol, 2.62 mL, 1.2 eq) were then slowly added. The reaction solution was continuously stirred at 60° C. under nitrogen for 12 hours. The reaction solution was slowly poured into water (100 mL), and the mixture was extracted with ethyl acetate (100 mL×2). The organic phases were combined, washed successively with water (100 mL) and saturated brine (100 mL), and concentrated under reduced pressure to give a crude product. The crude product was purified by silica gel column chromatography (petroleum ether:ethyl acetate=100:20~100:75) to give compound WX030-2. $^1$H NMR (400 MHz, CDCl$_3$) δ=8.05 (s, 1H), 7.27 (d, J=8.8 Hz, 2H), 6.98-6.87 (m, 2H), 5.43-5.26 (m, 2H), 4.03-3.97 (m, 3H), 3.82 (s, 3H).

Step 2: Synthesis of Compound WX030-3

To a round bottom flak were added THF (14 mL) and H$_2$O (2 mL) at 25° C., and WX030-2 (1.5 g, 6.07 mmol, 1 eq) and LiOH.H$_2$O (763.68 mg, 18.20 mmol, 3 eq) were then slowly added. The reaction solution was continuously stirred at 25° C. under nitrogen for 1 hour. The reaction solution was adjusted to a pH of 6-7 with diluted hydrochloric acid (1 M), and the precipitate was filtered and dried to give compound WX030-3.

Step 3: Synthesis of Compound WX030

To a round bottom flask was added N,N-dimethylacetamide (5 mL) at 25° C. mid WX030-3 (15.84 ng, 67.94 μmol, 1.5 eq), T$_3$P (43.23 mg, 67.94 μmol, 40.41 μL, 30% purity, 1.5 eq), BB-4 (15.84 mg, 67.94 μmol, 1.5 eq) and DIPEA (17.36 mg, 135.87 μmol, 23.67 μL, 3 eq) were then slowly added, and the reaction solution was continuously stirred at 25° C. under nitrogen for 2 hours. The reaction solution was slowly poured into water (100 mL), and the mixture was extracted with ethyl acetate (100 mL×2). The organic phases were combined, washed successively with water (100 mL) and saturated brine (100 mL), and concentrated under reduced pressure to give a crude product. The crude product was separated by preparative HPLC (Column: Xtimate C18 100*30 mm*3 μm; Mobile phase: [water (0.225% FA)-ACN]; acetonitrile %: 35%-63%, 8 min) to give a product WX030. $^1$H NMR (400 MHz, CDCl$_3$) δ=8.80 (br s, 1H), 8.37 (br s, 1H), 7.98 (br s, 1H), 7.56 (br s, 1H), 7.38-7.28 (m, 1H), 7.26 (br s, 2H), 6.91 (br s, 2H), 5.41-5.10 (m, 3H), 4.78 (br s, 1H), 4.31 (br s, 1H), 3.98-3.73 (m, 6H); LCMS m/z=425.1 [M+1]$^+$.

Example 31: WX031

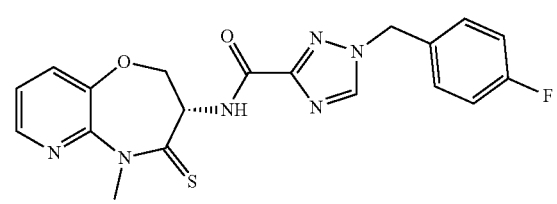 [SMILES: CN1C(=S)[C@@H](NC(=O)c2ncn(Cc3ccc(F)cc3)n2)COc2cccnc21]

Route for Synthesis

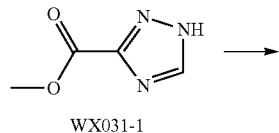

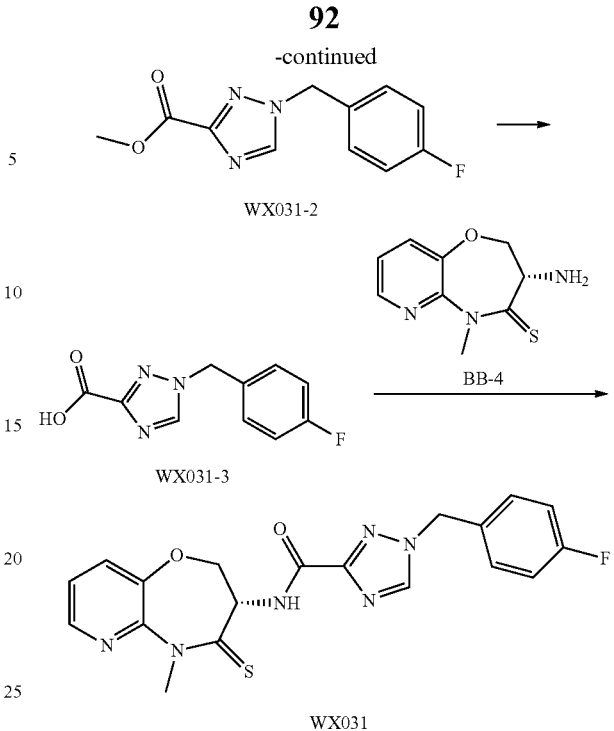

Step 1: Synthesis of Compound WX031-2

To a round bottom flask was added MeCN (20 mL). WX031-1 (1.5 g, 11.80 mmol, 1 eq), K$_2$CO$_3$ (2.45 g, 17.70 mmol, 1.5 eq) and 4-fluorobenzyl chloride (1.88 g, 12.98 mmol, 1.55 mL, 1.1 eq) were then added, and the mixture was continuously stirred at 50° C. for 12 hours. The reaction solution was poured into water (50 mL) and the mixture was extracted with ethyl acetate (30 mL×2). The organic phases were combined, washed with saturated brine (10 mL×2), and concentrated under reduced pressure to give a crude product. The crude product was purified by silica gel column chromatography (petroleum ether:ethyl acetate=100:1~1:100) to give compound WX031-2. $^1$H NMR (400 MHz, CDCl$_3$) δ=8.09 (s, 1H), 7.30 (dd, J=5.3, 8.3 Hz, 2H), 7.08 (t. J=8.5 Hz, 2H), 5.39 (s, 2H), 4.00 (s, 31).

Step 2: Synthesis of Compound WX031-3

To a round bottom flask were added THF (8 mL) and H$_2$O (2 mL). WX031-2 (1.06 g, 4.52 mmol, 1 eq) and LiOH.H$_2$O (569.16 mg, 13.56 mmol, 3 eq) were then added, and the mixture was continuously stirred at 25° C. for 2 hours. The reaction solution was concentrated under reduced pressure to remove THF. 1 M diluted hydrochloric acid solution was added dropwise to the reaction solution to adjust pH to less than 3, and the mixture was filtered to give compound WX031-3. $^1$H NMR (400 MHz, DMSO-d$_6$) δ=8.79 (s, 1H), 7.39 (dd, J=5.5, 8.8 Hz, 2H), 7.25-7.17 (m, 2H), 5.47 (s, 2H).

Step 3: Synthesis of Compound WK031

To a round bottom flask was added N,N-dimethylformamide (1 mL). WX031-3 (18.03 ng, 81.53 μmol, 1.2 eq). BB-4 (30 mg, 67.94 μmol, 1 eq), DIPEA (26.34 mg, 203.82 μmol, 35.50 μL, 3 eq) and T$_3$P (64.85 mg, 101.91 μmol, 60.61 μL, 50% purity, 1.5 eq) were then slowly added, and the mixture was continuously stirred at 25° C. for 2 hours.

The reaction solution was directly separated by HPLC (Column: Xtimate C18 100*30 mm*3 µm; Mobile phase: [water (0.225% FA)-ACN]; acetonitrile %: 40%-70%, 8 min) to give compound WX031. $^1$H NMR (400 MHz, CDCl$_3$) δ=8.81 (br d, J=7.3 Hz, 1H), 8.37 (dd, J=1.4, 4.6 Hz, 1H), 8.06 (s, 1H), 7.56 (dd, J=1.4, 7.9 Hz, 1H), 7.33-7.27 (m, 3H), 7.07 (t, J=8.5 Hz, 2H), 5.37 (s, 2H), 5.20 (td, J=6.7, 11.2 Hz, 1H), 4.78 (dd, J=6.4, 9.4 Hz, 1H), 4.32 (dd, J=9.7, 10.9 Hz, 1H), 3.93 (s, 3H); LCMS m/z=413.1 [M+1]$^+$.

Example 32: WX032

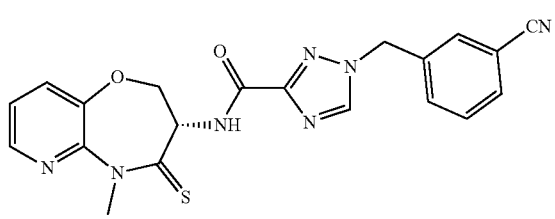 [SMILES: CN1C(=S)[C@@H](NC(=O)c2ncn(Cc3cccc(C#N)c3)n2)COc2cccnc21]

Route for Synthesis

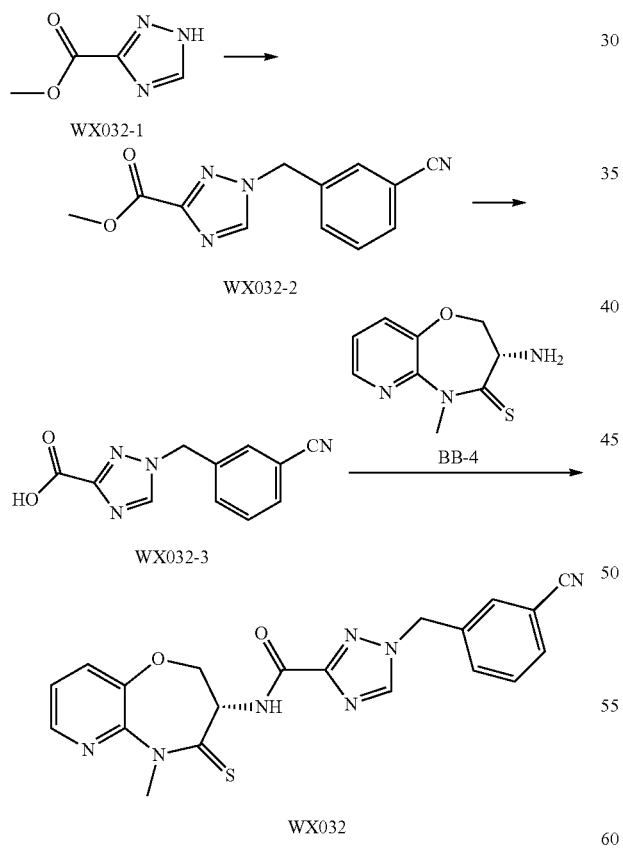

Step 1: Synthesis of Compound WX032-2

To MeCN (20 mL) were added WX032-1 (1.5 g, 11.80 mmol, 1 eq), 3-chloromethyl benzonitrile (1.97 g, 12.98 mmol, 1.72 mL, 1.1 eq) and K$_2$CO$_3$ (2.45 g, 17.70 mmol, 1.5 eq), and the reaction solution was continuously stirred at 50° C. for 12 hours. Water (50 mL) was added to the reaction solution and the mixture was extracted with ethyl acetate (50 mL×2). The organic phases were combined, washed with saturated brine (20 mL×2), and concentrated under reduced pressure to give a crude product. The crude product was purified by silica gel column chromatography (petroleum ether:ethyl acetate=100:1~1:100) to give compound WX032-2. $^1$H NMR (400 MHz, CDCl$_3$) δ=8.21 (s, 1H), 7.67 (t, J=4.3 Hz, 1H), 7.58 (s, 1H), 7.52 (d, J=4.8 Hz, 2H), 5.47 (s, 2H), 4.01 (s, 3H).

Step 2: Synthesis of Compound WX032-3

To a round bottom flask were added THF (8 mL) and H$_2$O (2 mL). WX032-2 (1.4 g, 5.78 mmol, 1 eq) and LiOH.H$_2$O (727.53 mg, 17.34 mmol, 3 eq) were then added, and the reaction solution was continuously stirred at 25° C. for 2 hours. The reaction solution was concentrated under reduced pressure to remove THF, 1 M diluted hydrochloric acid solution was added dropwise to the reaction solution to adjust pH to less than 3, and the mixture was filtered to give the target compound WX032-3. $^1$H NMR (400 MHz, DMSO-d$_6$) δ=8.83-8.80 (m, 1H), 7.86-7.80 (m, 2H), 7.68-7.57 (m, 2H), 5.59-5.52 (m, 2H).

Step 3: Synthesis of Compound WX032

To a round bottom flask was added N,N-dimethylformamide (1 mL). WX032-3 (15.50 mg, 67.94 µmol, 1 eq). BB-4 (30 mg, 67.94 µmol, 1 eq), DIPEA (26.34 mg, 203.82 µmol, 35.50 µL, 3 eq) and T$_3$P (64.85 mg, 101.91 µmol, 60.61 µL, 50% purity, 1.5 eq) were then slowly added, and the mixture was continuously stirred at 25° C. for 2 hours. The reaction solution was directly separated by HPLC (Column: Xtimate C18 100*30 mm*3 µm; Mobile phase: [water (0.225% FA)-ACN]; acetonitrile %: 35%-65%, 8 min) to give compound WX032. $^1$H NMR (400 MHz, CDCl$_3$) δ=8.85 (br d, J=7.3 Hz, 1H), 8.37 (d, J=3.3 Hz, 1H), 8.17 (s, 1H), 7.65 (br d, J=2.8 Hz, 1H), 7.60-7.55 (m, 2H), 7.53-7.47 (m, 2H), 7.29 (dd, J=4.6, 7.9 Hz, 1H), 5.45 (s, 2H), 5.26-5.15 (m, 1H), 4.79 (dd, J=6.3, 9.5 Hz, 1H), 4.38-4.28 (m, 1H), 3.93 (s, 3H); LCMS m/z=420.1 [M+1]$^+$.

Example 33: WX033

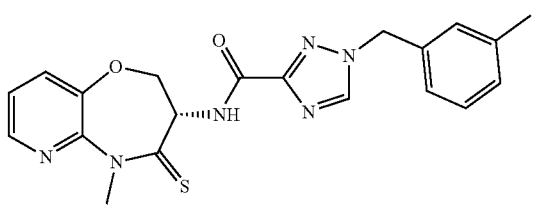 [SMILES: Cc1cccc(Cn2cnc(C(=O)N[C@H]3COc4cccnc4N(C)C3=S)n2)c1]

Route for Synthesis

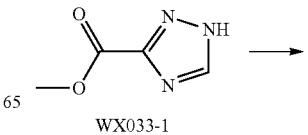

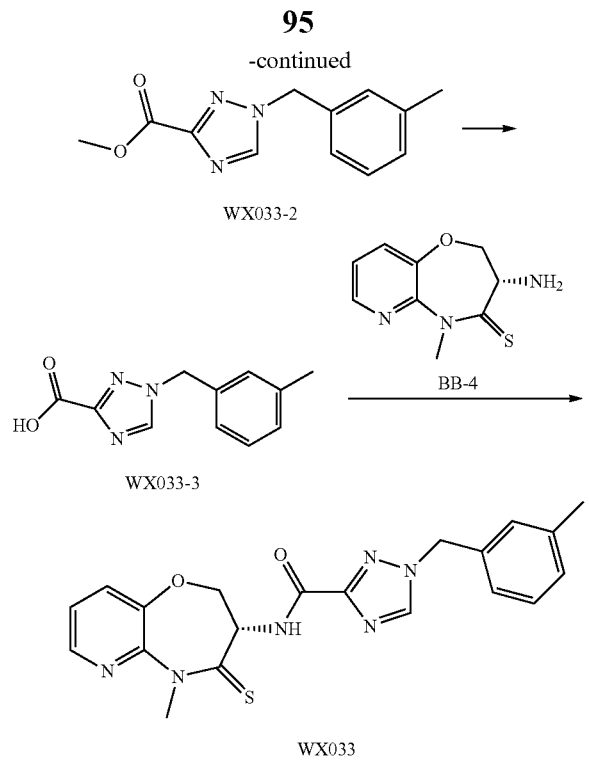

WX033-2

WX033-3

WX033

Step 1: Synthesis of Compound WX033-2

To a round bottom flask was added MeCN (20 mL). WX033-1 (1.5 g, 11.80 mmol, 1 eq), 3-methylbenzyl chloride (1.83 g, 12.98 mmol, 1.72 mL, 1.1 eq) and $K_2CO_3$ (2.45 g, 17.70 mmol, 1.5 eq) were added, and the mixture was continuously stirred at 50° C. for 12 hours. Water (50 mL) was added to the reaction solution and the mixture was extracted with ethyl acetate (50 mL×2). The organic phases were combined, washed with saturated brine (10 mL×2), and concentrated under reduced pressure to give a crude product. The crude product was purified by silica gel column chromatography (petroleum ether:ethyl acetate=100:1~1:100) to give compound WX033-2. $^1$H NMR (400 MHz, CDCl$_3$) δ=8.08 (s, 1H), 7.33-7.27 (n, 1H), 7.18 (d, J=7.6 Hz, 1H), 7.10 (br d, J=1.8 Hz, 2H), 5.38 (s, 2H), 4.05-3.97 (m, 3H), 2.38-2.31 (m, 3H).

Step 2: Synthesis of Compound WX033-3

To a round bottom flask were added THF (8 mL) and $H_2O$ (2 mL). WX033-2 (1.6 g, 6.92 mmol, 1 eq) and LiOH.H$_2$O (870.95 mg, 20.76 mmol, 3 eq) were then added, and the mixture was continuously stirred at 25° C. for 2 hours. The reaction solution was concentrated under reduced pressure to remove THF, 1 M diluted hydrochloric acid solution was added dropwise to the reaction solution to adjust pH to less than 3, and the mixture was filtered to give compound WX033-3. $^1$H NMR (400 MHz, DMSO-d$_6$) δ=13.28 (br s, 11H), 8.79 (s, 11H), 7.30-7.23 (m, 1H), 7.17-7.07 (m, 3H), 5.43 (s, 2H), 2.29 (s, 3H).

Step 3: Synthesis of Compound WX033

To a round bottom flask was added N,N-dimethylformamide (1 mL). WX033-3 (17.71 mg, 81.53 μmol, 1.2 eq), BB-4 (30 mg, 67.94 μmol, 1 eq), DIPEA (26.34 mg, 203.82 μmol, 35.50 μL, 3 eq) and T$_3$P (64.85 mg, 101.91 μmol, 60.61 μL, 50% purity, 1.5 eq) were then slowly added, and the mixture was continuously stirred at 25° C. for 2 hours. The reaction solution was directly separated by HPLC (Column: Xtimate C18 100*30 mm*3 μm; Mobile phase: [water (0.225% FA)-ACN]; acetonitrile %: 37%-67%, 8 mm) to give compound WX033. $^1$H NMR (400 MHz, CDCl$_3$) δ=8.81 (br d, J=7.0 Hz, 1H), 8.37 (d, J=3.3 Hz, 1H), 8.03 (s, 1H), 7.57 (d, J=6.8 Hz, 1H), 7.31-7.27 (m, 2H), 7.20-7.15 (m, 1H), 7.11-7.07 (m, 2H), 5.36 (s, 2H), 5.22 (td, J=6.8, 11.5 Hz, 1H), 4.79 (dd, J=6.4, 9.4 Hz, 1H), 4.36-4.27 (m, 1H), 3.93 (s, 3H), 2.34 (s, 3H); LCMS m/z=409.1 [M+1]$^+$.

Example 34: WX034

WX034

Route for Synthesis

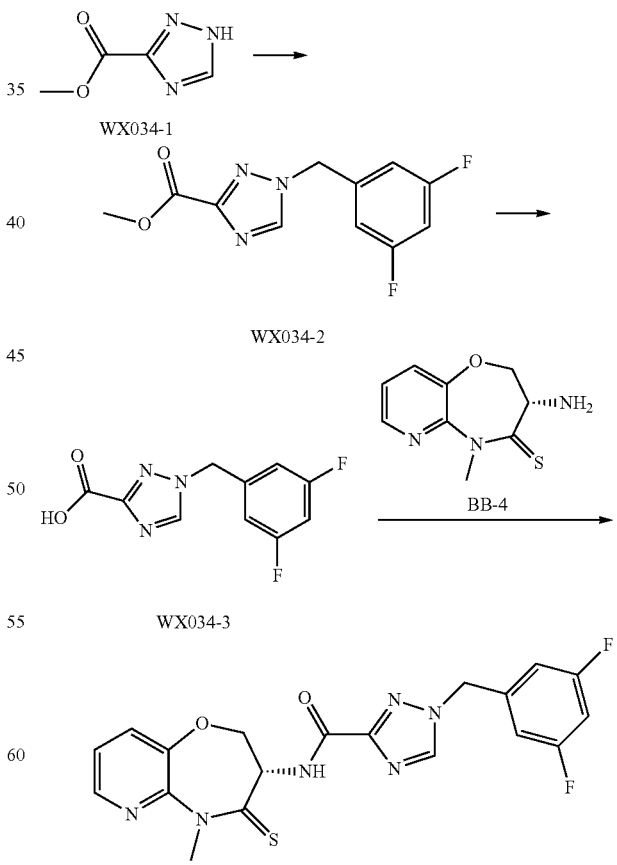

WX034-1

WX034-2

WX034-3

WX034

Step 1: Synthesis of Compound WX034-2

To a single-neck bottle was added MeCN (20 mL). 1-Chloromethyl-3,5-difluorobenzene (2.11 g, 12.98 mmol, 573.45 µL, 1.1 eq). WX034-1 (1.5 g, 11.80 mmol, 1 eq) and K$_2$CO$_3$ (2.45 g, 17.70 mmol, 1.5 eq) were then added, and the mixture was continuously stirred at 50° C. for 12 hours. A new spot appeared by TLC (petroleum ether:ethyl acetate=1:2) monitoring. Water (50 mL) was added to the reaction solution and the mixture was extracted with ethyl acetate (50 mL×2). The organic phase were combined, washed with saturated brine (20 mL×2), and concentrated under reduced pressure to give a crude product. The crude product was purified by silica gel column chromatography (petroleum ether:ethyl acetate=100:1~1:100) to give compound WX034-2. $^1$H NMR (400 MHz, CDCl$_3$) δ=8.22 (s, 1H), 6.92-6.77 (m, 3H), 5.50-5.38 (m, 2H), 4.11-3.99 (m, 3H).

Step 2: Synthesis of Compound WX034-3

To a round bottom flask were added THF (8 mL) and H$_2$O (2 mL). WX034-2 (1 g, 3.95 mmol, 1 eq) and LiOH.H$_2$O (497.15 mg, 11.85 mmol, 3 eq) were then added, and the mixture was continuously stirred at 25° C. for 2 hours. The reaction solution was concentrated under reduced pressure to remove THF, 1 M diluted hydrochloric acid solution was added dropwise to the remaining solution to adjust pH to less than 3, and the mixture was filtered to give compound WX034-3. $^1$H NMR (400 MHz, DMSO-d$_6$) δ=8.80 (s, 1H), 7.24 (br t, J=9.4 Hz, 1H), 7.07 (br d, J=6.3 Hz, 2H), 5.52 (s, 2H).

Step 3: Synthesis of Compound WX034

To a round bottom flask was added N,N-dimethylformamide (1 mL). WX034-3 (19.50 mg, 81.53 µmol, 1.2 eq), BB-4 (30 mg, 67.94 µmol, 1 eq), DIPEA (26.34 mg, 203.82 µmol, 35.50 µL, 3 eq) and T$_3$P (64.85 mg, 101.91 µmol, 60.61 µL, 50% purity, 1.5 eq) were then slowly added, and the mixture was continuously stirred at 25° C. for 2 hours. The reaction solution was directly separated by HPLC (Column: Xtimate C18 100*30 mm*3 µm; Mobile phase: [water (0.225% FA)-ACN]; acetonitrile %: 37%-67%, 8 min) to give compound WX034. $^1$H NMR (400 MHz, CDCl$_3$) δ=8.85 (br d, J=7.0 Hz, 1H), 8.37 (dd, J=1.5,4.6 Hz, 1H), 8.16 (s, 1H), 7.57 (dd, J=1.5, 8.0 Hz, 11H), 7.29 (dd, J=4.7, 7.9 Hz, 1H), 6.85-6.73 (m, 3H), 5.38 (s, 2H), 5.21 (td, J=6.6, 11.2 Hz, 1H), 4.79 (dd, J=6.4, 9.5 Hz, 1H), 4.33 (dd, J=9.6, 11.0 Hz, 1H), 3.93 (s, 3H); LCMS m/z=431.1 [M+1]$^+$.

Example 35: WX035

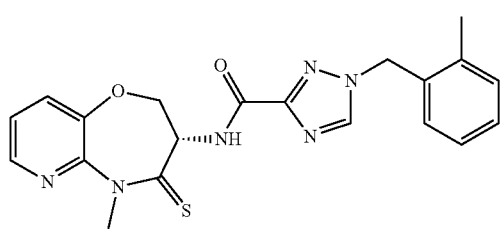 [SMILES: Cc1ccccc1Cn1cnc(C(=O)N[C@H]2COc3cccnc3N(C)C2=S)n1]

Route for Synthesis

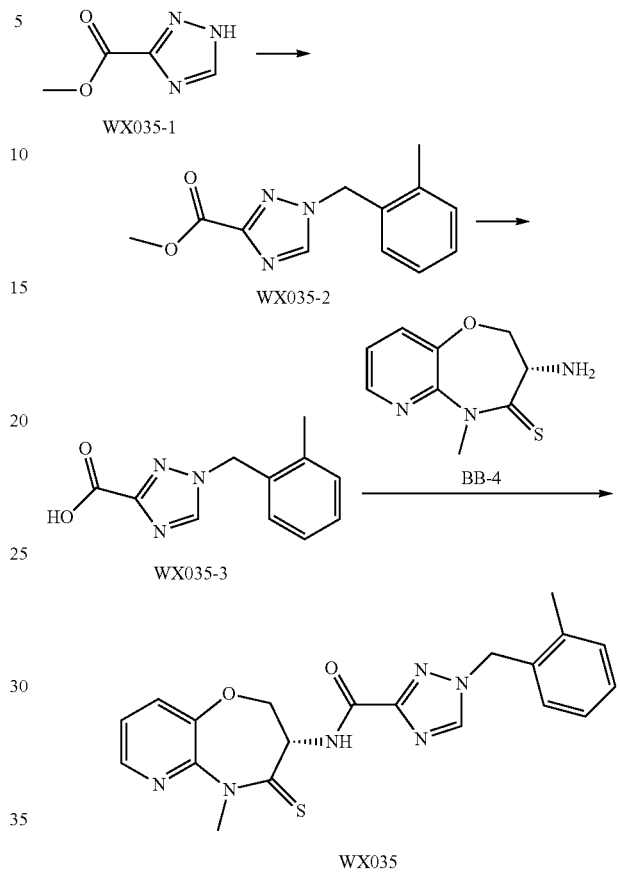

Step 1: Synthesis of Compound WX03-2

To MeCN (20 mL) were added WX035-1 (1.5 g, 11.80 mmol, 1 eq), 1-chloromethyl-2-toluene (1.83 g, 12.98 mmol, 1.72 mL, 1.1 eq) and K$_2$CO$_3$ (2.45 g, 17.70 mmol, 1.5 eq), and the mixture was continuously stirred at 50° C. for 12 hours. Water (50 mL) was added to the reaction solution and the mixture was extracted with ethyl acetate (50 mL×2). The organic phases were combined, washed with saturated brine (20 mL×2), and concentrated under reduced pressure to give a crude product. The crude product was purified by silica gel column chromatography (petroleum ether:ethyl acetate=100:1~1:100) to give compound WX03-2. $^1$H NMR (400 MHz, CDCl$_3$) δ=7.89 (s, 1H), 7.36-7.29 (m, 1H), 7.26-7.16 (m, 3H), 5.42 (s, 2H), 4.00 (s, 3H), 2.27 (s, 3H).

Step 2: Synthesis of Compound WX03&3

To a round bottom flask were added THF (8 mL) and H$_2$O (2 mL). WX035-2 (1.6 g, 6.92 mmol, 1 eq) and LiOH.H$_2$O (870.95 mg, 20.76 mmol, 3 eq) were then added, and the mixture was continuously stirred at 25° C. for 2 hours. The reaction solution was concentrated under reduced pressure to remove THF, 1 M diluted hydrochloric acid solution was added dropwise to the remaining solution to adjust pH to less than 3, and the mixture was filtered to give WX03-3. $^1$H NMR (400 MHz, DMSO-d$_6$)=13.28 (br s, 1H), 8.79 (s, 1H), 7.30-7.23 (m, 1H), 7.17-7.07 (m, 3H), 5.43 (s, 2H), 2.29 (s, 3H).

Step 3: Synthesis of Compound WX035

To a round bottom flask was added N,N-dimethylformamide (1 mL). WX035-3 (17.71 mg, 81.53 μmol, 1.2 eq), BB-4 (30 mg, 67.94 μmol, 1 eq), DIPEA (26.34 mg, 203.82 μmol, 35.50 μL, 3 eq) and T$_3$P (64.85 mg, 101.91 μmol, 60.61 μL, 50% purity 1.5 eq) were then slowly added, and the mixture was continuously stirred at 25° C. for 2 hours. The reaction solution was directly separated by HPLC (Column: Xtimate C18 100*30 mm*3 μm; Mobile phase: [water (0.225% FA)-ACN]; acetonitrile %: 37%-67%, 8 min) to give compound WX035. $^1$H NMR (400 MHz, CDCl$_3$) δ=8.81 (br d, J=7.0 Hz, 1H) 8.37 (d, J=4.5 Hz, 1H), 7.86 (s, 1H), 7.57 (d, J=7.8 Hz, 1H), 7.34-7.27 (m, 2H), 7.26-7.15 (m, 3H), 5.40 (s, 2H), 5.22 (td, J=6.7, 11.2 Hz, 1H), 4.79 (dd, J=6.4, 9.4 Hz, 1H), 4.38-4.26 (m, 1H), 3.93 (s, 3H), 2.29 (s, 3H); LCMS m/z=409.1 [M+1]$^+$.

Example 36: WX036

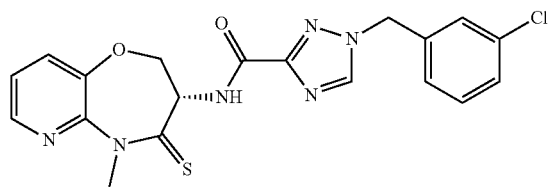 [SMILES: CN1C(=S)[C@@H](NC(=O)c2ncn(Cc3cccc(Cl)c3)n2)COc2cccnc21]

Route for Synthesis

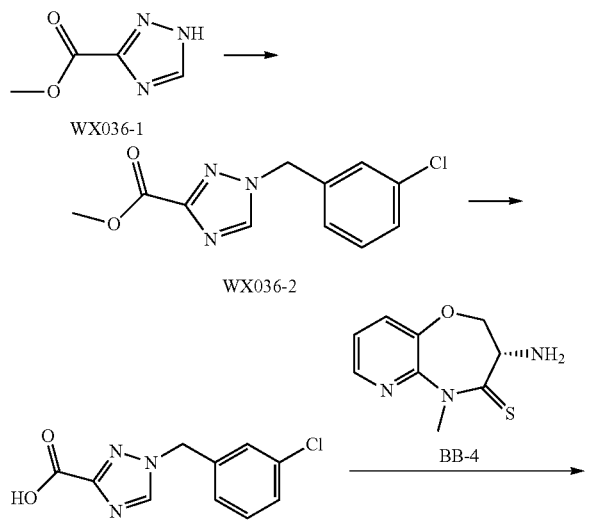

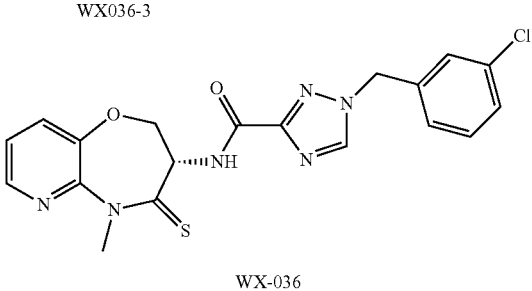

WX-036

Step 1: Synthesis of Compound WX036-2

To a round bottom flask was added MeCN (20 mL) at 25° C. WX036-1 (2.02 g, 15.89 mmol, 1 eq), K$_2$CO$_3$ (4.39 g, 31.79 mmol, 2 eq) and 1-chloro-3-chloromethylbenzene (3.07 g, 19.07 mmol, 2.42 mL, 1.2 eq) were then slowly added. The reaction solution was continuously stirred at 60° C. under nitrogen for 12 hours. The reaction solution was slowly poured into water (100 mL), nd the mixture was extracted with ethyl acetate (100 mL×2). The organic phases were combined, washed successively with water (100 mL) and saturated brine (100 mL), and concentrated under reduced pressure to give a crude product. The crude product was purified by silica gel column chromatography (petroleum ether:ethyl acetate=100:20~100:75) to give compound WX036-2. $^1$H NMR (400 MHz, CDCl$_3$) δ=8.15 (s, 1H), 7.35-7.26 (m, 3H), 7.17 (d, J=6.8 Hz, 1H), 5.40 (s, 2H), 4.04-3.93 (m, 3H).

Step 2: Synthesis of Compound WX036-3

To a round bottom flask were added THF (14 mL) and H$_2$O (2 mL) at 25° C. WX036-2 (1.80 g, 7.15 mmol, 1 eq) and LiOH.H$_2$O (900.33 mg, 21.46 mmol, 3 eq) were then slowly added. The reaction solution was continuously stirred at 25° C. under nitrogen for 1 hour. The reaction solution was adjusted to a pH of 6-7 with diluted hydrochloric acid (1 M), and the precipitate was filtered to give compound WX036-3.

Step 3: Synthesis of Compound WX036

To a round bottom flask was added N,N-dimethylacetamide (5 mL) at 25° C. BB-4 (20 ng, 45.29 μmol, 1 eq), T$_3$P (43.23 ng, 67.94 μmol, 40.41 μL, 50% purity, 1.5 eq), WX036-3 (16.14 mg, 67.94 μmol, 1.5 eq) and DIPEA (17.56 mg, 135.87 μmol, 23.67 μL, 3 eq) were then slowly added, and the reaction solution was continuously stirred at 25° C. under nitrogen for 2 hours. The reaction solution was slowly poured into water (100 mL), and the mixture was extracted with ethyl acetate (100 mL×2). The organic phases were combined, washed successively with water (100 mL) and saturated brine (100 mL), and concentrated under reduced pressure to give a crude product. The crude product was separated by preparative HPLC (Column: Xtimate C18 100*30 mm*3 μm; Mobile phase: [water (0.225% FA)-ACN]; acetonitrile %: 35%-65%, 8 min) to give compound WX036. $^1$H NMR (400 MHz, CDCl$_3$) δ=8.95-8.69 (m, 1H), 8.37 (br d, J=3.1 Hz, 1H), 8.10 (s, 1H), 7.68-7.47 (m, 1H), 7.38-7.27 (m, 3H), 7.26-7.20 (m, 1H), 7.16 (br d, J=7.0 Hz, 1H), 5.38 (s, 2H), 5.26-5.10 (m, 1H), 4.79 (dd, J=6.5, 9.4 Hz, 1H), 4.41-4.20 (m, 1H), 3.93 (s, 3H); LCMS m/z=429.0 [M+1]$^+$.

Example 37: WX037

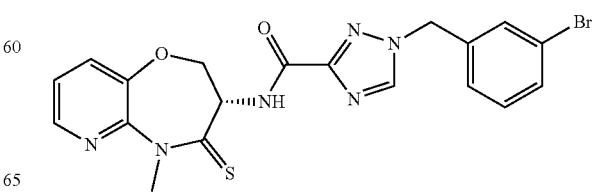

Route for Synthesis

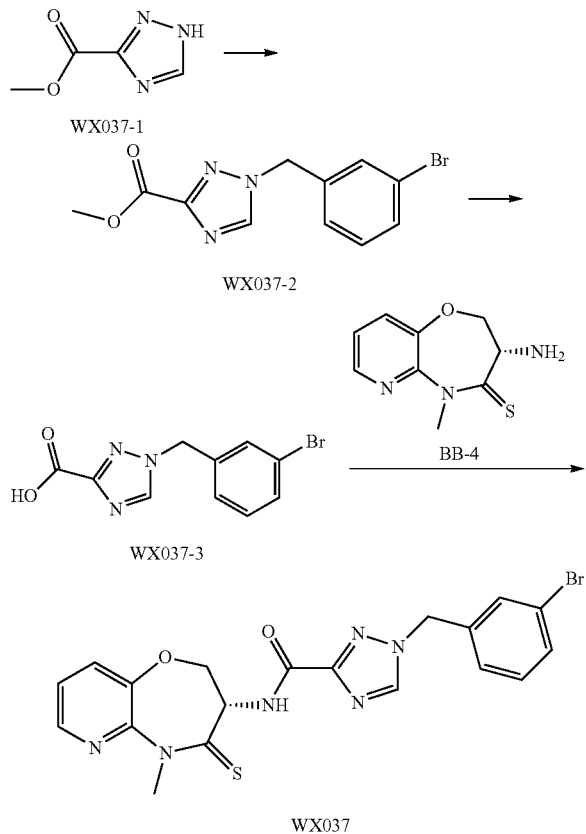

Step 1: Synthesis of Compound WX037-2

To a round bottom flask was added MeCN (20 mL) at 25° C. WX037-1 (2.03 g, 15.97 mmol, 1 eq), K$_2$CO$_3$ (4.41 g, 31.94 mmol, 2 eq) and 1-bromo-3-chloromethylbenzene (3.94 g, 19.17 mmol, 241.82 μL, 1.2 eq) were then slowly added. The reaction solution was continuously stirred at 60° C. under nitrogen for 12 hours. The reaction solution was slowly poured into water (100 mL), and the mixture was extracted with ethyl acetate (100 mL×2). The organic phases were combined, washed successively with water (100 mL) and saturated brine (100 mL), and concentrated under reduced pressure to give a crude product. The crude product was purified by silica gel column chromatography (petroleum ether:ethyl acetate=100:20~100:75) to give compound WX037-2. $^1$H NMR (400 MHz, CDCl$_3$) δ=8.14 (s, 1H), 7.59-7.38 (m, 2H), 7.30-7.26 (m, 1H), 7.25-7.20 (m, 1H), 5.39 (s, 2H), 4.01 (s, 3H).

Step 2: Synthesis of Compound WX037-3

To a round bottom flask were added THF (14 mL) and H$_2$O (2 mL) at 25° C. WX037-2 (2.0 g, 6.75 mmol, 1 eq) wad LiOH.H$_2$O (850.20 mg, 20.26 mmol, 3 eq) were then slowly added. The reaction solution was continuously stirred at 25° C. under nitrogen for 1 hour. The reaction solution was adjusted to a pH of 6-7 with diluted hydrochloric acid (1 M), and the precipitate was filtered to give compound WX037-3.

Step 3: Synthesis of Compound WX037

To a round bottom flask was added N,N-dimethylacetamide (5 mL) at 25° C. BB-4 (20 ng, 45.29 μmol, 1 eq), T$_3$P (43.23 ng, 67.94 μmol, 40.41 μL, 50% purity, 1.5 eq), WX037-3 (19.16 mg, 67.94 μmol, 1.5 eq) and DIPEA (17.56 mg, 135.87 μmol, 23.67 μL, 3 eq) were then slowly added, and the reaction solution was continuously stirred at 25° C. under nitrogen for 2 hours. The reaction solution was slowly poured into water (100 mL), and the mixture was extracted with ethyl acetate (100 mL×2). The organic phases were combined, washed successively with water (100 mL) and saturated brine (100 mL), and concentrated under reduced pressure to give a crude product. The crude product was separated by preparative HPLC (Column: Xtimate C18 100*30 mm*3 μm; Mobile phase: [water (0.225% FA)-ACN]; acetonitrile %: 35%-65%, 8 min) to give compound WX037. $^1$H NMR (400 MHz, CDCl$_3$) δ=8.83 (br d, J=6.4 Hz, 1H), 8.37 (br d, J=4.5 Hz, 1H), 8.10 (s, 1H), 7.66-7.27 (n, 4H), 7.25-7.15 (m, 2H), 5.37 (s, 2H), 5.26-5.06 (m, 1H), 4.79 (br dd, J=6.5, 9.1 Hz, 1H), 4.33 (br t, J=10.3 Hz, 1H), 3.93 (s, 3H); LCMS m/z=474.8 [M+1]$^+$.

Example 38: WX038

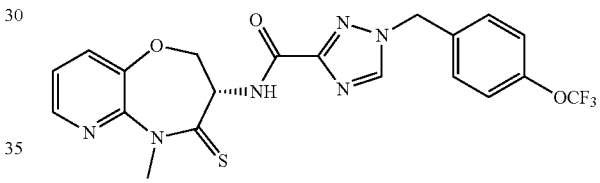

Route for Synthesis

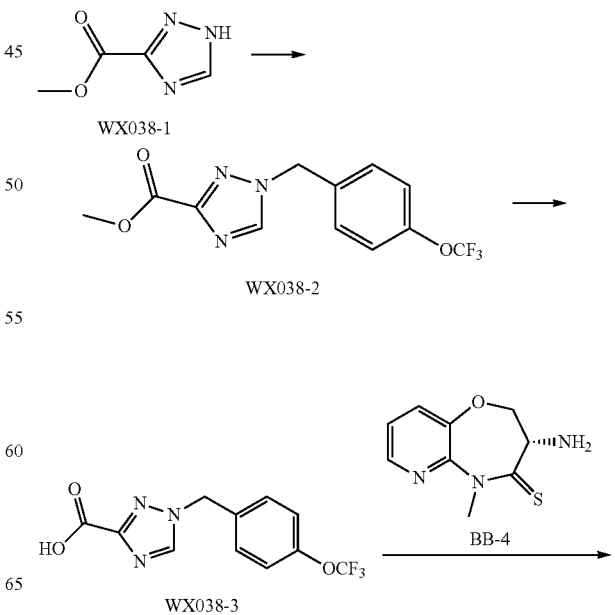

-continued

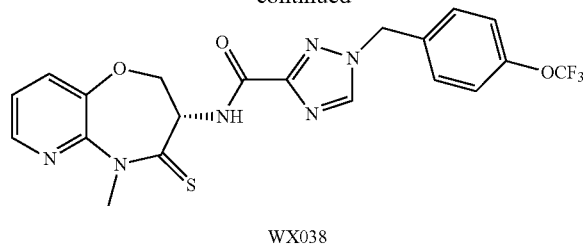

WX038

Step 1: Synthesis of Compound WX038-2

To a round bottom flask was added MeCN (20 mL). 1-Chloromethyl-4-trifluoromethoxybenzene (2.73 g, 12.98 mmol, 517.03 μL, 1.1 eq). WX038-1 (1.5 g, 11.80 mmol, 1 eq) and $K_2CO_3$ (2.45 g, 17.70 mmol, 1.5 eq) were then added, and the mixture was continuously stirred at 50° C. for 12 hours. Water (50 mL) %% added to the reaction solution and the mixture was extracted with ethyl acetate (50 mL×2). The organic phases were combined, washed with saturated brine (20 mL×2), and concentrated under reduced pressure to give a crude product. The crude product was purified by silica gel column chromatography (petroleum ether:ethyl acetate=100:1~1:100) to give compound WX038-2. $^1$H NMR (400 MHz, CDCl$_3$) δ=8.17 (s, 1H), 7.36 (d, J=8.5 Hz, 2H), 7.27-7.23 (m, 2H), 5.50-5.40 (m, 2H), 4.08-3.96 (m, 3H).

Step 2: Synthesis of Compound WX033-3

To a round bottom flask were added THF (16 mL) and H$_2$O (4 mL). WX038-2 (1.9 g, 6.31 mmol, 1 eq) and LiOH.H$_2$O (794.01 mg, 18.92 mmol, 3 eq) were then added, and the mixture was continuously stirred at 25° C. for 2 hours. The reaction solution was concentrated under reduced pressure to remove THF, 1 M diluted hydrochloric acid solution was added dropwise to the remaining solution to adjust pH to less than 3, and the precipitate was filtered to give compound WX038-3. $^1$H NMR (400 MHz, DMSO-d$_6$) δ=8.81 (s, 1H), 7.51-7.33 (m, 4H), 5.53 (s, 2H).

Step 3: Synthesis of Compound WX038

To a round bottom flask was added N,N-dimethylformamide (1 mL). WX038-3 (23.41 mg, 81.53 μmol, 1.2 eq), BB-4 (30 mg, 67.94 μmol, 1 eq), DIPEA (26.34 mg, 203.82 μmol, 35.50 μL, 3 eq) and T$_3$P (64.85 mg, 101.91 μmol, 60.61 μL, 50% purity, 1.5 eq) were then slowly added, and the mixture was continuously stirred at 25° C. for 2 hours. The reaction solution was directly separated by HPLC (Column: Xtimate C18 1003 mm*3 μm; Mobile phase: [water (0.225% FA)-ACN]; acetonitrile %: 40%-70%, 8 min) to give compound WX038. $^1$H NMR (400 MHz, CDCl$_3$) δ=8.84 (br d, J=7.3 Hz, 1H), 8.38 (dd, J=1.5, 4.5 Hz, 1H), 8.11 (s, 1H), 7.58 (dd, J=1.5, 8.0 Hz, 1H), 7.34 (d, J=8.8 Hz, 2H), 7.32-7.29 (m, 1H), 7.27 (s, 5H), 7.26-7.22 (m, 2H), 5.42 (s, 2H), 5.28-5.15 (m, 1H), 4.80 (dd, J=6.5, 9.5 Hz, 1H), 4.37-4.29 (m, 1H), 3.94 (s, 3H); LCMS m/z=479.1 [M+1]$^+$.

Example 39: WX039

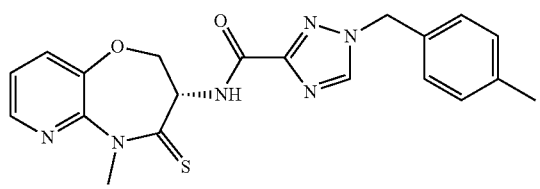 [SMILES: Cc1ccc(Cn2cnc(C(=O)N[C@H]3COc4cccnc4N(C)C3=S)n2)cc1]

Route for Synthesis

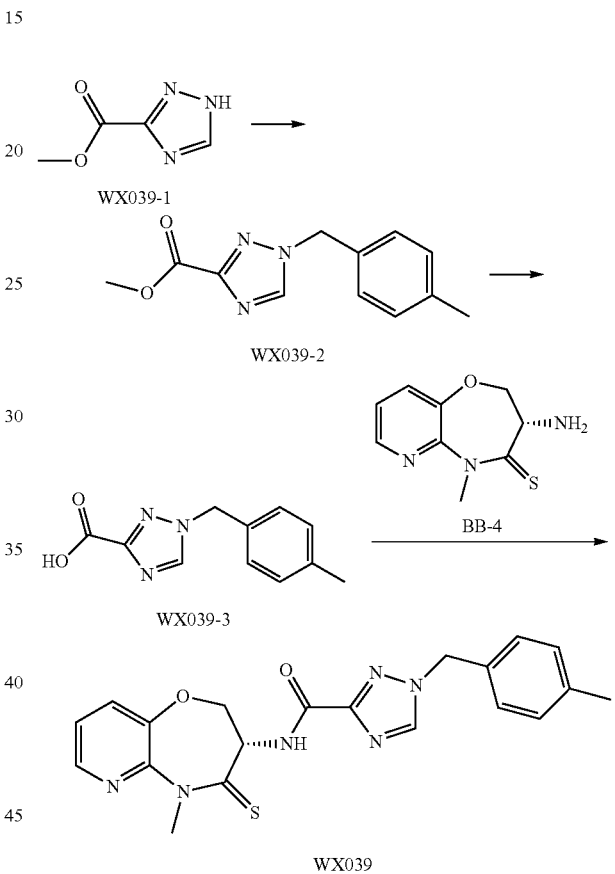

Step 1: Synthesis of Compound WX039-2

To a round bottom flask was added MeCN (20 mL) at 25° C. WX039-1 (2.0 g, 15.74 mmol, 1 eq), K$_3$CO$_3$ (4.35 g, 31.48 mmol, 2 eq) and 1-chloromethyl-4-methylbenzene (2.66 g, 18.89 mmol, 2.48 mL, 1.2 eq) were then slowly added. The reaction solution was continuously stirred at 60° C. under nitrogen for 12 hours. The reaction solution was slowly poured into water (100 mL), and the mixture was extracted with ethyl acetate (100 mL×2). The organic phases were combined, washed successively with water (100 mL) and saturated brine (100 mL), and concentrated under reduced pressure to give a crude product. The crude product was purified by silica gel column chromatography (petroleum ether:ethyl acetate=100:20~100:75) to give compound WX039-2. $^1$H NMR (400 MHz, CDCl$_3$) δ=8.04 (s, 1H), 7.23-7.17 (m, 4H), 5.37 (s, 2H), 4.00 (s, 3H), 2.47-2.25 (m, 3H).

Step 2: Synthesis of Compound WX039-3

To a round bottom flask were added THF (14 mL) and H₂O (2 mL) at 25° C. WX039-2 (1.5 g, 6.49 mmol, 1 eq) and LiOH·H₂O (816.52 mg, 19.46 mmol, 3 eq) were then slowly added. The reaction solution was continuously stirred at 25° C. under nitrogen for 1 hour. The reaction solution was adjusted to a pH of 6-7 with diluted hydrochloric acid (1 M), and the precipitate was collected by filtration to give compound WX039-3.

Step 3: Synthesis of Compound WX039

To N,N-dimethylacetamide (5 mL) were added BB-4 (20 ng, 45.29 µmol, 1 eq), T₃P (43.23 mg, 67.94 µmol, 40.41 µL, 50% purity, 1.5 eq), WX039-3 (14.76 mg, 67.94 µmol, 1.5 eq) and DIPEA (17.56 mg, 135.87 µmol, 23.67 µL, 3 eq) at 25° C., and the reaction solution was continuously stirred at 25° C. under nitrogen for 2 hours. The reaction solution was slowly poured into water (100 mL), and the mixture was extracted with ethyl acetate (100 mL×2). The organic phases were combined, washed successively with water (100 mL) and saturated brine (100 mL), and concentrated under reduced pressure to give a crude product. The crude product was separated by preparative HPLC (Column: Xtimate C18 100*30 mm*3 µm; Mobile phase: [water (0.225% FA)-ACN]; acetonitrile %: 40%-70%, 8 min) to give a product WX039. ¹H NMR (400 MHz, CDCl₃) δ=8.80 (br d, J=7.3 Hz, 1H), 8.37 (dd, J=1.5, 4.5 Hz, 1H), 8.00 (s, 1H), 7.36 (dd, J=1.5, 7.8 Hz, 1H), 7.28 (dd, J=4.8, 8.0 Hz, 1H), 7.19 (s, 4H), 5.35 (s, 2H), 5.21 (td, J=6.8, 11.0 Hz, 1H), 4.78 (dd, J=6.4, 9.4 Hz, 1H), 4.32 (dd, J=9.7, 11.2 Hz, 1H), 3.93 (s, 3H), 2.63-2.13 (m, 3H); LCMS m/z=409.1 [M+1]⁺.

Example 40: WX040

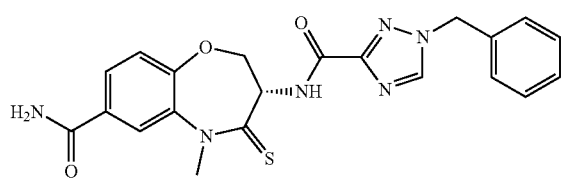 [SMILES: CN1C(=S)[C@@H](NC(=O)c2ncn(Cc3ccccc3)n2)COc2ccc(C(N)=O)cc21]

Route for Synthesis

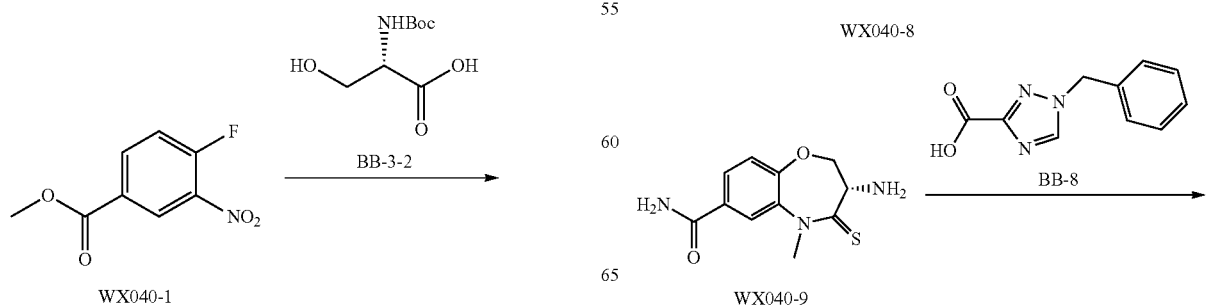

-continued

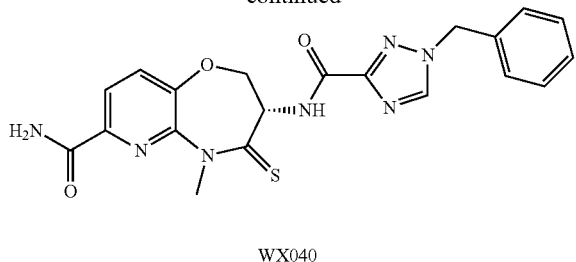

WX040

Step 1: Synthesis of Compound WX040-2

To a round bottom flask was added THF (100 mL). WX040-1 (10 g, 50.22 mmol, 1 eq), BB-3-2 (11.34 g, 55.24 mmol, 1.1 eq) and cesium carbonate (29.45 g, 90.39 mmol, 1.8 eq) were then slowly added, and the mixture was continuously stirred at 65° C. for 16 hours. TLC (petroleum ether:ethyl acetate:acetic acid-1:1:0.1) showed that the raw materials were completely consumed. The reaction solution was poured into water (300 mL), and 2 M diluted hydrochloric acid was then added dropwise to adjust pH to 3. The mixture was extracted with ethyl acetate (500 mL×2). The organic phases were combined and washed with saturated brine (50 mL×2). The organic phase was then concentrated under reduced pressure to give WX40-2. $^1$H NMR (400 MHz, CDCl$_3$) δ=8.46 (d, J=1.8 Hz, 1H), 8.20 (dd, J=2.0, 8.8 Hz, 1H), 7.12 (d, J=8.8 Hz, 1H), 5.62 (br d, J=8.0 Hz, 1H), 4.83-4.61 (m, 2H), 4.45 (dd, J=3.0, 9.3 Hz, 1H), 3.93 (s, 3H), 1.45 (s, 10H).

Step 2: Synthesis of Compound WX040-3

To a hydrogenation bottle was added MeOH (300 mL). WX040-2 (25.8 g, 67.13 mmol, 1 eq) and Pd/C (2.6 g, 26.02 mmol, 10% purity) were then slowly added. The atmosphere was replaced three times with argon gas, and the mixture was continuously stirred at 30° C. under H$_2$ (40 Psi) atmosphere for 24 hours. A new spot appeared by TLC (petroleum ether:ethyl acetate:acetic acid=1:1:0.1) monitoring. The reaction solution was filtered through Celite, and the filtrate was concentrated under reduced pressure to give compound WX040-3. $^1$H NMR (400 MHz, CDCl$_3$) δ=7.50-7.44 (m, 1H), 7.39 (br s, 1H), 6.70 (d, J=8.5 Hz, 1H), 6.53 (br s, 2H), 6.00 (br d, J=7.5 Hz, 1H), 4.73 (br d, J=7.0 Hz, 1H), 4.43 (br d, J=8.5 Hz, 1H), 4.31-4.24 (m, 1H), 3.85 (s, 3H), 1.41 (s, 9H).

Step 3: Synthesis of Compound WX040-4

To a round bottom flask was added ethyl acetate (200 mL). WX040-3 (12.5 g, 35.28 mmol, 1 eq), T$_3$P (33.67 g, 52.91 mmol, 31.47 mL, 50% purity, 1.5 eq) and DIPEA (13.68 g, 105.83 mmol, 18.43 mL, 3 eq) were then slowly added, and the mixture was continuously stirred at 25° C. for 2 hours. Water (200 mL) was added to the reaction solution and the layers were separated. The aqueous phase %% extracted with ethyl acetate (200 mL×2). The organic phases were combined, and washed with saturated brine (100 mL×2), and then the organic phase was concentrated under reduced pressure to give a crude product. The crude product was purified by silica gel column chromatography (petroleum ether-ethyl acetate=100:1~1:1) to give compound WX0404. $^1$H NMR (400 MHz, CDCl$_3$) δ=8.15 (br s, 1H), 7.80 (dd, J=2.0, 8.5 Hz, 1H), 7.73 (d, J=2.0 Hz, 1H), 7.13 (d, J=8.3 Hz, 1H), 5.62 (br d, J=5.3 Hz, 1H), 4.71-4.59 (m, 2H), 4.33-4.23 (m, 1H), 3.95-3.89 (m, 3H), 1.43 (s, 9H).

Step 4: Synthesis of Compound WX040.5

To a round bottom flask was added N,N-dimethylformamide (200 mL). WX040-4 (17 g, 50.54 mmol, 1 eq), cesium carbonate (49.40 g, 151.63 mmol, 3 eq) and iodomethane (21.52 g, 151.63 mmol, 9.44 mL, 3 eq) were then slowly added, aid the mixture %% M continuously stirred at 25° C. for 2 hours. Water (300 mL) was added to the reaction solution, and the mixture was extracted with ethyl acetate (300 mL×2). The organic phases were combined, and washed with saturated brine (100 mL×2), and the organic phase was then concentrated under reduced pressure to give a crude product. The crude product was purified by silica gel column chromatography (petroleum ether-ethyl acetate=100:1~1:1) to give compound WX040-5. $^1$H NMR (400 MHz, CDCl$_3$) δ=7.92-7.83 (m, 2H), 7.18 (d, J=8.4 Hz, 1H), 5.50 (br d, J=6.1 Hz, 1H), 4.72-4.52 (m, 2H), 4.28-4.17 (m, 1H), 3.92 (s, 3H), 3.42 (s, 3H), 1.38 (s, 9H).

Step 5: Synthesis of Compound WK040-6

To toluene (40 mL) were slowly added WX040-5 (4.01 g, 11.45 mmol, 1 eq), Lawsson's reagent (5.09 g, 12.59 mmol, 1.1 eq) and Boc$_2$O (10.60 g, 48.55 mmol, 11.15 mL, 4.24 eq), and the mixture was heated to 110° C. and continuously stirred for 12 hours. The reaction solution was slowly poured into saturated brine (30 mL), and the mixture was extracted with ethyl acetate (100 mL×2). The organic phases were combined, and washed with saturated brine (30 mL×2), and the organic phase was then concentrated under reduced pressure to give a crude product. The crude product was purified by silica gel column chromatography (petroleum ether:ethyl acetate=100:1~1:1) to give compound WX0406. $^1$H NMR (400 MHz, CDCl$_3$) δ=7.99-7.92 (m, 2H), 7.21 (d, J=8.3 Hz, 1H), 6.02 (br d, J=7.8 Hz, 1H), 4.80-4.69 (m, 1H), 4.53 (dd, J=6.3, 9.5 Hz, 1H), 4.22 (dd, J=9.5, 11.3 Hz, 1H), 3.94 (s, 3H), 3.86 (s, 3H), 1.46-1.33 (m, 9H).

Step 6: Synthesis of Compound WX040-7

To a round bottom flask were added THF (8 mL) and H$_2$O (2 mL). WX040-6 (800 mg, 2.18 mmol, 1 eq) and LiOH.H$_2$O (183.23 mg, 4.37 mmol, 2 eq) were then slowly added, mad the mixture was continuously stirred at 25° C. for 2 hours. Diluted hydrochloric acid solution was added dropwise to the reaction solution to adjust pH to <3, and the precipitate was filtered and collected to give compound WX040-7. $^1$H NMR (400 MHz, CDCl$_3$) δ=7.89-7.79 (m, 1H), 7.25-7.20 (m, 1H), 7.02-6.95 (m, 1H), 6.17-6.02 (m, 1H), 4.88-4.74 (m, 1H), 4.56 (dd, J=6.4, 9.7 Hz, 1H), 4.31-4.17 (m, 1H), 3.85 (s, 3H), 1.41 (s, 9H).

Step 7: Synthesis of Compound WX04

To a round bottom flask was added N,N-dimethylformamide (5 mL). WX040-7 (200 mg, 567.53 μmol, 1 eq), NH$_4$Cl (91.07 mg, 1.70 mmol, 3 eq), HATU (647.37 mg, 1.70 mmol, 253.15 μL, 3.00 eq) and DIPEA (366.75 mg, 2.84 mmol, 494.27 μL, 5 eq) were then slowly added, and the mixture was continuously stirred at 25° C. for 2 hours. The reaction solution was directly separated by HPLC (Column: Xtimate C18 100*30 mm*3 μm; Mobile phase: [water (0.225% FA)-ACN]; acetonitrile %: 30%-60%, 8 min) to give compound WX040-8. $^1$H NMR (400 MHz, CDCl$_3$)

δ=7.82 (s, 1H), 7.64 (br d, J=8.3 Hz, 1H), 7.22 (d, J=8.3 Hz, 1H), 6.98 (s, 2H), 5.01 (br s, 1H), 4.86-4.66 (m, 1H), 4.52 (dd, J=6.3, 9.5 Hz, 1H), 4.30-4.11 (m, 1H), 3.86 (s, 3H), 1.40 (s, 9H).

Step 8: Synthesis of Compound WX040-9

To a round bottom flask was added ethyl acetate (10 mL). WX040-0 (40 mg, 113.82 μmol, 1 eq) and HC/ethyl acetate (4 M, 10.00 mL, 351.42 eq) were then slowly added, and the mixture was continuously stirred at 25° C. for 1 hour. The reaction solution was concentrated wider reduced pressure to give compound WX040-9. $^1$H NMR (400 MHz, DMSO-$d_6$) δ=8.16-8.04 (m, 2H), 7.91 (d, J=8.5 Hz, 1H), 7.57 (s, 1H), 7.37 (d, J=8.3 Hz, 1H), 4.62-4.41 (m, 3H), 3.82 (s, 3H).

Step 9: Synthesis of Compound WX040

To DMSO (1 mL) were slowly added WX040-9 (30 mg, 119.38 μmol, 1 eq, HCl). BB-6 (24.26 mg, 119.38 μmol, 1 eq), HATU (68.09 mg, 179.07 μmol, 1.5 eq) and DIEA (46.28 mg, 358.13 μmol, 62.38 μL, 3 eq), and the mixture was continuously stirred at 25° C. for 2 hours. The reaction solution was directly separated by HPLC (Column: Phenomenex Gemini-NX 80*30 mm*3 μm; Mobile phase: [water (10 mM NH$_4$HCO$_3$)-ACN]; acetonitrile %: 28%-58%, 9 min) to give compound WX040. $^1$H NMR (400 MHz, CDCl$_3$) δ=8.70 (br d, J=7.3 Hz, 1H), 8.04 (s, 1H), 7.69 (s, 1H), 7.39-7.36 (m, 1H), 7.31-7.28 (m, 7H), 5.39 (s, 2H), 5.20 (td, J=6.8, 11.0 Hz, 1H), 4.72 (dd, J=6.5, 9.4 Hz, 1H), 4.31 (t, J=10.3 Hz, 1H), 3.89 (s, 3H); LCMS m/z=437.1 [M+1]$^+$.

Example 41: WX041

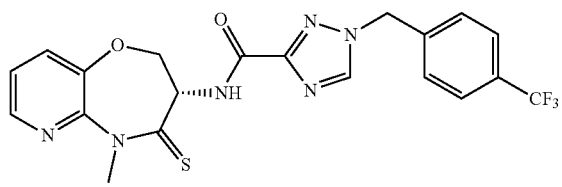 [SMILES: CN1C(=S)[C@@H](NC(=O)c2ncn(Cc3ccc(C(F)(F)F)cc3)n2)COc2cccnc21]

Route for Synthesis

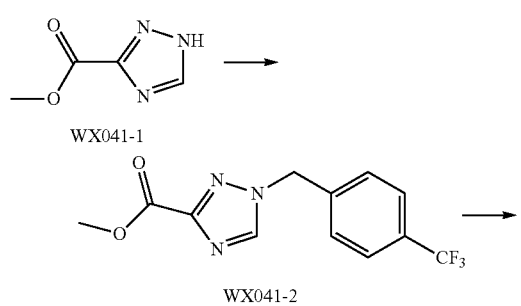

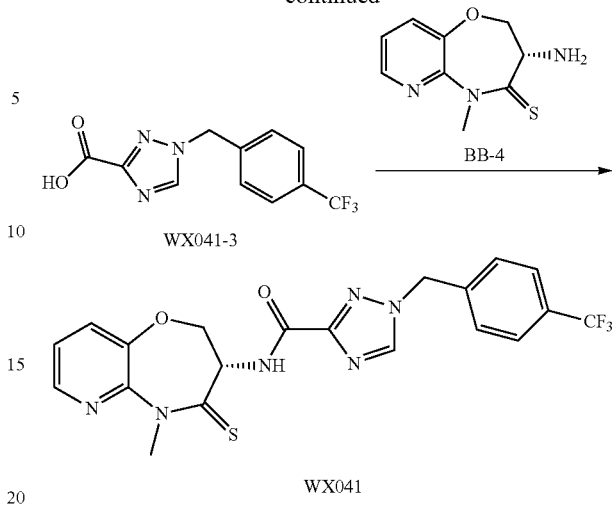

Step 1: Synthesis of Compound WX041-2

To a round bottom flak was added MeCN (20 mL) at 25° C. WX041-1 (2.68 g, 21.09 mmol, 1 eq), K$_2$CO$_3$ (5.83 g, 42.17 mmol, 2 eq) and 4-(chloromethyl)trifluoromethylbenzene (4.92 g, 25.30 mmol, 3.73 mL, 1.2 eq) were then slowly added. The reaction solution was continuously stirred at 60° C. under nitrogen for 12 hours. The reaction solution was slowly poured into water (100 mL), and the mixture was extracted with ethyl acetate (100 mL×2). The organic phases were combined, and washed successively with water (100 mL) and saturated brine (100 mL), and the organic phase was then concentrated under reduced pressure to give a crude product. The crude product was purified by silica gel column chromatography (petroleum ether:ethyl acetate=100:20-100:75) to give compound WX041-2. $^1$H NMR (400 MHz, CDCl$_3$) δ=8.17 (s, 1H), 7.65 (d, J=8.0 Hz, 2H), 7.40 (d, J=8.0 Hz, 2H), 5.49 (s, 2H), 4.08-3.91 (m, 3H).

Step 2: Synthesis of Compound WX041-3

To a round bottom flask were added THF (20 mL) and H$_2$O (4 mL) at 25° C. WX041-2 (2.40 g, 8.41 mmol, 1 eq) and LiOH.H$_2$O (1.06 g, 25.24 mmol, 3 eq) were slowly added. The reaction solution was continuously stirred at 25° C. under nitrogen for 1 hour. The reaction solution was adjusted to a pH of 6-7 with diluted hydrochloric acid (1 M), and the precipitate was filtered and collected to give compound WX041-3.

Step 3: Synthesis of Compound WK041

To a round bottom flask was added N,N-dimethylacetamide (5 mL) at 25° C. BB-4 (20 ng, 45.29 μmol, 1 eq), T$_3$P (43.23 mg, 67.94 μmol, 40.41 μL, 50% purity, 1.5 eq), WX041-3 (18.42 mg, 67.94 μmol, 1.5 eq) and DIPEA (17.56 mg, 135.87 μmol, 23.67 μL, 3 eq) were slowly added, and the reaction solution was continuously stirred at 25° C. under nitrogen for 2 hours. The reaction solution was slowly poured into water (100 mL), and the mixture was extracted with ethyl acetate (100 mL×2). The organic phases were combined, and washed successively with water (100 mL) aid saturated brine (100 mL), and then the organic phase was concentrated under reduced pressure to give a crude product. The crude product was separated by preparative HPLC (Column: Phenomenex Gemini-NX 80*30 mm*3 μm; Mobile phase: [water (10 mM NH$_4$HCO)-ACN] to give compound WX041. $^1$H NMR (400 MHz, CDCl$_3$) δ=8.77 (br d, J=7.5 Hz, 1H), 8.31 (br d, J=3.6 Hz, 1H), 8.07 (s, 1H), 7.65-7.45 (m, 3H), 7.33 (br d, J=8.0 Hz, 2H), 7.22 (dd, J=4.8, 7.9 Hz, 11H), 5.40 (s, 2H), 5.23-4.97 (m, 1H), 4.72 (dd, J=6.5, 9.4 Hz, 1H), 4.25 (t, J=10.3 Hz, 1H), 3.87 (s, 3H); 19F NMR (377 MHz, CDCl$_3$) δ=−43.60 (s, 1F); LCMS m/z=463.1 [M+1]$^+$.

Example 42: WX042

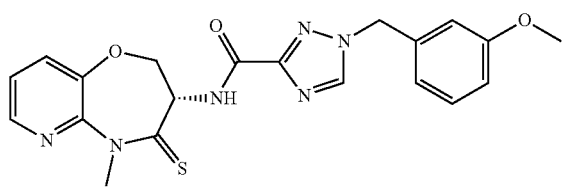 [SMILES: COc1cccc(Cn2cnc(C(=O)N[C@H]3COc4cccnc4N(C)C3=S)n2)c1]

Route for Synthesis

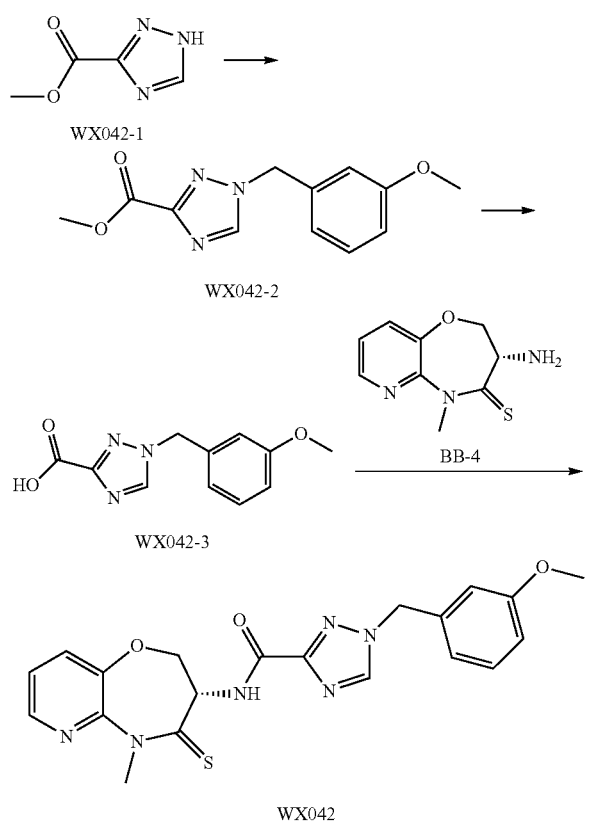

Step 1: Synthesis of Compound WX042-2

To MeCN (20 mL) were added WX042-1 (2 g, 15.74 mmol, 1 eq), 3-chloromethyl anisole (2.46 g, 15.74 mmol, 2.14 mL, 1 eq), and K$_2$CO$_3$ (2.61 g, 18.88 mmol, 1.2 eq), and the mixture was reacted at 50° C. for 12 hours. The reaction solution was filtered to remove K$_2$CO$_3$. The filter cake was washed with ethyl acetate (15 mL×3), and the filtrate was washed with saturated brine (50 mL). The organic phase was concentrated under reduced pressure to give a crude product. The crude product was purified by silica gel column chromatography (petroleum ether:ethyl acetate=100:1-100:100) to give compound WX042-2. $^1$H NMR (400 MHz, CDCl$_3$) δ=8.10-81.01 (m, 1H), 7.30-7.21 (m, 1H), 6.91~6.80 (m, 2H), 6.77 (s, 1H), 5.34 (s, 21), 3.96 (s, 3H), 3.75 (s, 3H).

Step 2: Synthesis of Compound WX042-3

To THF (30 mL) was added WX042-2 (2.5 g, 10.11 mmol, 1 eq). A solution of LiOH.H$_2$O (509.17 mg, 12.13 mmol, 1.2 eq) in H$_2$O (3 mL) was then added. The reaction was stirred at 25° C. for 3 hours. TLC (petroleum ether-ethyl acetate=1:1) showed that the raw materials were completely consumed. The reaction solution was adjusted to a pH of 6 with 1 M dilute hydrochloric acid, and the mixture was concentrated under reduced pressure to remove the solvent. Toluene (10 mL) were added to the remaining solution and the mixture was concentrated under reduced pressure again to remove toluene to give compound WX042-3. $^1$H NMR (400 MHz, CDCl$_3$) δ=7.19 (s, 4H), 7.21-7.17 (m, 1H), 4.65 (s, 2), 3.79 (s, 3H); LCMS m/z=233.9 [M+1]$^+$.

Step 3: Synthesis of Compound WX042

To N,N-dimethylformamide (5 mL) were added BB-4 (94.67 mg, 214.39 μmol, 1 eq), WX042-3 (50 mg, 214.39 μmol, 1 eq), T$_3$P (163.71 mg, 257.26 μmol, 153.00 μL, 50% purity, 1.2 eq), and DIPEA (41.56 mg, 321.58 μmol, 56.01 μL, 1.5 eq), and the mixture was reacted at 25° C. for 2 hours. LCMS showed that the raw materials were completely consumed. The reaction solution was concentrated under reduced pressure to about 5 mL. The residue was purified by HPLC (formic acid system) to give compound WX042. $^1$H NMR (400 MHz, CDCl$_3$) δ=8.81 (br d, J=7.0 Hz, 1H), 8.37 (dd, J=1.6, 4.6 Hz, 1H), 8.04 (s, 1H), 7.57 (dd, J=1.6, 7.9 Hz, 1H), 7.33-7.27 (m, 2H), 7.00-6.69 (m, 3H), 5.36 (s, 2H), 5.22 (td, J=6.7, 11.1 Hz, 1H), 4.79 (dd, J=6.3, 9.5 Hz, 1H), 4.32 (dd, J=9.5, 11.0 Hz, 1H), 3.93 (s, 3H), 3.79 (s, 3H).

Assay Example 1: In Vitro Assaying Part

Assay Steps
1.1 Reagents

| Reagent | Brand | Batch No. |
|---|---|---|
| RPMI-1640 | GIBCO | 11875-119 |
| 10X DPBS | GIBCO | 14200-075 |
| Fetal Bovine Serum (FBS) | Biowest | S1810-500 |
| Pen/Strep (100X) | Biowest | L0022-100 |
| CellTiter Glo | Promega | G7571 |
| Q-VD-OPh Hydrate | Sigma | SML0063-5MG |
| Recombinant human TNF-a | Pepotech | 300-01A-50 |

1.2 Instrument and Materials
CULTURPLATE-384+LID/50W Brand PerkinElmer cat #6007680
Envision plate reader (Perkin Elmer, Cat #2104-0010)
1.3 Formulation of Reagents
(1) 1×DPSB: To 100 mL of 10×DPBS was added 900 mL of deionized water.
(2) 1640 complete medium: To 89 mL of RPMI-1640 medium were added 10 mL of FBS and 1 mL of penicillin/streptomycin

2. Assay Steps

1. U937 cells were centrifuged, and then the medium was discarded. The cells were resuspended in 1640 complete medium and counted. The cell concentration was adjusted to $5\times10^5$ cells/mL for use, and the cells were arranged according to compounds to be assayed.
2. To the prepared resuspension of U937 cells were added QVD-OPh at a final concentration of 25 μM and TNF-α at a final concentration of 100 ng/mL, and then the mixture was mixed gently.
3. To a 384-well plate was added 30 μL/well of U937 cells containing 25 μM of QVD-OPh and TNF-α at a final concentration of 100 ng/mL, and blank control wells without QVD-OPh and TNF-α were set up.
4. To the dosing group %% added 10 μL of the assay compound at 4 times the preset concentration, and to the blank control well was added DMSO at the corresponding concentration.
5. The 384-well plate was placed in a 37° C. and 5% $CO_2$ cell incubator for 24 hours.
6. After 24 hours, the 384-well plate was taken out and equilibrated at room temperature for 20 minutes.
7. 40 μL of CTG was added to each well, and then the plate was shaken on a shaker in the dark for 2 minutes.
8. The plate was incubated at room temperature in the dark for 10 minutes, and then read using an Envision plate reader.

Results of Assay:

The results of assay of compounds of the present disclosure were shown in Table 1.

TABLE 1

| U937 cell activity assay results of the compounds of the present disclosure ||
| --- | --- |
| Compound No. | $IC_{50}$ of cell assay (nM) |
| WX001 | 0.5 |
| WX002 | 1.8 |
| WX003 | 0.5 |
| WX004 | 0.3 |
| WX005 | 2 |
| WX006 | 9 |
| WX007 | 70 |
| WX008 | 8.1 |
| WX009 | 1.4 |
| WX010 | 47 |
| WX011 | 1.7 |
| WX012 | 12.1 |
| WX013 | 1.8 |
| WX014 | 3.7 |
| WX015 | 5.1 |
| WX016 | 9.8 |
| WX017 | 59 |
| WX018 | 1.3 |
| WX019 | 0.6 |
| WX020 | 0.6 |
| WX021 | 13 |
| WX022 | 20 |
| WX023 | 29 |
| WX024 | 43 |
| WX025 | 12 |
| WX026 | 5 |
| WX027 | 20 |
| WX028 | 4.7 |
| WX029 | 2.2 |
| WX030 | 15.6 |
| WX031 | 2.4 |
| WX032 | 5.7 |
| WX033 | 7.6 |
| WX034 | 3.7 |
| WX035 | 4.9 |
| WX036 | 6.4 |

TABLE 1-continued

| U937 cell activity assay results of the compounds of the present disclosure ||
| --- | --- |
| Compound No. | $IC_{50}$ of cell assay (nM) |
| WX037 | 24 |
| WX038 | 238 |
| WX039 | 3.4 |
| WX040 | 4.8 |
| WX041 | 86.5 |
| WX042 | 24.8 |

Conclusion of Assay:

It can be seen from the above table that the compounds of the present disclosure show a good inhibitory activity in the cell activity assay of inhibiting TNFα/QVD-OPh-induced programmed cell necrosis (Necroptosis).

Assay Example 2: In Vitro Activity Assay of Mouse RIP1

Cell Line

L929 (purchased from ATCC, Item No.: CCL-1)

Reagent

| Reagent name | Brand | Item No. |
| --- | --- | --- |
| EMEM medium | ATCC | 30-2003 |
| Horse serum | Gibco | 16050130 |
| Double antibiotics (penicillin, streptomycin) | Millipore | TMS-AB2-C |
| Recombinant murine tumor necrosis factor alpha (TNF-α) | R&D | 410-MT-010 |
| Caspase inhibitor (QVD-OPh) | R&D | OPH001-01M |
| CellTiter Glo fluorescent cells | Promega | G7573 |

Instrument

Microplate reader (Perkin Elmer, Envision)

Formulation of Reagents

L929 cell complete medium: EMEM+10% horse serum (volume ratio)+1% double antibiotics (volume ratio)

Assay Step

1. The cultured L929 cells were digested with trypsin, centrifuged, resuspended in complete culture medium, and then counted. The cell concentration was then diluted to $1\times10^5$/mL with complete culture medium.
2. The cell suspension was added to a 96-well plate at 100 μL per well and incubated at 37° C. and 5% $CO_2$ for 24 h.
3. Different concentrations of assay compounds were added to each well, and dimethyl sulfoxide was added to the control group. The plate was incubated at 37° C. and 5% $CO_2$ for 1 h.
4. To each well were added TNF-α at a final concentration of 50 ng/mL and Q-VD at a final concentration of 50 μM, and the plate was incubated at 37° C. and 5% $CO_2$ for 24 h.

5. To each well was added 50 μL of CellTiter Glo fluorescent cells, and the plate was shaken in the dark for 10 min.
6. The plate was read on the microplate reader.

Results of Assay

The results of assay of compounds of the present disclosure were shown in Table 2.

TABLE 2

L929 cell activity assay results of the compounds of the present disclosure

| Compound No. | $IC_{50}$ of cell assay (nM) |
|---|---|
| WX001 | 1161 |
| WX003 | 1213 |
| WX005 | 1311 |
| WX008 | 47 |
| WX009 | 103 |
| WX011 | 11 |
| WX013 | 14 |
| WX019 | 51 |
| WX020 | 29 |
| WX021 | 445 |
| WX028 | 65 |
| WX029 | 184 |
| WX031 | 174 |
| WX032 | 255 |
| WX039 | 64 |

Conclusion of Assay:

It can be seen from the above table that the compounds of the present disclosure show a good inhibitory activity in the mouse L929 cell activity assay of inhibiting TNFα/QVD-OPh-induced programmed cell necrosis (Necroptosis).

Assay Example 3: Pharmacokinetic of the Compound

Assay Steps

Eight healthy adult C57BL/6 mice (6-9 weeks old, purchased from Shanghai Lingchang Biotechnology Co., Ltd.) were selected, and randomly divided into two groups, 4 mice in each group (n=2, cross blood sampling). One group was given 0.5 mg/kg of the assay compound by intravenous injection, and the other group was given 1 mg/kg of the assay compound by gavage. Plasma samples were collected respectively from animals in the intravenous group and gavage group at 0.083, 0.25, 0.5, 1.0, 2.0, 4.0, 6.0, 8.0, 24 hours after administration. The blood concentration was determined by LC-MS/MS method. Relevant pharmacokinetic parameters were calculated by WinNonlin™ Version 6.3 (Pharsight, Mountain View, CA) pharmacokinetic software using non-compartmental model and linear logarithmic trapezoidal method. $AUC_{0-last}$ represents the area under the plasma concentration-time curve from zero time point to the last detectable concentration time point; $C_{max}$ represents the peak concentration; $T_{max}$ represents the time to reach the peak; $T_{1/2}$ represents the half-life. CL represents the clearance rate; $T_{last}$ represents the last quantifiable time point; p.o. represents per os; i.v. represents intravenous injection; and F % represents oral bioavailability.

Results of Assay

The results of assay of compounds of the present disclosure were shown in Table 3.

TABLE 3

Pharmacokinetic properties of the compound

| | Compound | WX009 |
|---|---|---|
| i.v. | $T_{1/2}$ (h) | 1.4 |
| | $Vd_{ss}$ (L/kg) | 1.1 |
| | CL(mL/min/kg) | 9.4 |
| | $AUC_{0-last}$ (nM · h) | 2210 |
| p.o. | $T_{max}$ (h) | 0.5 |
| | $C_{max}$ (nM) | 1495 |
| | $AUC_{0-last}$ (nM · h) | 3854 |
| | F % | 89.1 |

Conclusion of Assay

The compound of the present disclosure has good pharmacokinetic properties, in vivo exposure, and bioavailability.

Assay Example 4: In Vivo Efficacy Study in Mouse Model of Tumor Necrosis Factor (TNF-α) Induced Systemic Inflammatory Response Syndrome (SIRS)

Reagent

| Reagent | Brand | Cat # or Lot |
|---|---|---|
| Tumor Necrosis Factor (TNF-α) | Pepro Tech | 315-01A-1MG |
| Caspase inhibitor zVAD | GL Biochem (Shanghai) Ltd. | GLS180522-01001 |

Instruments and Materials
1) Electronic balance: Brand Changzhou Tianzhiping Instrument Equipment Co., Ltd., Model JY20002
2) Anal thermometer. Brand PHYSITEMP, model BAT-12

Formulation of Reagents
1) TNF-α: TNF-α was centrifuged quickly (10000 rmp, 30 s) before opening the lid. One bottle of TNF-α (1 mg) was dissolved in 1 mL of sterile water to prepare a mother liquor with a concentration of 1 mg/mL. The mother liquor was stored at 4° C. and cm be stored for one week, 1000 μL of the mother liquor was weighed and added to 5667 μL of sterile water, and then 333 mg of trehalose was added and dissolved to prepare a working solution.
2) zVAD: 20 ng of zVAD was weighed and added to 480 μL of DMSO, and the mixture was vortexed, sonicated, and heated at 37° C., and then 15.52 mL of physiological saline was added. A working solution with a concentration of 1.25 mu/mL was prepared.

Assay Steps
1) The mice were reared adaptively for 3 days, and then randomly grouped into cages, 5 mice in each cage. Ear tags were cut.
2) Firstly, the mice were given the corresponding compound by gavage according to their body weight, and then injected intraperitoneally with zVAD at a dose of 250 μg per mouse. After the intraperitoneal injection of zVAD, the anal temperature was measured immediately (0 h), and the time was recorded. The time when mice were given zVAD was defined as the $0^{th}$ hour (0 h).
3) After 15 minutes, TNF-α was injected through the tail vein at a dose of 200 μL per mouse, and then the anal temperature was measured 15 minutes later (0.5 h).

4) After 1 h, zVAD was injected intraperitoneally at a dose of 125 μg per mouse, and then the anal temperature was measured immediately (1 h). The anal temperature was measured again at 2 h, 3 h, and 4 h.

Results of Assay

The results of assay of the compound of the present disclosure were shown in Table 4.

TABLE 4

Body temperature and survival rate of mice

| Groups | Number of animals in each group | Decrease in mouse body temperature (° C.) | | | | 4-hour survival rate of animals |
| --- | --- | --- | --- | --- | --- | --- |
| | | 1 hour | 2 hours | 3 hours | 4 hours | |
| TNF-α + zVAD + vehicle | 5 | 2.94 | 9.02 | — | — | 0% after 2 hours |
| TNF-α + zVAD + WX009(10 mpk) | 5 | 0.94 | 1.2 | 1.42 | 1.52 | 100% |

Conclusion of Assay

The compound of the present disclosure shows a very good protective effect in the mouse model of inhibiting systemic inflammatory response syndrome (SIRS) induced by TNF-α/zVAD, wherein the decrease in body temperature of mice was significantly reduced, and the survival rate of animals was increased from 0% to 100%.

Assay Example 5: In Vitro Caco-2 Cell Permeability Assay

Cell Culture

MEM (minimum essential medium) supplemented with 2 mM L-glutamine, 10% Fetal Bovine Serum (FBS), 100 U/mL penicillin-G and 100 μg/mL streptomycin was used for cell culture. The conditions for cell culture were 37±1° C., 5% $CO_2$ and saturated humidity. When cells were grown to 80-90% confluency, trypsin (0.05%, w/v)/EDTA (0.02% w/v) digestion solution was added to digest the cells for seeding. The cells were seeded in BD Falcon's Transwell-96-well plate at a seeding density of $1 \times 10^5$ cells/cm². The cells were cultured in a carbon dioxide incubator for 22 days and then used for transport assay.

Transport Assay Hank's balanced salt buffer containing 10 mM HEPES (pH 7.40±0.05) was used in this assay as transport buffer. Two-way transport of the assay compound and the positive drug digoxin at a concentration of 2 μM was assayed, each in duplicate. Transport of fenoterol and propranolol from the apical end to the basal end (A-B) was assayed. The concentration of DMSO in the incubation system was controlled below 1% After the sample was added, the cell plate ws incubated at 37±1° C., 5% $CO_2$ and saturated humidity for 120 minutes. All sample were vortexed and then centrifuged at 3220 rpm and 20° C. for 20 minutes. The control and assay samples were diluted 1:1 (v:v) with ultrapure water, and then stored at 4° C. Liquid chromatography tandem mass spectrometry (LC/MS/MS) was used for analysis and testing.

Analysis of Samples

In this assay, liquid chromatography tandem mass spectrometry (LC/MS/MS) was used to semi-quantitatively analyze the peak area ratio of the assay compound and the control substances fenoterol, propranolol and digoxin to the internal standard in the starting solution, the receiving solution, and the supernatant of the dosing well.

Data Calculation

Apparent permeability coefficient ($P_{app}$, cm/s), efflux rate and recovery rate were calculated using the following formulae.

The apparent permeability coefficient ($P_{app}$, cm/s) was calculated using the following formula:

$$P_{app} = (dC_r/d_t) \times V_r / (A \times C_0)$$

wherein $dC_r/d_t$ is the cumulative concentration of the compound at the receiving end per unit time (μM/s); $V_r$ is the volume of solution at the receiving end (the volumes of solutions at the apical end and the basal end were 0.075 mL and 0.250 mL, respectively); A is the relative surface area of the cell monolayer (0.0804 cm²); $C_0$ is the peak area ratio of the initial concentration (nM) of the assay substance or the control substances at the dosing end.

The efflux rate was calculated using the following formula:

$$\text{Efflux rate} = P_{app}(BA) / P_{app}(AB)$$

The recovery rate was calculated using the following formula:

$$\% \text{ recovery rate} = 100 \times [(V_r \times C_r) + (V_d \times C_d)] / (V_d \times C_0)$$

wherein $C_0$ is the initial concentration (nM) of the assay substance at the dosing end or the peak area ratio of the control substances; $V_d$ is the volume at the dosing end (the apical end was 0.075 mL, and the basal end was 0.250 mL); $C_d$ and $C_r$ we peak area ratios of the final concentrations (nM) of the assay substance or the control substances at the dosing end and the receiving end, respectively.

Results of Assay

The results of assay of the compound of the present disclosure were shown in Table 5.

TABLE 5

Results of Caco-2 cell permeability assay

| Compound | Apparent permeability coefficient ($10^{-6}$ cm/s) | Efflux rate |
| --- | --- | --- |
| WX009 | 18.35 | 0.75 |

Conclusion of Assay

The compound of the present disclosure is a compound with high permeability and has low efflux rate.

Assay Example 6: Assay of Plasma Protein Binding Rate (PPB)

796 μL of bank plasma from humans, SD rats and CD-1 mice (plasma purchased from BioreclamationIVT) were weighed, and the assay compound working solution or warfarin working solution was added so that the final concentration of the assay compound and warfarin in the plasma sample was 2 μM. The samples were mixed thoroughly. The final concentration of DMSO in the organic phase was 0.5%, 50 μL of plasma samples of the assay compound and warfarin were pipetted to a sample receiving plate, and the corresponding volume of the corresponding blank plasma or buffer was added immediately, so that the final volume in each sample well was 100 μL, wherein the volume ratio of plasma:dialysis buffer was 1:1. Stop solution was then added to these samples. These samples were used as $T_0$ samples for determination of recovery and stability.

The plasma samples of the assay compound and warfarin were added to the dosing end of each dialysis well, and blank dialysis buffer was added to the corresponding receiving end of the dialysis well. The dialysis plate was then sealed with a breathable membrane, placed in a wet 5% $CO_2$ incubator, and incubated with shaking at 100 rpm at 37° C. for 4 hours. After the dialysis was over, 50 µL of dialyzed buffer sample and dialyzed plasma sample were pipetted to a new sample receiving plate. The corresponding volume of the corresponding blank plasma or buffer solution was added to the samples, so that the final volume in each sample well was 100 µL, wherein the volume ratio of plasma:dialysis buffer was 1:1. All samples were subjected to protein precipitation, and then analyzed by LC/MS/MS. Unbound rate (% Unbound), bound rate (% Bound), and recovery rate (% Recovery) of the compound were calculated using the following formulae:

% Unbound=100*$F_C/T_C$,

% Bond=100−% Unbound, and

% Recovery=100*$(F_C+T_C)/T_0$, wherein $F_C$ is the concentration of the compound at the buffer end of the dialysis plate; $T_C$ is the concentration of the compound at the plasma and of the dialysis plate; and $T_0$ is the concentration of the compound in the plasma sample at time zero.

Results of Assay
The results of assay of the compound of the present disclosure are shown in Table 6.

TABLE 6

Results of assay of plasma protein binding rate

| Compound | PPB_Unbound (%) |
|---|---|
| WX009 | 5.7 (human)/29.7 (rat)/7.0 (mouse) |

Conclusion of Assay
The compound of the present disclosure has a reasonable plasma protein binding rate in human, rat, and mouse, and the drug in abound state in human plasma is 5.7%.

Assay Example 7: Assay of Pharmacokinetic Parameters in Dogs

Assay Steps
Four healthy adult beagle dogs were selected and randomly divided into two groups. One group was given the assay compound by intravenous injection, and the other group was given the assay compound by gavage. Plasma samples were collected respectively from animals in the intravenous group and gavage group at 0.083, 0.25, 0.5, 1.0, 2.0, 4.0, 6.0, 8.0, 24 hours after administration. The blood concentration was determined by LC-MS/MS method. Relevant pharmacokinetic parameters were calculated by WinNonlin™ Version 6.3 (Pharsight. Mountain View, CA) pharmacokinetic software using non-compartmental model and linear logarithmic trapezoidal method. $AUC_{0-last}$ represents the area under the plasma concentration-time curve from zero time point to the last detectable concentration time point; $C_{max}$ represents the peak concentration; $T_{max}$ represents the time to reach the peak; $T_{1/2}$ represents the half-life; CL represents the clearance rate; $Vd_{ss}$ represents apparent volume of distribution; p.o. represents per os; i.v. represents intravenous injection; and F % represents oral bioavailability.

Results of Assay
The results of assay of the compounds of the present disclosure were shown in Table 7.

TABLE 7

Pharmacokinetic properties of the compounds of the present disclosure

| | Compounds | WX009 | WX013 |
|---|---|---|---|
| | | Dosing regimen | |
| | | iv = 3 mpk; po = 10 mpk | iv = 1 mpk; po = 5 mpk |
| iv | $T_{1/2}$ (h) | 5.5 | 4.89 |
| | $Vd_{ss}$ (L/kg) | 2.4 | 2.02 |
| | CL(mL/min/kg) | 6.2 | 5.18 |
| | $AUC_{0-last}$ (nM · h) | 20762 | 7417 |
| po | $T_{max}$ (h) | 2.0 | 2935 |
| | $C_{max}$ (nM) | 284 | 1.50 |
| | $AUC_{0-last}$ (nM · h) | 23640 | 27744 |
| | F % | 34.2% | 80.1% |

Conclusion of Assay
The compounds of the present disclosure have better pharmacokinetic properties and higher in vivo exposure in dogs. Especially, the half-life of the compounds of the present disclosure reaches about 5 hours which is relatively ideal.

Assay Example 8: Kinase Selectivity Assay of the Compound of the Present Disclosure The purpose of this assay was to detect the in vitro inhibitory activity of WX009 on a variety of kinases. The kinases used in this assay included 413 kinases, and the activity detection method was provided by Eurofins Pharma Discovery Service A method of detecting $^{33}P$ radiolabeled kinase activity was used for the assay. The concentration of WX009 was 1 µM, and the concentration of ATP was 10 µM. The assay results were shown in Table 8.

TABLE 8

Results of kinase profile assay of WX009

| Inhibition rate | Number of kinases | Name of kinases |
|---|---|---|
| >80% | 1 | RIP1 |
| 50-79% | 1 | LIMK2 |
| <50% | 411 | All other kinases |

Conclusion of assay: The compound of the present disclosure has highly specific kinase selectivity, and almost only has highly active inhibitory effect on RIP1. Therefore, the compound of the present disclosure has a lower risk of off-targeting to other kinase targets.

What is claimed is:
1. A compound represented by formula (I), or a stereoisomer or a pharmaceutically acceptable salt thereof,

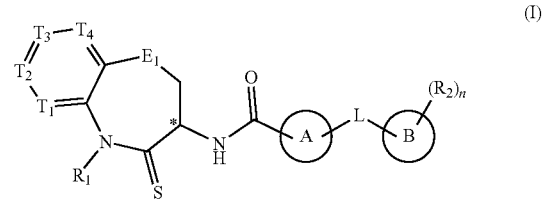

wherein
T₁ is selected from N and $CR_{1t}$;
T₂ is selected from N and $CR_{2t}$;
T₃ is selected from N and $CR_{3t}$;
T₄ is selected from N and $CR_{4t}$;
E₁ is selected from C $(R_{1e})_2$, O, C (=O), S, and $NR_{2e}$;
Ring A is selected from 1,2,4-triazolyl, 1,2,3-triazolyl, imidazolyl, isoxazolyl, 1,3,4-oxadiazolyl,

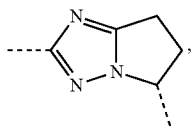

tetrazolyl, pyridyl, and

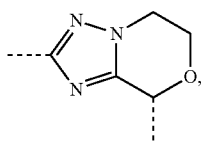

wherein the 1,2,4-triazolyl, 1,2,3-triazolyl, imidazolyl, isoxazolyl, 1,3,4-oxadiazolyl,

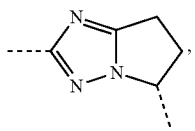

tetrazolyl, pyridyl, and

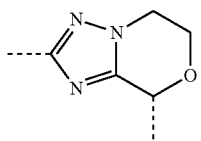

are optionally substituted with 1, 2 or 3 halogen or $C_{1-3}$ alkyl;
Ring B is selected from the group consisting of phenyl and

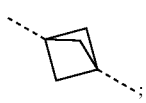

L is selected from the group consisting of single bond, O, C(=O), S, NH, and $C_{1-3}$ alkylene, wherein the C1-3 alkylene is optionally substituted with 1, 2 or 3 $R_a$;
R₁ is selected from the group consisting of H and $C_{1-3}$ alkyl, wherein the $C_{1-3}$ alkyl is optionally substituted with 1, 2 or 3 $R_b$;
$R_{1t}$, $R_{2t}$, $R_{3t}$, and $R_{4t}$ are each independently selected from the group consisting of H, F, Cl, Br, I, OH, CN, NH₂, $C_{1-3}$ alkyl, COOH, and -C(=O) NH₂, wherein the $C_{1-3}$ alkyl is optionally substituted with 1, 2 or 3 $R_c$;

$R_{1e}$ is each independently selected from the group consisting of H, F, Cl, Br, I, OH, CN, NH₂, and $C_{1-3}$ alkyl, wherein the $C_{1-3}$ alkyl is optionally substituted with 1, 2 or 3 $R_d$;
$R_{2e}$ is selected from the group consisting of H and $C_{1-3}$ alkyl, wherein the $C_{1-3}$ alkyl is optionally substituted with 1, 2 or 3 $R_e$;
R₂ is each independently selected from the group consisting of H, F, Cl, Br, I, OH, NH₂, CN, $C_{1-3}$ alkyl, and $C_{1-3}$ alkoxy, wherein the $C_{1-3}$ alkyl and $C_{1-3}$ alkoxy are optionally substituted with 1, 2 or 3 $R_f$;
n is 1, 2, 3, 4, or 5;
$R_a$, $R_b$, $R_c$, $R_d$, $R_e$, and $R_f$ are each independently selected from the group consisting of F, Cl, Br, I, OH, CN, NH2, and D; and
the carbon atom with "*" is a chiral carbon atom, which exists in the form of a single (R) or(S) enantiomer or a mixture enriched in one enantiomer.

2. The compound, or the stereoisomer or the pharmaceutically acceptable salt thereof according to claim 1, wherein R1 is selected from the group consisting of H and CH₃, wherein the CH₃ is optionally substituted with 1, 2 or 3 $R_b$.

3. The compound, or the stereoisomer or the pharmaceutically acceptable salt thereof according to claim 2, wherein R₁ is selected from the group consisting of H, CH₃, and CD₃.

4. The compound, or the stereoisomer or the pharmaceutically acceptable salt thereof according to claim 1, wherein $R_{1t}$, $R_{2t}$, $R_{3t}$, and $R_{4t}$ are each independently selected from the group consisting of H, F, Cl, Br, I, OH, CN, NH₂, CH₃, COOH, and -C(=O) NH₂, wherein the CH₃ is optionally substituted with 1, 2 or 3 $R_c$.

5. The compound, or the stereoisomer or the pharmaceutically acceptable salt thereof according to claim 4, wherein $R_{1t}$, $R_{2t}$, $R_{3t}$, and $R_{4t}$ are each independently selected from the group consisting of H, F, Cl, Br, I, OH, CN, NH₂, and CH₃.

6. The compound, or the stereoisomer or the pharmaceutically acceptable salt thereof according to claim 1, wherein $R_{1e}$ is each independently selected from the group consisting of H, F, Cl, Br, I, OH, CN, NH₂, and CH₃.

7. The compound, or the stereoisomer or the pharmaceutically acceptable salt thereof according to claim 1, wherein $R_{2e}$ is selected from the group consisting of H and CH₃.

8. The compound, or the stereoisomer or the pharmaceutically acceptable salt thereof according to claim 1, wherein E₁ is selected from the group consisting of CH₂, O, C(=O), S, and NH.

9. The compound, or the stereoisomer or the pharmaceutically acceptable salt thereof according to claim 1, wherein R₂ is each independently selected from the group consisting of H, F, Cl, Br, I, OH, NH₂, CN, CH₃, and OCH₃, wherein the CH₃ and OCH₃ are optionally substituted with 1, 2 or 3 $R_f$.

10. The compound, or the stereoisomer or the pharmaceutically acceptable salt thereof according to claim 9, wherein R₂ is each independently selected from the group consisting of H, F, Cl, Br, I, OH, NH₂, CN, CH₃, OCH₃, CF₃, and OCF₃.

11. The compound, or the stereoisomer or the pharmaceutically acceptable salt thereof according to claim 1, wherein Ring A is selected from the group consisting of

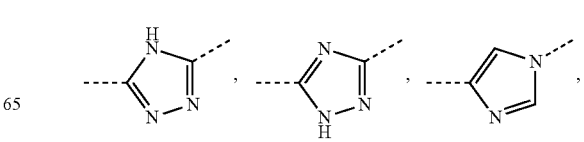

-continued

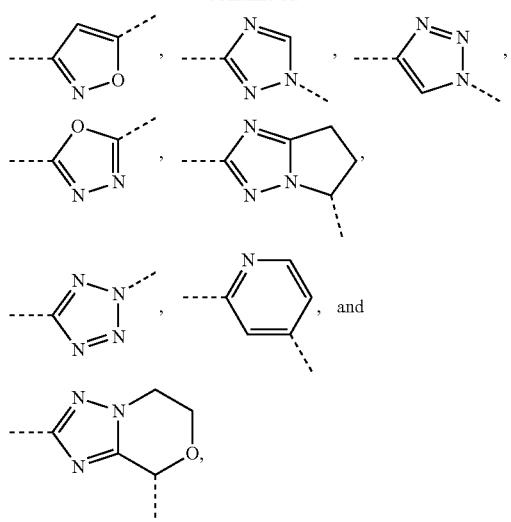

wherein the

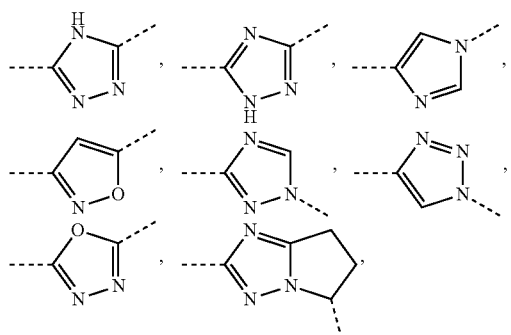

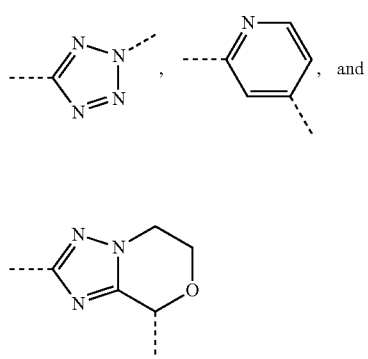

are optionally substituted with 1, 2 or 3 halogen or $C_{1-3}$ alkyl.

12. The compound, or the stereoisomer or the pharmaceutically acceptable salt thereof according to claim 1, wherein L is selected from the group consisting of single bond, —$CH_2$— and —O—.

13. The compound, or the stereoisomer or the pharmaceutically acceptable salt thereof according to claim 1, wherein the compound is selected from the group consisting of

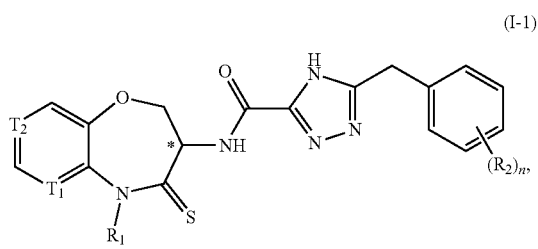
(I-1)

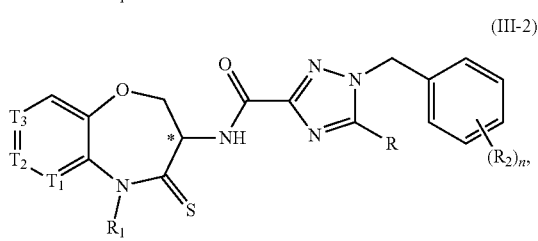
(III-2)

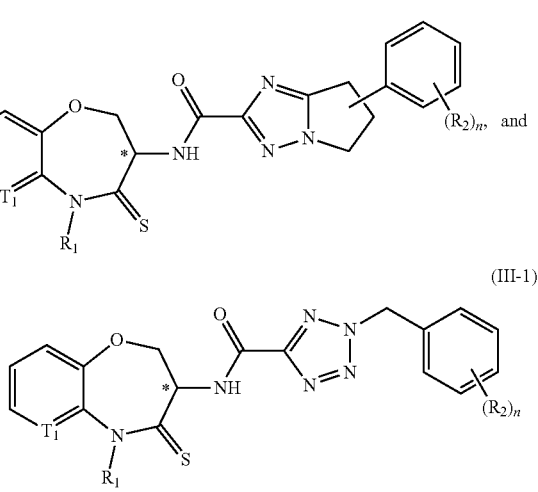
(I-3)

(III-1)

wherein n, $T_1$, $T_2$ and $T_3$ are as defined in claim 1;

$R_1$ is as defined in claim 1;

$R_2$ is as defined in claim 1;

R is selected from H and halogen; and the carbon atom with "*" is a chiral carbon atom, which exists in the form of a single (R) or(S) enantiomer or a mixture enriched in one enantiomer.

14. The compound, or the stereoisomer or the pharmaceutically acceptable salt thereof according to claim 13, wherein the compound is selected from the group consisting of

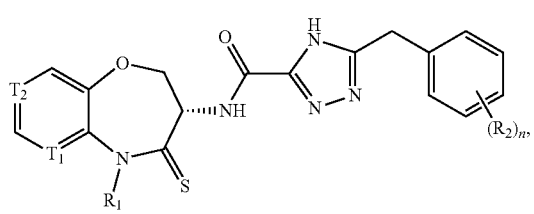
(I-5)

-continued
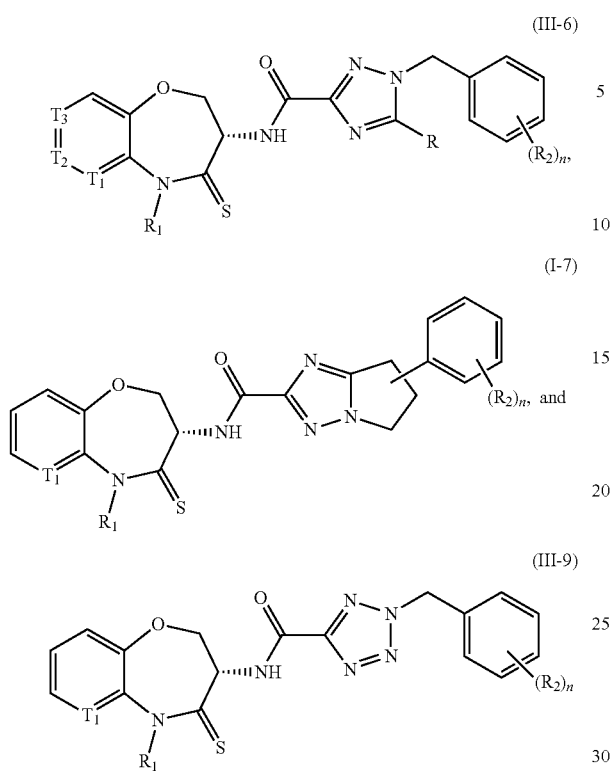
wherein
n, $T_1$, $T_2$ and $T_3$ are as defined in claim 1;
$R_1$ is as defined in claim 1;
$R_2$ is as defined in claim 1; and
R is selected from H and halogen.
15. A compound of the following formula:
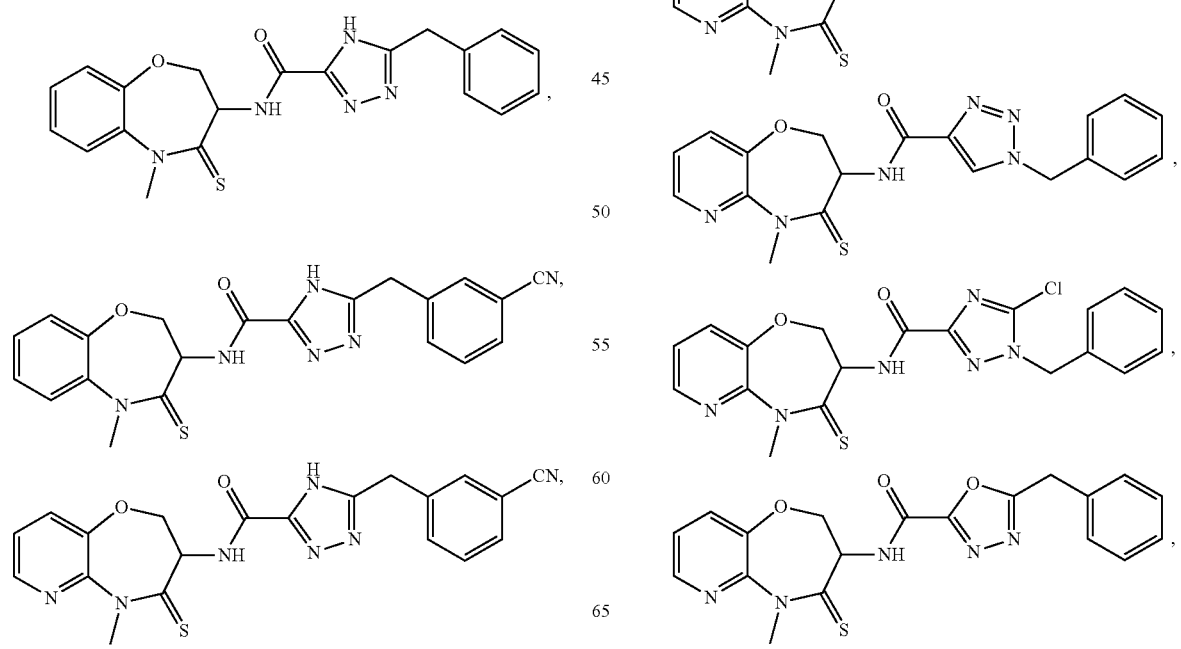
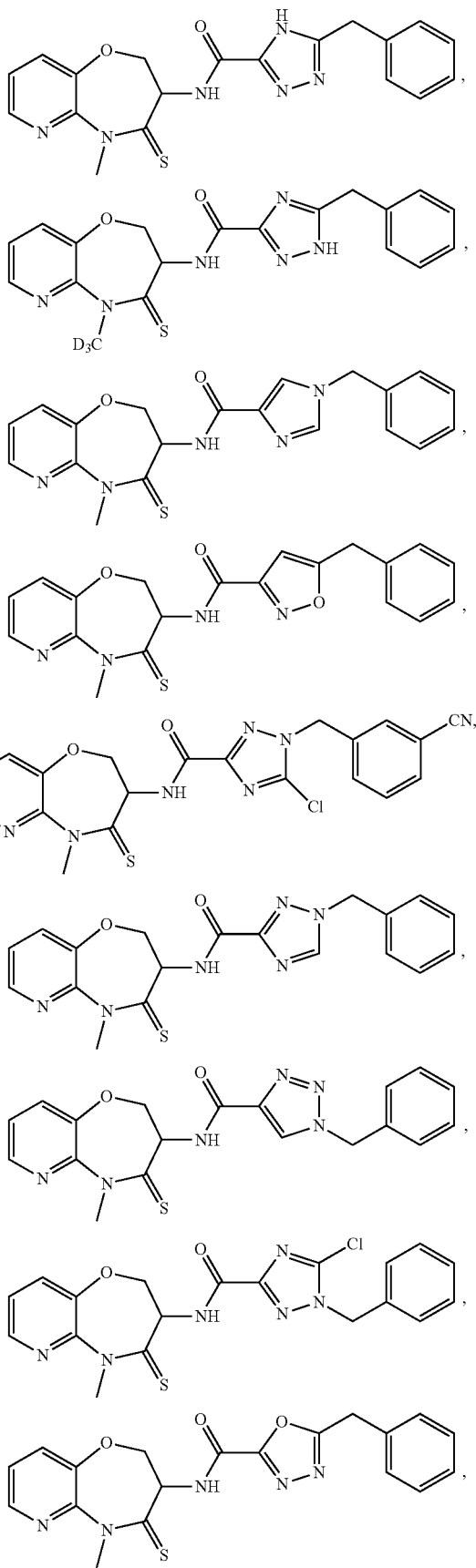

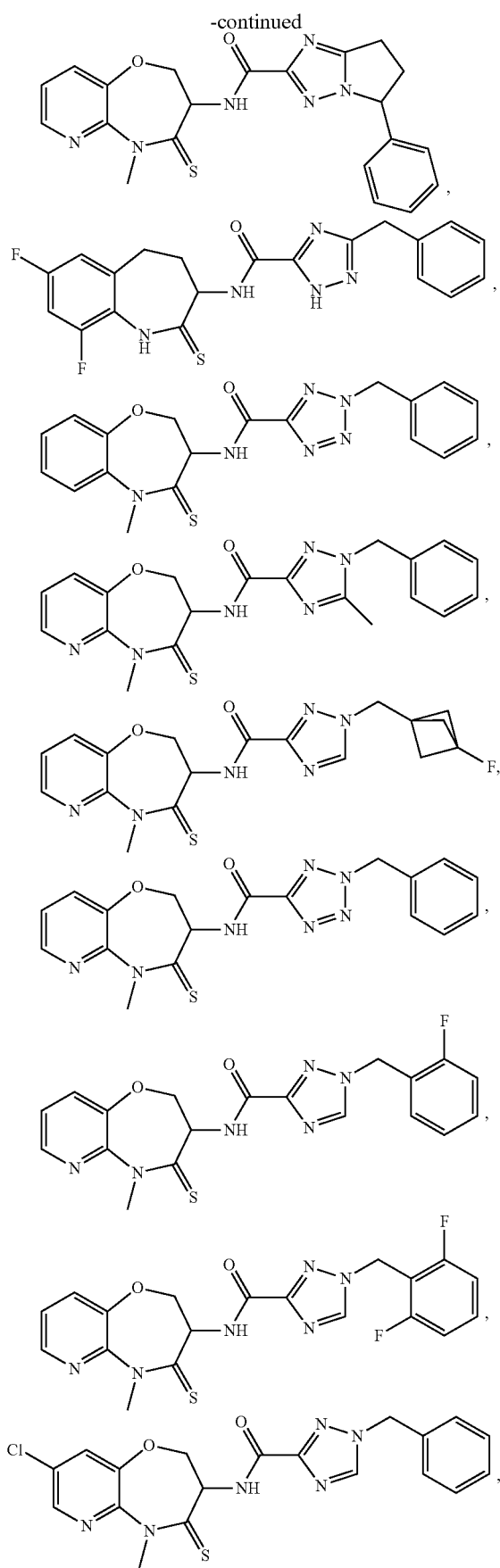
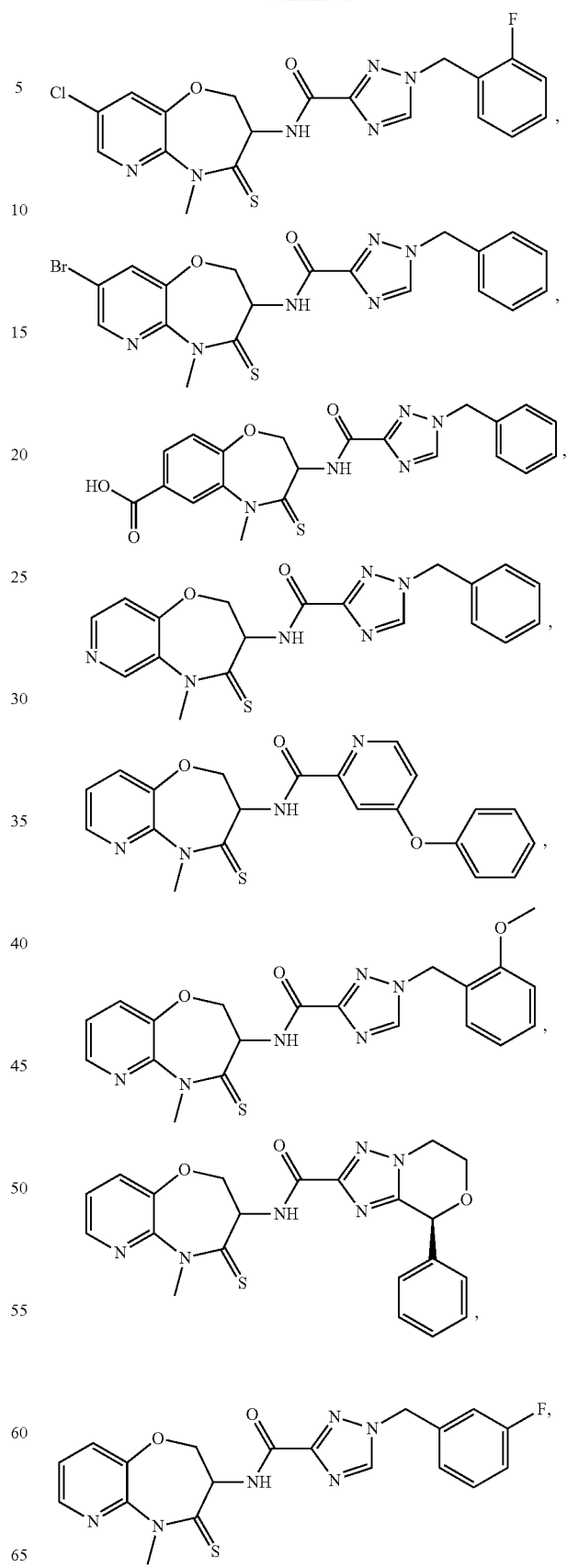

-continued
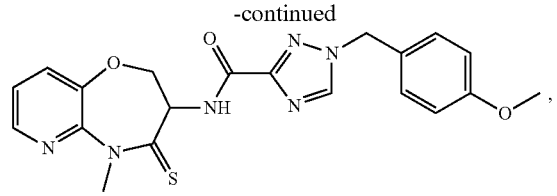
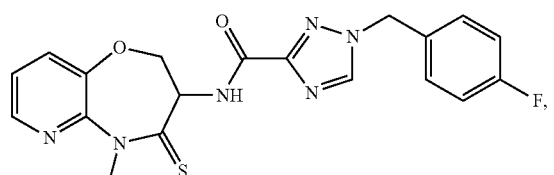
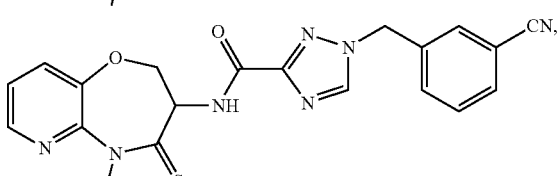
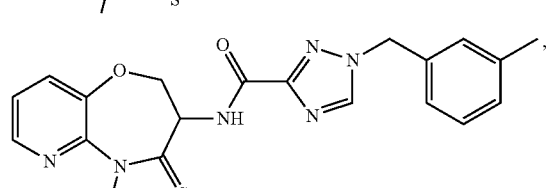
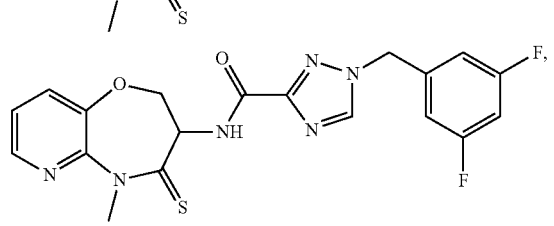
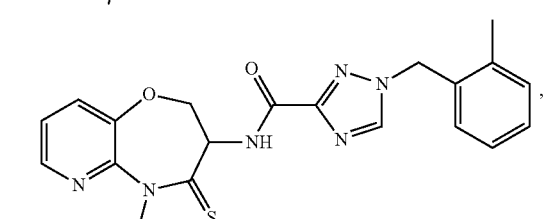
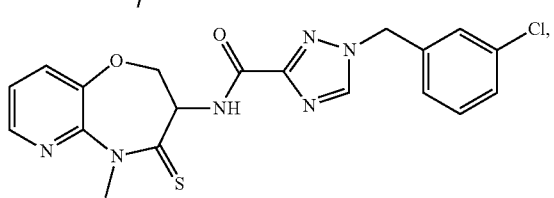
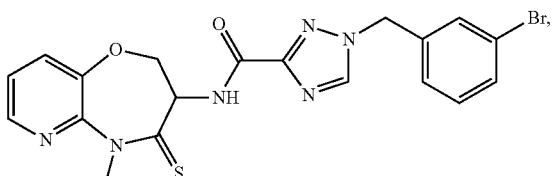
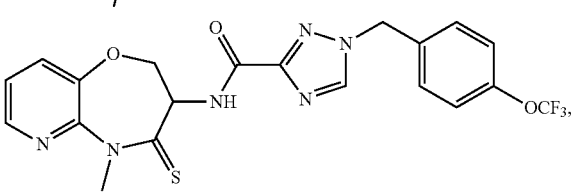
-continued
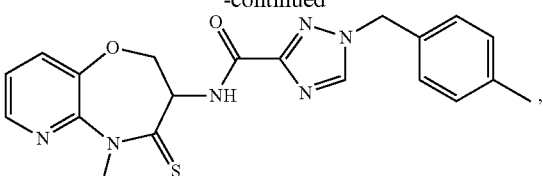
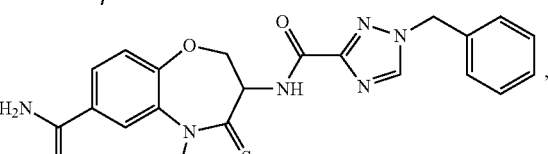
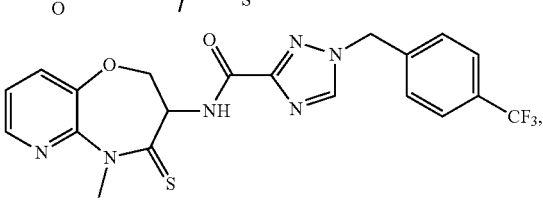
or
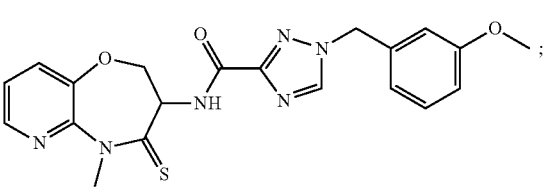
or a stereoisomer or a pharmaceutically acceptable salt thereof.
16. The compound according to claim 1, wherein the compound is selected from the group consisting of
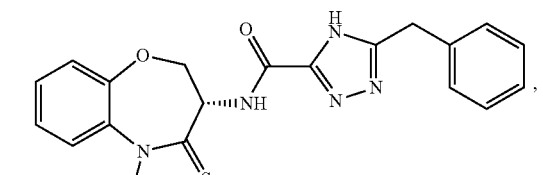
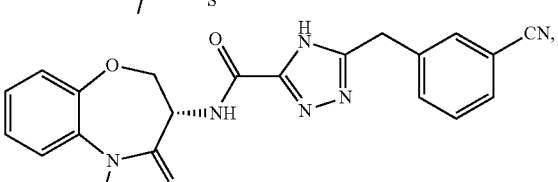
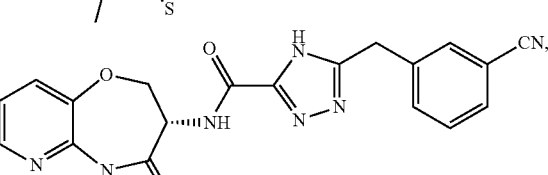
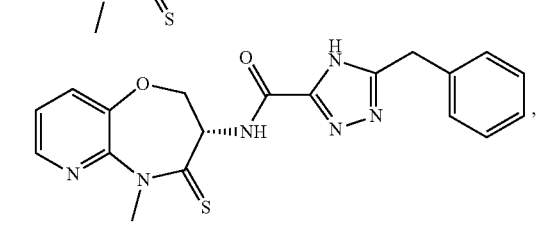

131
-continued
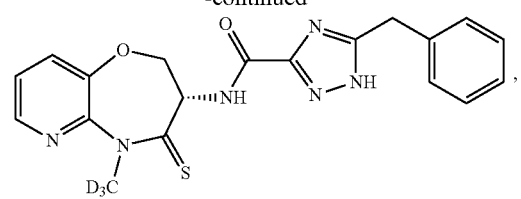
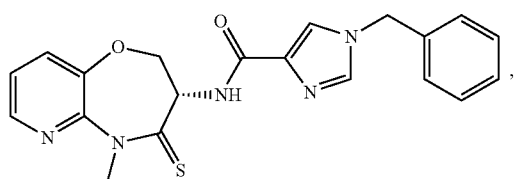
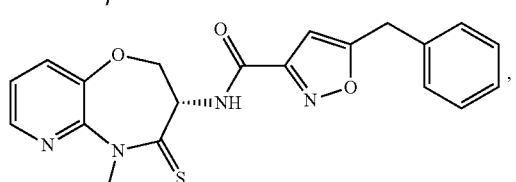
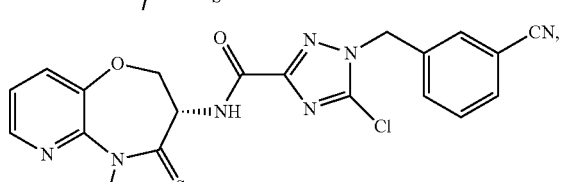
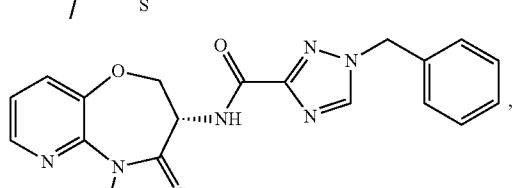
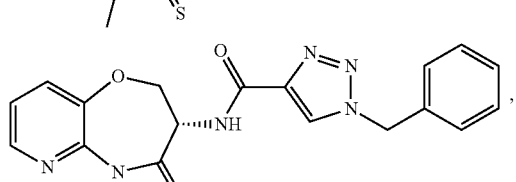
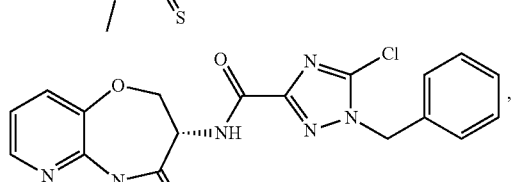
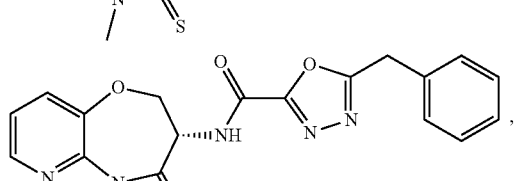
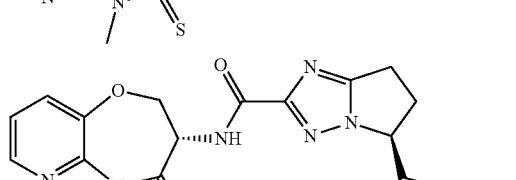
132
-continued
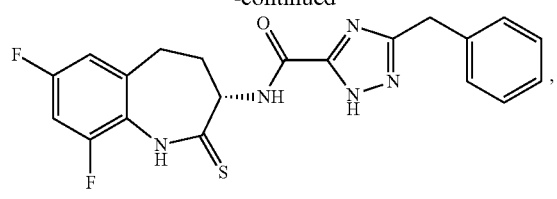
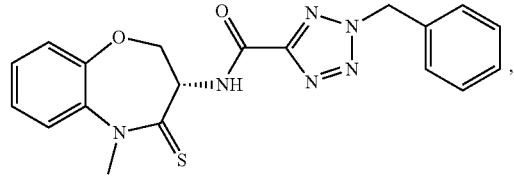
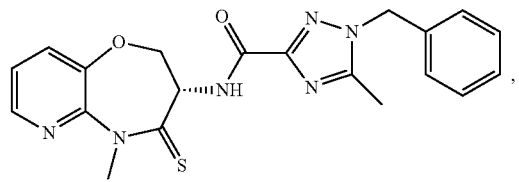
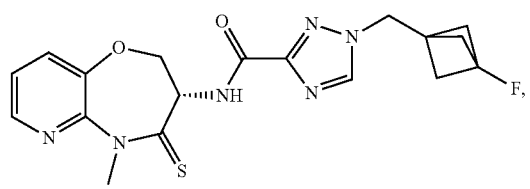
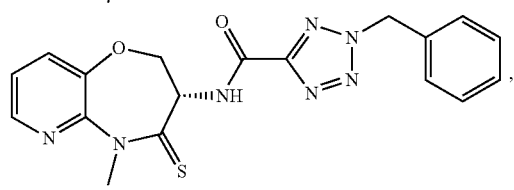
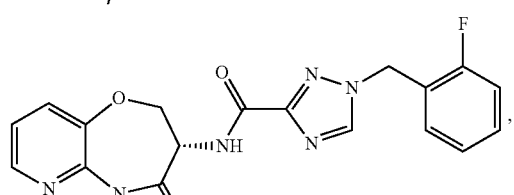
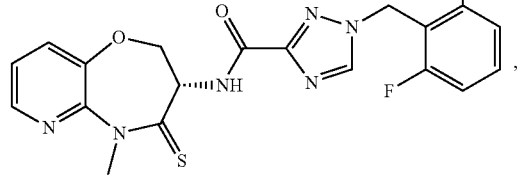
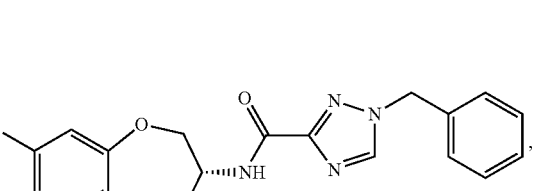

133
-continued
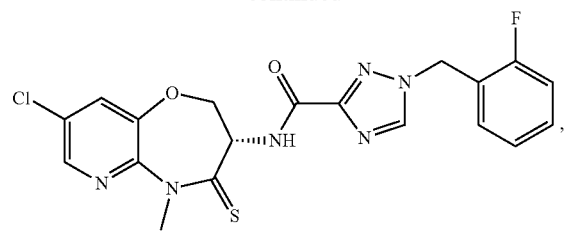
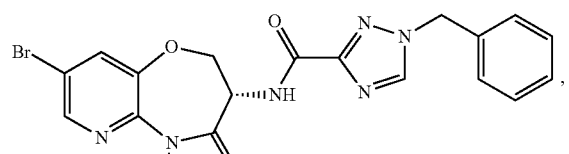
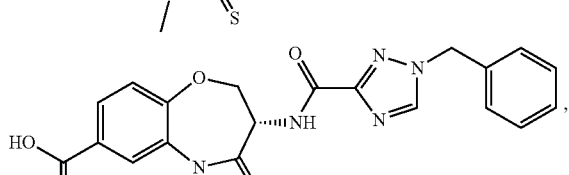
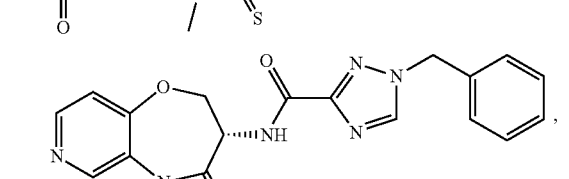
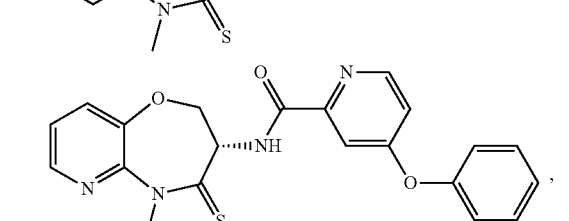
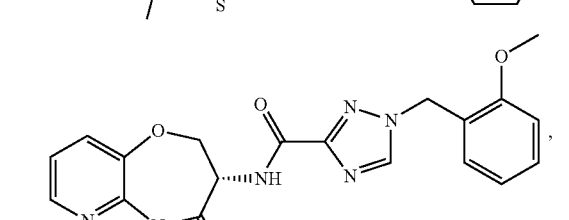
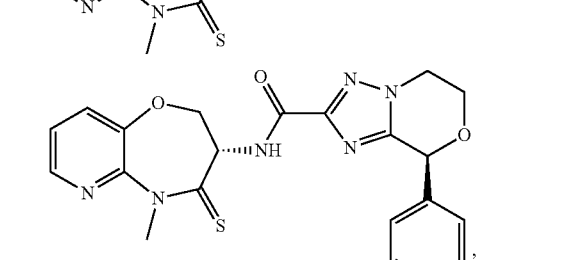
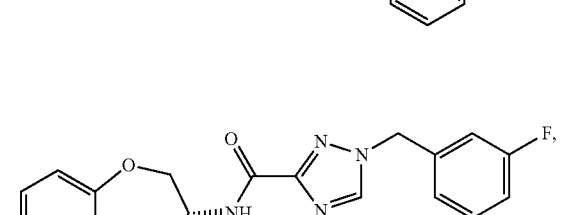
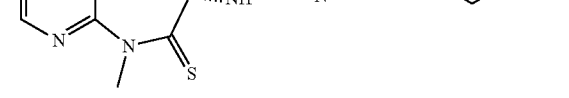
134
-continued
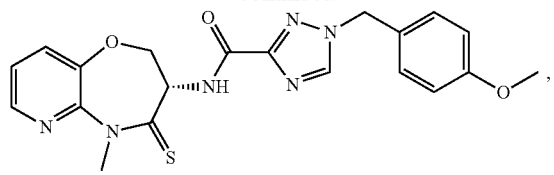
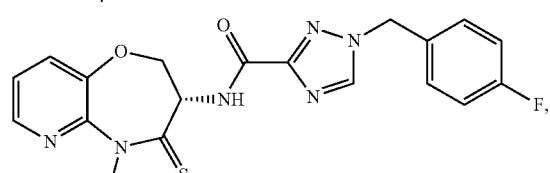
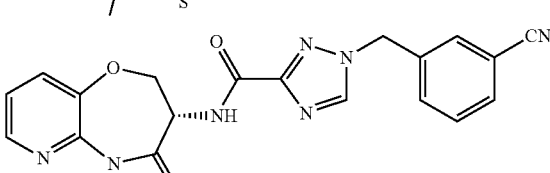
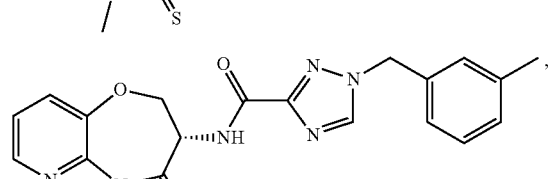
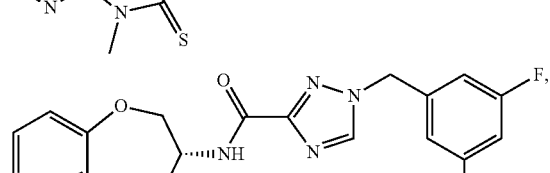
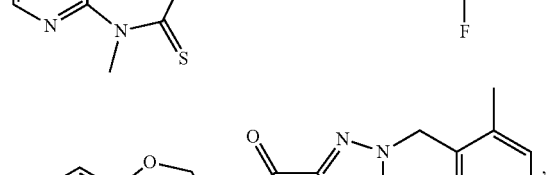
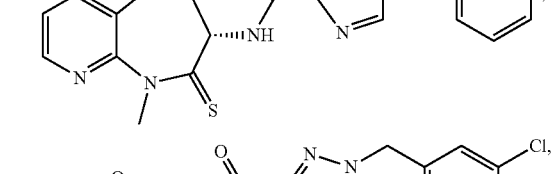
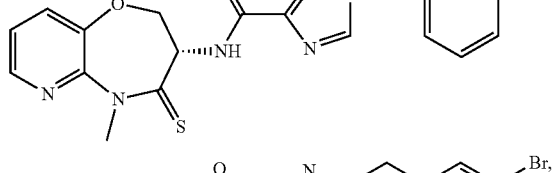
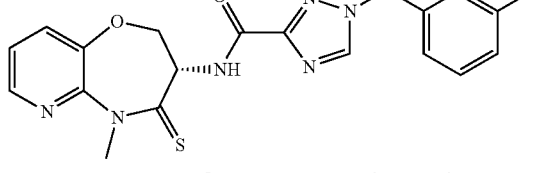
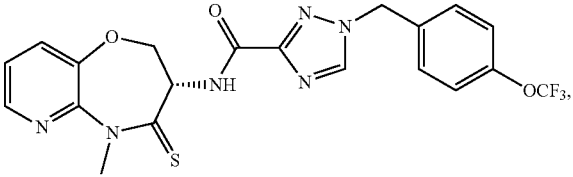

-continued

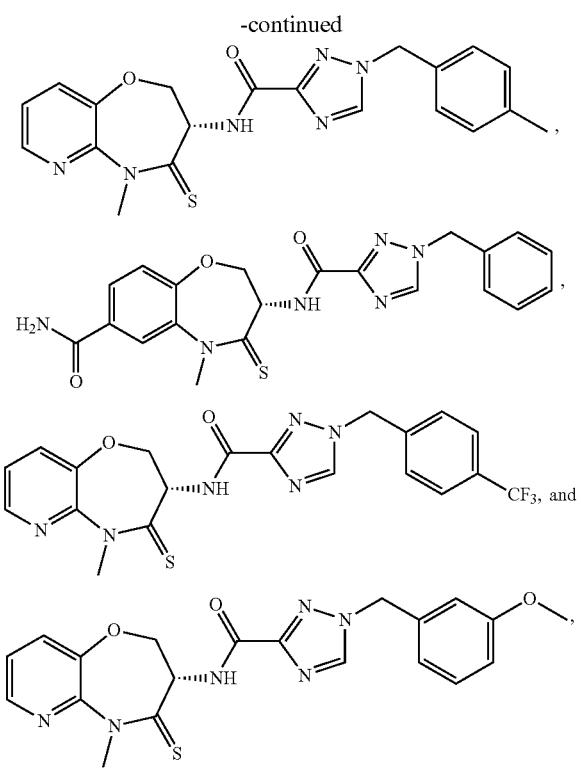

or the stereoisomer or the pharmaceutically acceptable salt thereof.

17. The compound, or the stereoisomer, or the pharmaceutically acceptable salt thereof according to claim 1, wherein A is L

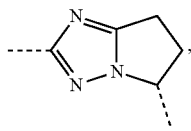

is a single bond, and B is phenyl.

18. The compound, or the stereoisomer, or the pharmaceutically acceptable salt thereof according to claim 1, wherein A is

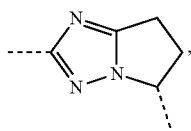

L is a single bond, B is phenyl, and the carbon atom of Formula I with "*" is a chiral carbon atom with S absolute chemistry.

19. A method of treating a disease related to RIP-1 kinase in a subject in need thereof, comprising administering to the subject the compound, or the stereoisomer or the pharmaceutically acceptable salt thereof according to claim 1, wherein the disease related to RIP-1 kinase is an inflammatory disease.

* * * * *